United States Patent
Jeschke et al.

(12)

(10) Patent No.: US 6,291,472 B1
(45) Date of Patent: Sep. 18, 2001

(54) 4A, 5A, 8A, 8B-TETRAHYDRO-6H-PYRROLO [3',4':4, 5]FURO[3,2-B] PYRI-DINE-6,8(7H)-DIONE DERIVATIVES FOR CONTROL OF ENDOPARASITES PROCESSES FOR THEIR PREPARATION

(75) Inventors: Peter Jeschke, Leverkusen; Achim Harder, Köln; Norbert Mencke, Leverkusen, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/577,056

(22) Filed: May 22, 2000

Related U.S. Application Data

(62) Division of application No. 09/051,607, filed as application No. PCT/EP96/04346 on Oct. 7, 1996, now Pat. No. 6,110,928.

(30) Foreign Application Priority Data

Oct. 19, 1995 (DE) .............................. 195 38 960

(51) Int. Cl.[7] ................ A61K 31/4435; C07D 491/147; C07D 413/14
(52) U.S. Cl. ............................. 514/291; 546/80; 546/82; 546/83; 546/84; 544/106; 544/111
(58) Field of Search .................................. 544/106, 111; 546/80, 82, 83, 84; 514/291, 256

(56) References Cited

PUBLICATIONS

Caplus 112:54647 abstact, Harano Kazunobu et al, Heterocycles 1989 vol 29 issue 6 pp. 1029–1032.*
Caplus 108:36887 abstract, Hisano takuso et al, Chem. pharm Bull. 1987, vol 35 issue 3 pp. 1049–1057, 1987.*
Caplus 112:54647, Harano Kazunobu et al, English Abstract Heterocycles 1989, vol. 29, Issu 6 pp. 1029–1032.*
Caplus 115:8613, Matsuoko et al, English Abstract Chem Pharm Bull 1991 vol. 39 Issue 1 pp. 10–17, 1991.*

* cited by examiner

Primary Examiner—Alan L. Rotman
Assistant Examiner—Rita Desai
(74) Attorney, Agent, or Firm—Joseph C. Gil; Godfried R. Akorli

(57) ABSTRACT

The present invention relates to the use of 4a, 5a, 8a, 8b-tetrahydro-6H-pyrrolo[3',4':4,5]furo[3,2-b]pyridine-6,8 (7H)-dione derivatives of the general formula (I) and salts thereof,

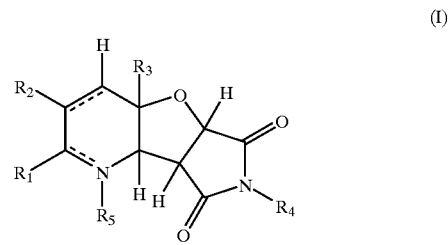

(I)

in which the radicals $R^1$ to $R^5$ have the meaning given in the description, and to novel 4a, 5a, 8a, 8b-tetrahydro-6H-pyrrolo[3',4':4,5]furo[3,2-b]pyridine-6,8(7H)-dione derivatives and processes for their preparation.

4 Claims, No Drawings

4A, 5A, 8A, 8B-TETRAHYDRO-6H-PYRROLO[3',4':4, 5]FURO[3,2-B] PYRI-DINE-6,8(7H)-DIONE DERIVATIVES FOR CONTROL OF ENDOPARASITES PROCESSES FOR THEIR PREPARATION

This is a divisional of application Ser. No. 09/051,607, filed Apr. 15, 1998, now U.S. Pat. No. 6,110,928, issued Aug. 29, 2000, which is a 371 of PCT/EP96/04346, filed Oct. 7, 1996.

The present invention relates to the use of 4a, 5a, 8a, 8b-tetrahydro-6H-pyrrolo[3',4': 4,5]furo[3,2-b]pyridine-6,8 (7H)-dione derivatives for the control of endoparasites, to novel 4a, 5a, 8a, 8b-tetrahydro-6H-pyrrolo[3',4': 4,5]furo[3,2-b]pyridine-6,8 (7H)-dione derivatives and processes for their preparation.

Some 4a, 5a, 8a, 8b-tetrahydro-6H-pyrrolo[3',4': 4,5]furo[3,2-b]pyridine-6,8(7H)-dione derivatives are already known. However, nothing is known of their use against endoparasites (cf. for example: T. Hisano et al. Chem. Pharm. Bull. 35 (3), (1987) pages 1049–1057;Heterocycles 29 (6), (1989) pages 1029–1032; Chem. Pharm. Bull. 38 (3), (1990) pages 605–611; Chem. Pharm. Bull. 39 (1), (1991) pages 10–17).

The present invention relates to:
1. The use of 4a, 5a, 8a, 8b-tetrahydro-6H-pyrrolo[3',4': 4,5]furo[3,2-b]pyridine-6,8(7H)-dione derivatives of the general formula (I) and salts thereof,

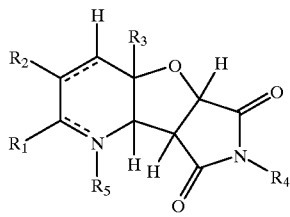

(I)

in which
- $R^1$ represents hydrogen, straight-chain or branched alkyl, cycloalkyl, arylalkyl, aryl, heteroaryl, heteroarylalkyl, which are optionally substituted,
- $R^2$ represents hydrogen, straight-chain or branched alkyl, cycloalkyl, alkoxycarbonyl, which are optionally substituted,
- $R^1$ and $R^2$, together with the atoms to which they are bonded, represent a 5- or 6-membered ring, which can optionally be interrupted by oxygen, sulfur, sulfoxyl or sulfonyl and is optionally substituted,
- $R^3$ represents hydrogen, straight-chain or branched alkyl, cycloalkyl, alkoxycarbonyl, which are optionally substituted,
- $R^4$ represents hydrogen, straight-chain or branched alkyl, alkenyl, alkinyl, cycloalkyl, cycloalkylalkyl, aryl, arylalkyl, heteroaryl, heteroarylalkyl, amino, alkylamino, dialkylamino, cycloalkylamino, which are optionally substituted,
- $R^5$ represents hydrogen, straight-chain or branched alkyl, alkenyl, alkinyl, cycloalkyl, cycloalkylalkyl, aryl, arylalkyl, heteroaryl, heteroarylalkyl, which are optionally substituted, formyl, alkoxydicarbonyl or optionally represents a radical from the group consisting of $G^1$, $G^2$, $G^3$ and $G^4$

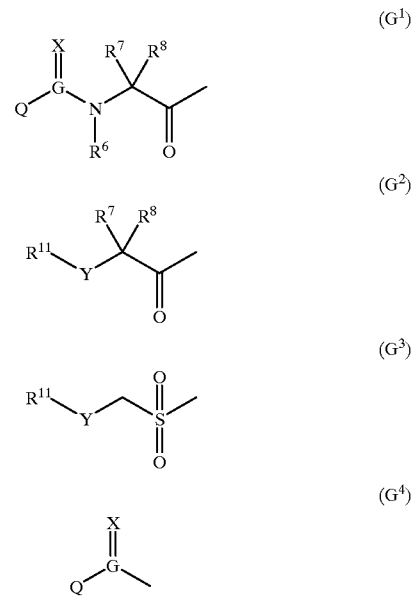

in which
- $R^6$ represents hydrogen, straight-chain or branched alkyl, cycloalkyl, aryl, arylalkyl, heteroaryl, heteroarylalkyl, which are optionally substituted,
- $R^6$ and $R^7$, together with the atoms to which they are bonded, represent a 5- or 6-membered ring, which can optionally be interrupted by oxygen, sulfur, sulfoxyl or sulfonyl and is optionally substituted, stand,
- $R^7$ and $R^8$ independently of one another represent hydrogen, straight-chain or branched alkyl, alkenyl, cycloalkyl, cycloalkylalkyl, aryl, arylalkyl, heteroaryl, heteroarylalkyl, which are optionally substituted, or
- $R^7$ and $R^8$ together represent a spirocyclic ring which is optionally substituted,

can denote carboxyl, thiocarboxyl, —C=CH—NO$_2$, —C=CH—CN, —C=C—R$^9$, sulfoxyl, sulfonyl, —P(O)—OR$^{10}$ or P(S)—OR$^{10}$,

- $R^9$ represents hydrogen, hydroxyl, alkoxy, alkylcarbonyl, halogenoalkylcarbonyl, alkylsulfonyl, nitro or cyano, and
- $R^{10}$ represents hydrogen or alkyl, and
- Q represents straight-chain or branched alkyl, alkenyl, alkinyl, cycloalkyl, aryl, arylalkyl, hetaryl or hetarylalkyl, which are optionally substituted, or optionally represents a radical from the group consisting of $G^5$ and $G^6$

(G$^5$)

-continued

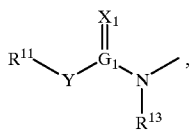
(G⁶)

in which

can denote carboxyl, thiocarboxyl or sulfonyl,

Y represents oxygen, sulfur or —NR$^{12}$,

R$^{11}$, in the case where Y represents nitrogen, can denote a cyclic amino group linked via a nitrogen atom, R$^{11}$ and R$^{12}$ independently of one another represent hydrogen, straight-chain or branched alkyl, alkenyl, alkinyl, cycloalkyl, cycloalkylalkyl, aryl, arylalkyl, heteroaryl, heteroarylalkyl, which are optionally substituted, or R$^{11}$ and R$^{12}$, together with the adjacent N atom, for a carbocyclic 5-, 6- or 7-membered ring system or for a 7 to 10-membered bicyclic ring system, which can optionally also be interrupted by oxygen, sulfur, sulfoxyl, sulfonyl, carbonyl, —N—O, —N=, —NR$^{14}$— or by quaternized nitrogen and is optionally substituted, R$^{13}$ represents hydrogen or alkyl, R$^{14}$ represents hydrogen, straight-chain or branched alkyl, alkenyl, alkinyl, cycloalkyl, cycloalkylalkyl, alkoxycarbonyl, alkylcarbonyl, cycloalkylcarbonyl, cyano, aryl, arylalkyl, heteroaryl, heteroarylalkyl stand which are optionally substituted, for control of endoparasites in medicine and veterinary medicine.

The compounds of the formula (I) can occur as geometric and/or optical isomers or isomer mixtures of different composition, depending on the nature of the substituents. The invention relates both to the pure isomers and to the isomer mixtures.

In the formula (I), the broken line can denote a single bond or represent one or two double bonds between the carbon atom which carries the substituent R$^2$ and the adjacent carbon atom, and/or between the carbon atom and the adjacent nitrogen atom which carry the substituents R$^1$ and R$^5$.

In the case where a double bond is present between the carbon atom which carries the substituent R$^1$ and the adjacent nitrogen atom with a substituent R$^5$, the compounds of the formula (I) are in the form of their salts.

The 4a, 5a, 8a, 8b-tetrahydro-6H-pyrrolo[3',4': 4,5]furo[3,2-b]pyridine-6,8(7H)-dione derivatives of the general formula (I) and salts thereof

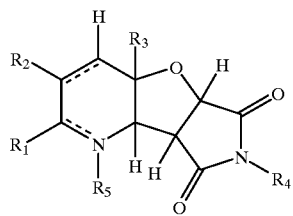
(I)

in which

R$^1$ represents hydrogen, straight-chain or branched alkyl having up to 4 carbon atoms, C$_{3-6}$-cycloalkyl, aryl-C$_{1-2}$-alkyl, aryl, heteroaryl, heteroaryl-C$_{1-2}$-alkyl, which are optionally substituted, R$^1$ and R$^2$, together with the atoms to which they are bonded, represent a 5- or 6-membered ring, which is optionally substituted, R$^2$ and R$^3$ independently of one another represent hydrogen, straight-chain or branched alkyl having up to 4 carbon atoms, halogenoalkyl, hydroxyalkyl, C$_{1-4}$-alkanoyloxyalkyl, C$_{1-2}$-alkoxyalkyl, C$_{1-2}$-mercaptoalkyl, C$_{1-2}$-alkylthioalkyl, C$_{1-2}$alkylsulfinylalkyl, C$_{1-2}$alkylsulfonylalkyl, aminoalkyl, C$_{1-6}$-alkylaminoalkyl, C$_{1-6}$-dialkylaminoalkyl, C$_{3-6}$-cycloalkylaminoalkyl, C$_{3-6}$-cycloalkyl, C$_{1-4}$-alkoxycarbonyl, R$^4$ represents hydrogen, straight-chain or branched C$_{1-6}$-alkyl, halogeno-C$_{1-6}$-alkyl, hydroxy-C$_{1-6}$-alkyl, C$_{1-4}$-alkanoyloxyalkyl, C$_{1-2}$-alkoxyalkyl, C$_{1-4}$alkoxycarbonyl-C$_{1-4}$-alkyl, amino-C$_{1-6}$-alkyl, C$_{1-6}$ alkylamino-C$_{1-6}$-alkyl, C$_{1-6}$-dialkylamino-C$_{1-6}$alkyl, C$_{1-6}$-trialkylammonium-C$_{1-6}$-alkyl halide, C$_{2-6}$-alkenyl, C$_{2-6}$-alkinyl, C$_{3-6}$-cycloalkyl, C$_{3-6}$-cycloalkyl-C$_{1-2}$-alkyl, aryl, aryl-C$_{1-2}$-alkyl, heteroaryl, heteroaryl-C$_{1-2}$-alkyl, amino, C$_{1-4}$-alkylamino, C$_{1-4}$-dialkylamino, C$_{3-7}$-cycloalkylamino, which are optionally substituted, R$^5$ for hydrogen, straight-chain or branched C$_{1-6}$-alkyl, halogeno-C$_{1-6}$-alkyl, hydroxy-C$_{1-6}$-alkyl, C$_{1-4}$-alkanoyloxyalkyl, C$_{1-2}$-alkoxyalkyl, amino-C$_{1-6}$-alkyl, C$_{1-6}$-alkylamino-C$_{1-6}$-alkyl, C$_{1-6}$-dialkylamino-C$_{1-6}$-alkyl, C$_{1-6}$-trialkylammonium-C$_{1-6}$-alkyl halide, nitro-C$_{1-4}$-alkyl, cyano-C$_{1-4}$-alkyl, C$_{1-4}$-alkoxycarbonyl-C$_{1-4}$-alkyl, carbamoyl-C$_{1-4}$-alkyl, carboxyl-C$_{1-4}$-alkyl, C$_{2-6}$-alkenyl, C$_{2-6}$-alkinyl, C$_{3-6}$-cycloalkyl, C$_{3-6}$-cycloalkyl-C$_{1-2}$-alkyl, aryl, aryl-C$_{1-2}$-alkyl, heteroaryl, heteroaryl-C$_{1-2}$-alkyl, formyl, C$_{1-4}$-alkoxydicarbonyl, or for a radical from the group consisting of G$^1$, G$^2$, G$^3$ and G$^4$

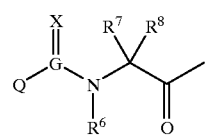
(G$^1$)

-continued

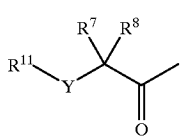
(G²)

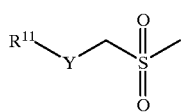
(G³)

(G⁴)

in which $R^6$ represents hydrogen, straight-chain or branched $C_{1-6}$-alkyl, $C_{3-6}$-cycloalkyl, aryl-$C_{1-2}$-alkyl, heteroaryl-$C_{1-2}$-alkyl, which are optionally substituted, $R^6$ and $R^7$, together with the atoms to which they are bonded, represent a 5- or 6-membered ring, which can optionally be interrupted by oxygen, sulfur, sulfoxyl or sulfonyl and is optionally substituted, stand, $R^7$ and $R^8$ independently of one another represent hydrogen, straight-chain or branched $C_{1-6}$-alkyl, halogeno-$C_{1-6}$-alkyl, hydroxy-$C_{1-6}$-alkyl, $C_{1-4}$-alkanoyloxy-$C_{1-6}$-alkyl, $C_{1-2}$-alkoxy-$C_{1-6}$-alkyl, mercapto-$C_{1-6}$-alkyl, $C_{1-2}$-alkylthio-$C_{1-6}$-alkyl, $C_{1-2}$alkylsulfinyl-$C_{1-6}$-alkyl, $C_{1-2}$-alkylsulfonyl-$C_{1-6}$alkyl, carboxyl-$C_{1-6}$-alkyl, carbamoyl-$C_{1-6}$-alkyl, amino-$C_{1-6}$-alkyl, $C_{1-6}$alkylamino-$C_{1-6}$-alkyl, $C_{1-6}$-dialkylamino-$C_{1-6}$-alkyl, guanidino-$C_{1-6}$-alkyl, which radical can optionally be substituted by one or two benzyloxycarbonyl radicals or by one, two, three or four $C_{1-2}$-alkyl radicals, (1 $_4$-alkoxycarbonylamino-$C_{1-6}$-alkyl, $C_{2-6}$-alkenyl, $C_{3-6}$-cyclo-$C_{1-2}$-alkyl, $C_{3-6}$-cycloalkyl-$C_{1-2}$ alkyl, and represent optionally substituted aryl, aryl-$C_{1-2}$-alkyl, heteroaryl, heteroaryl-$C_{1-2}$-alkyl, or $R^7$ and $R^8$ together represent a spirocyclic ring,

denotes carboxyl, thiocarboxyl, —C=CH—NO₂, —C=CH—CN, —C=C—R⁹, sulfoxyl, sulfonyl, —P(O)—OR¹⁰ or P(S)—OR¹⁰, $R^9$ represents hydrogen, hydroxyl, $C_{1-4}$-alkoxy, $C_{1-4}$-alkylcarbonyl, halogeno-$C_{1-4}$-alkylcarbonyl, $C_{1-4}$-alkylsulfonyl, nitro or cyano, and $R^{10}$ represents hydrogen or $C_{1-4}$-alkyl, and Q represents straight-chain or branched $C_{1-6}$-alkyl, halogeno-$C_{1-6}$-alkyl, hydroxy-$C_{1-6}$-alkyl, $C_{1-4}$-alkanoyloxyalkyl, $C_{1-2}$-alkoxyalkyl, mercaptoalkyl, $C_{1-2}$-alkylthioalkyl, $C_{1-2}$-alkylsulfinylalkyl, $C_{1-2}$-alkylsulfonylalkyl, carboxyalkyl, carbamoylalkyl, amino-$C_{1-6}$-alkyl, $C_{1-6}$-alkylamino-$C_{1-6}$-alkyl, $C_{1-6}$-dialkylamino-$C_{1-6}$-alkyl, guanidino-$C_{1-6}$-alkyl, which radical can optionally be substituted by one or two benzyloxycarbonyl radicals, tert-butyloxycarbonyl radicals or by one, two, three or four $C_{1-2}$-alkyl radicals, $C_{1-4}$-alkoxycarbonylaminoalkyl, $C_{2-6}$-alkenyl, $C_{2-6}$-alkinyl, $C_{3-6}$-cycloalkyl, aryl, aryl-$C_{1-2}$-alkyl, heteroaryl or heteroaryl-$C_{1-2}$-alkyl, which are optionally substituted, or optionally represents a radical from the group consisting of G⁵ and G⁶

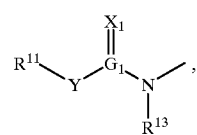
(G⁵)

(G⁶)

in which

can denote carboxyl, thiocarboxyl or sulfonyl,

Y represents oxygen, sulfur or —NR¹², $R^{11}$, in the case where Y represents nitrogen, can denote a cyclic amino group linked by a nitrogen atom, $R^{11}$ and $R^{12}$ independently of one another represent hydrogen, straight-chain or branched $C_{1-6}$-alkyl, $C_{2-6}$-alkenyl, $C_{2-6}$-alkinyl, $C_{3-6}$-cycloalkyl, $C_{3-6}$-cycloalkyl-$C_{1-2}$-alkyl, aryl, aryl-$C_{1-2}$-alkyl, heteroaryl, heteroaryl-$C_{1-2}$-alkyl, which are optionally substituted, or $R^{11}$ and $R^{12}$, together with the adjacent N atom, for a carbocyclic 5-, 6- or 7-membered ring system, or for a 7 to 10-membered bicyclic ring system, which can optionally also be interrupted by oxygen, sulfur, sulfoxyl, sulfonyl, carbonyl, —N—O, —N=, —NR¹⁴— or by quaternized nitrogen and is optionally substituted, $R^{13}$ represents hydrogen or $C_{1-4}$-alkyl, $R^{14}$ represents hydrogen, straight-chain or branched $C_{1-6}$-alkyl, $C_{1-6}$-alkenyl, $C_{2-6}$-alkinyl, $C_{3-8}$-cycloalkyl, $C_{3-8}$-cycloalkyl-$C_{1-2}$-alkyl, $C_{1-4}$-alkoxycarbonyl, $C_{1-4}$-alkylcarbonyl, $C_{3-6}$-cycloalkylcarbonyl, cyano, aryl, aryl-$C_{1-2}$-alkyl, heteroaryl, heteroaryl-$C_{1-2}$-alkyl stand, which are optionally substituted, and optical isomers and racemates thereof, are preferably used for control of endoparasites in medicine and veterinary medicine.

The compounds of the general formula (I) are known in some cases and can be prepared by processes analogous to known processes.

The invention furthermore relates to:

2. Novel 4a, 5a, 8a, 8b-tetrahydro-6H-pyrrolo[3',4': 4,5]furo[3,2-b]pyridine-6,8(7H)-dione derivatives of the general formula (Ia) and salts thereof, (Ia)

in which
R¹ represents hydrogen, straight-chain or branched alkyl having up to 4 carbon atoms, $C_{3-6}$-cycloalkyl, aryl-$C_{1-2}$-alkyl, aryl, heteroaryl, heteroaryl-$C_{1-2}$-alkyl, which are optionally substituted, R² and R³ independently of one another represent hydrogen, straight-chain or branched alkyl having up to 4 carbon atoms, halogenoalkyl, hydroxyalkyl, $C_{1-4}$-alkanoyloxyalkyl, $C_{1-2}$-alkoxyalkyl, $C_{1-2}$-mercaptoalkyl, $C_{1-2}$-alkylthioalkyl, $C_{1-2}$-alkylsulfinylalkyl, $C_{1-2}$-alkylsulfonylalkyl, aminoalkyl, $C_{1-6}$-alkylaminoalkyl, $C_{1-6}$-dialkylaminoalkyl, $C_{3-6}$-cycloalkylaminoalkyl, $C_{3-6}$-cycloalkyl, $C_{1-4}$-alkoxycarbonyl, R⁴ represents hydrogen, straight-chain or branched $C_{1-6}$-alkyl, halogeno-$C_{1-6}$-alkyl, hydroxy-$C_{1-6}$-alkyl, $C_{1-4}$-alkanoyloxyalkyl, $C_{1-6}$-alkoxyalkyl, $C_{1-4}$-alkoxycarbonyl-$C_{1-4}$-alkyl, amino-$C_{1-6}$-alkyl, $C_{1-6}$-alkylamino-$C_{1-6}$-alkyl, $C_{1-6}$-dialkylamino-$C_{1-6}$-alkyl, $C_{1-6}$-trialkylammonium-$C_{1-6}$-alkyl halide, $C_{2-6}$-alkenyl, $C_{2-6}$-alkinyl, $C_{3-6}$-cycloalkyl, $C_{3-6}$-cycloalkyl-$C_{1-2}$-alkyl, aryl, aryl-$C_{1-2}$-alkyl, heteroaryl, heteroaryl-$C_{1-2}$-alkyl, amino, $C_{1-4}$-alkylamino, $C_{1-4}$-dialkylamino, $C_{3-7}$-cycloalkylamino, which are optionally substituted, with the proviso in the case where
R¹ represents hydrogen,
R² and R³ represent methyl,
R⁴ represents radicals other than methyl, n-butyl, phenyl, 2-, 3- or 4-methylphenyl, 2-, 3- or 4-chlorophenyl, 2-, 3- or 4-fluorophenyl, 2-chloro, 4-fluorophenyl, 2-fluoro, 4-chlorophenyl, 3-chloro, 4fluorophenyl, 2-, 3- or 4-nitrophenyl, 4-methoxyphenyl and optical isomers and racemates thereof.

3. Process for the preparation of the novel 4a, 5a, 8a, 8b-tetrahydro-6H-pyrrolo[3',4': 4,5]furo[3,2-b]pyridine-6,8(7H)-dione derivatives of the general formula (Ia) and salts thereof, (Ia)

in which
R¹, R², R³ and R⁴ have the meaning given under point 2, characterized in that a) pyridine N-oxides of the general formula (II)

(II)

in which
R¹, R² and R³ have the meaning given under point 2, are reacted with maleic acid imides of the general formula (III)

(III)

in which
R⁴ has the meaning given under point 2, if appropriate in the presence of a diluent.

The invention furthermore relates to:

4. Novel 1, 2, 3, 4, 4a, 5a, 8a, 8b-octahydro-6H-pyrrolo[3',4': 4,5]furo[3,2-b]pyridine-6,8(7H)-dione and 1, 2, 4a, 5a, 8a, 8b-hexahydro-6H-pyrrolo[3',4': 4,5]furo[3,2-b]pyridine-6,8(7H)-dione derivatives of the general formulae (Ib) and (Ic) and salts thereof, (Ib)

(Ic)

in which
R¹ represents hydrogen, straight-chain or branched alkyl having up to 4 carbon atoms, $C_{3-6}$-cycloalkyl, aryl-$C_{1-2}$-alkyl, aryl, heteroaryl, heteroaryl-$C_{1-2}$-alkyl, which are optionally substituted, R² and R³ independently of one another represent hydrogen, straight-chain or branched alkyl having up to 4 carbon atoms, halogenoalkyl, hydroxyalkyl, $C_{1-4}$-alkanoyloxyalkyl, $C_{1-2}$-alkoxyalkyl, $C_{1-2}$- mercaptoalkyl, $C_{1-2}$-alkylthioalkyl, $C_{1-2}$alkylsulfinylalkyl, $C_{1-2}$alkylsulfonylalkyl, aminoalkyl, $C_{1-6}$-alkylaminoalkyl, $C_{1-6}$-dialkylaminoalkyl, $C_{3-6}$-cycloalkyl-aminoalkyl, $C_{3-6}$-cycloalkyl, $C_{1-4}$-alkoxycarbonyl, $R^4$ represents hydrogen, straight-chain or branched $C_{1-6}$-alkyl, halogeno-$C_{1-6}$-alkyl, hydroxy-$C_{1-6}$-alkyl, $C_{1-4}$-alkanoyloxyalkyl, $C_{1-2}$-alkoxyalkyl, $C_{1-4}$alkoxycarbonyl-$C_{1-4}$-alkyl, amino-$C_{1-6}$-alkyl, $C_{1-6}$-alkylamino-$C_{1-6}$-alkyl, $C_{1-6}$-dialkylamino-$C_{1-6}$alkyl, $C_{1-6}$-trialkylammonium-$C_{1-6}$-alkyl halide, $C_{2-6}$-alkenyl, $C_{2-6}$-alkinyl, $C_{3-6}$-cycloalkyl, $C_{3-6}$-cycloalkyl-$C_{1-2}$-alkyl, aryl, aryl-$C_{1-2}$-alkyl, heteroaryl, heteroaryl-$C_{1-2}$-alkyl, amino, $C_{1-4}$-alkylamino, $C_{1-4}$-dialkylamino, $C_{3-7}$-cycloalkylamino, which are optionally substituted, $R^5$ for hydrogen, straight-chain or branched $C_{1-6}$-alkyl, halogeno-$C_{1-6}$-alkyl, hydroxy-$C_{1-6}$-alkyl, $C_{1-4}$-alkanoyloxyalkyl, $C_{1-2}$-alkoxyalkyl, amino-$C_{1-6}$-alkyl, $C_{1-6}$-alkylamino-$C_{1-6}$-alkyl, $C_{1-6}$-dialkylamino-$C_{1-6}$-alkyl, $C_{1-6}$-trialkylammonium-$C_{1-6}$-alkyl halide, nitro-$C_{1-4}$-alkyl, cyano-$C_{1-4}$-alkyl, $C_{1-4}$-alkoxycarbonyl-$C_{1-4}$-alkyl, carbamoyl-$C_{1-4}$-alkyl, carboxyl-$C_{1-4}$-alkyl, $C_{2-6}$-alkenyl, $C_{2-6}$-alkinyl, $C_{3-6}$-cycloalkyl, $C_{3-6}$-cycloalkyl-$C_{1-2}$-alkyl, aryl, aryl-$C_2$alkyl, heteroaryl, heteroaryl-$C_{1-2}$-alkyl, formyl, $C_{1-4}$-alkoxydicarbonyl, or for a radical from the group consisting of $G^1$, $G^2$, $G^3$ and $G^4$

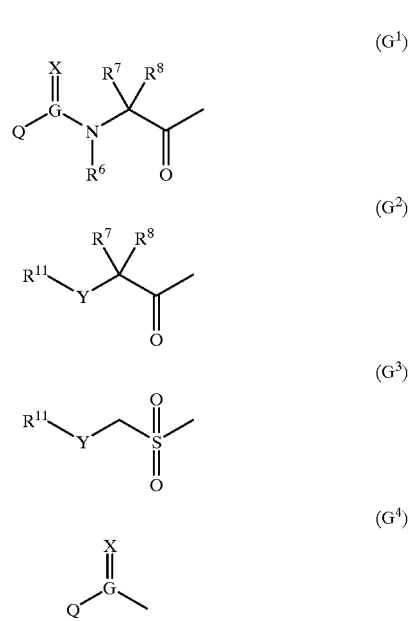

(G$^1$)

(G$^2$)

(G$^3$)

(G$^4$)

in which $R^6$ represents hydrogen, straight-chain or branched $C_{1-6}$-alkyl, $C_{3-6}$-cycloalkyl, aryl-$C_{1-2}$-alkyl, heteroaryl-$C_{1-2}$-alkyl, which are optionally substituted, $R^6$ and $R^7$, together with the atoms to which they are bonded, represent a 5- or 6-membered ring, which can optionally be interrupted by oxygen, sulfur, sulfoxyl or sulfonyl and is optionally substituted, stand, $R^7$ represent hydrogen, straight-chain or branched $C_{1-6}$-alkyl, $C_{2-4}$-alkenyl, $C_{3-6}$-cycloalkyl, $C_{3-6}$-cycloalkyl-$C_{1-2}$-alkyl, and represent optionally substituted aryl, aryl-$C_{1-2}$-alkyl, heteroaryl, heteroaryl-$C_{1-2}$-alkyl, or $R^8$ represents hydrogen or methyl,

can denote carboxyl, thiocarboxyl, —C=CH—NO$_2$, —C=CH—CN, —C=C—R$^9$, sulfoxyl, sulfonyl, —P(O)—OR$^{10}$ or P(S)—OR$^{10}$, $R^9$ represents hydrogen, hydroxyl, $C_{1-4}$-alkoxy, $C_{1-4}$-alkylcarbonyl, halogeno-$C_{1-4}$-alkylcarbonyl, $C_{1-4}$-alkylsulfonyl, nitro or cyano, and $R^{10}$ represents hydrogen or $C_{1-4}$-alkyl, and Q represents straight-chain or branched $C_{1-6}$-alkyl, halogeno-$C_{1-6}$-alkyl, hydroxy-$C_{1-6}$-alkyl, $C_{1-4}$-alkanoyloxyalkyl, $C_{1-2}$-alkoxyalkyl, mercaptoalkyl, $C_{1-2}$-alkylthioalkyl, $C_{1-2}$-alkylsulfinylalkyl, $C_{1-2}$-alkylsulfonylalkyl, carboxyalkyl, carba-moylalkyl, amino-$C_{1-6}$-alkyl, $C_{1-6}$-alkylamino-$C_{1-6}$-alkyl, $C_{1-6}$-dialkylamino-$C_{1-6}$-alkyl, guanidino-$C_{1-6}$-alkyl, which radical can optionally be substituted by one or two benzyloxycarbonyl radicals, tert-butyloxycarbonyl radicals or by one, two, three or four $C_{1-2}$-alkyl radicals, $C_{1-4}$-alkoxycarbonylaminoalkyl, $C_{2-6}$-alkenyl, $C_{1-6}$-alkinyl, $C_{3-6}$-cycloalkyl, aryl, aryl-$C_{1-2}$-alkyl, heteroaryl or heteroaryl-$C_{1-2}$-alkyl, which are optionally substituted, or optionally represents a radical from the group consisting of $G^5$ and $G^6$

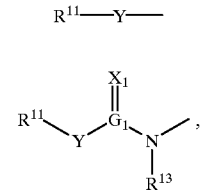

(G$^5$)

(G$^6$)

in which

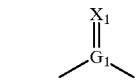

can denote carboxyl, thiocarboxyl or sulfonyl,

Y represents oxygen, sulfur or —NR$^{12}$, $R^{11}$, in the case where Y represents nitrogen, can denote a cyclic amino group linked by a nitrogen atom, $R^{11}$ and $R^{12}$ independently of one another represent hydrogen, straight-chain or branched $C_{1-6}$-alkyl, $C_{2-6}$-alkenyl, $C_{1-6}$-alkinyl, $C_{3-6}$-cycloalkyl, $C_{3-6}$-cycloalkyl-$C_{1-2}$-alkyl, aryl, aryl-$C_{1-2}$-alkyl, heteroaryl, heteroaryl-$C_{1-2}$-alkyl, which are optionally substituted, or $R^{11}$ and $R^{12}$, together with the adjacent N atom, for a carbocyclic 5-, 6- or 7-membered ring system, or for a 7 to 10-membered bicyclic ring system, which can optionally also be interrupted by oxygen, sulfur, sulfoxyl, sulfonyl, carbonyl, —N—O, —N=, —NR$^{14}$— or by quaternized nitrogen and is optionally substituted, $R^{13}$ represents hydrogen or $C_{1-4}$-alkyl, $R^{14}$ represents hydrogen, straight-chain or branched $C_{1-6}$-alkyl, $C_{2-6}$-alkenyl, $C_{2-6}$-alkinyl, $C_{3-6}$-cycloalkyl, $C_{3-8}$- cycloalkyl-$C_{1-2}$-alkyl, $C_{1-4}$-alkoxycarbonyl, $C_{1-4}$-alkylcarbonyl, $C_{3-6}$-cyclo-alkylcarbonyl, cyano, aryl, aryl-$C_{1-2}$-alkyl, heteroaryl, heteroaryl-$C_{1-2}$-alkyl stand, which are optionally substituted, and optical isomers and racemates thereof.

5. Process for the preparation of the novel 1, 2, 3, 4, 4a, 5a, 8a, 8b-octahydro-6H-pyrrolo[3',4': 4,5]furo[3,2-b] pyridine-6,8(7H)-dione and/or 1, 2, 4a, 5a, 8a, 8b-hexahydro-6H-pyrrolo[3',4': 4,5]furo[3,2-b]-pyridine-6,8(7H)-dione derivatives of the general formulae (Ib) and (Ic) and salts thereof,

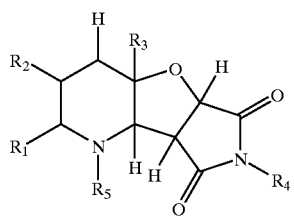

(Ib)

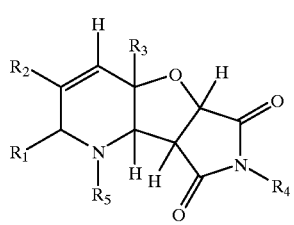

(Ic)

in which $R^1$, $R^2$, $R^3$, $R^4$ and $R^5$ have the meaning given under point 4, characterized in that the 4a, 5a, 8a, 8b-tetrahydro-6H-pyrrolo[3',4': 4,5]furo[3,2-b] pyridine-6,8(7H)-dione derivatives, obtainable, for example, according to process 3, of the general formula (Ia)

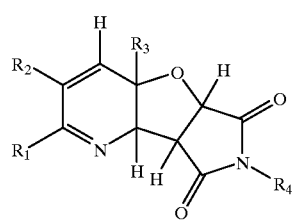

(Ia)

in which $R^1$, $R^2$, $R^3$ and $R^4$ have the meaning given under point 2, are hydrogenated in a first reaction step in the presence of suitable catalysts to form 1, 2, 3, 4, 4a, 5a, 8a, 8b-octahydro-6H-pyrrolo[3',4': 4,5]furo[3,2-n] pyridine-6,8(7H-dione and/or 1,2,4a, 5a, 8a, 8b-hexahydro-6H-pyrrolo[3',4': 4,5]furo[3,2-b] pyridine-6,8(7H)-dione derivatives of the general formula (Id) and (Ie)

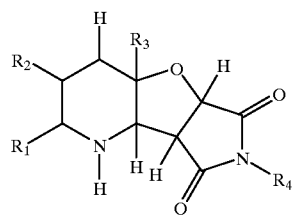

(Id)

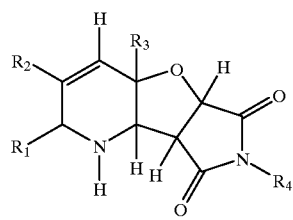

(Ie)

in which $R^1$, $R^2$, $R^3$ and $R^4$ have the meaning given further above, or

In order to selectively prepare the new derivatives of the general formula (Ie) and salts thereof, the derivatives of the general formula (Ia) are first reacted with methyl halides of the general formula (IV)

Me—Hal  (IV)

in which

Hal represents halogen, in particular fluorine, chlorine, bromine or iodine, if appropriate in the presence of diluents, and then the $N^1$-methylammonium halides formed, of the general formula (V)

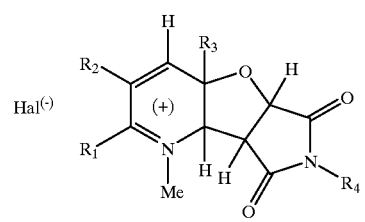

(V)

are hydrogenated in the presence of a suitable diluent, after which the resulting $N^1$-methyl derivative of the general formula (VI)

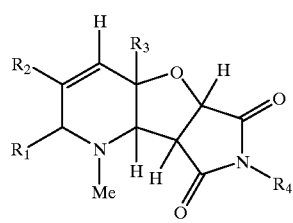

(VI)

in which $R^1$, $R^2$, $R^3$ and $R^4$ have the meaning mentioned further above, is demethylated at the $N^1$ atom to form (Ie) and then, in a second reaction step, the resulting 1, 2, 3, 4, 4a, 5a, 8a, 8b-octahydro-6H-pyrrolo[3',4': 4,5]furo[3,2-b]

pyridine-6,8(7H)-dione and/or 1, 2, 4a, 5a, 8a, 8b-hexahydro-6H-pyrrolo[3',4': 4,5]furo[3,2-b]-pyridine-6,8(7H)-dione derivatives of the general formulae (Id) and (Ie)

(Id)
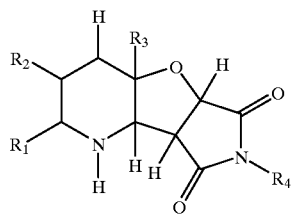

(Ie)
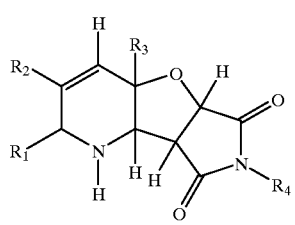

in which
$R^1$, $R^2$, $R^3$ and $R^4$ have the meaning given above,
a) are reacted with compounds of the general formula (VII)

$$R^5—E \qquad (VII)$$

in which
$R^5$ has the meaning given above, and
E represents an electron-withdrawing leaving group,
if appropriate in the presence of diluents and if appropriate in the presence of a basic reaction auxiliary, or
b) with compounds of the general formula (VIII)

(VIII)
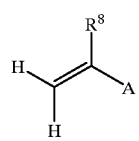

in which
A represents a suitable acceptor group, such as, for example, nitro, nitrile, carbamoyl or $R^{13}$—O—CO—, and
$R^8$ and $R^{13}$ have the meaning given under point 4, or in that
c) are reacted with an epoxide of the general formula (IX)

(IX)
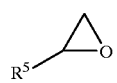

in which
$R^5$ has the meaning under point 4, if appropriate in the presence of a catalyst or in the presence of a basic reaction auxiliary, if appropriate in the presence of diluents, or d) are reacted with compounds of the general formula (X)

(X)
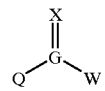

in which
G, Q and X have the meaning given under point 4, and
W represents a suitable leaving group, such as, for example, halogen, alkoxy, alkylthio or aryloxy, if appropriate in the presence of a catalyst, if appropriate in the presence of an acid-binding agent and if appropriate in the presence of diluents, or in that to prepare the novel 1, 2, 3, 4, 4a, 5a, 8a, 8b-octahydro-6H-pyrrolo[3',4': 4,5]furo[3,2-b]pyridine-6,8(7H)-dione and/or 1, 2, 4a, 5a, 8a, 8b-hexahydro-6H-pyrrolo[3',4': 4,5]furo[3,2-b]pyridine-6,8-(7H)-dione derivatives of the general formulae (Ib) and (Ic) and salts thereof, in which the group

represents carboxyl,
e) are reacted with a carboxylic acid anhydride of the general formula (XI)

$$(Q—C=O)_2O \qquad (XI)$$

in which
Q has the meaning given under point 4, if appropriate in the presence of a catalyst,
if appropriate in the presence of diluents, or
f) are reacted with amino sows derivatives of the general formula (XII)

(XII)
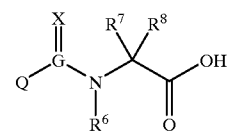

in which
G, Q, X, $R^6$, $R^7$ and $R^8$ have the meaning given under point 4, or carboxyl-activated derivatives thereof,
if appropriate in the presence of a catalyst, if appropriate in the presence of an acid-binding agent and if appropriate in the presence of diluents, or
g) are reacted with compounds of the general formulae (XIII) or (XIV)

$$R^{11}—N=C=X \qquad (XIII)$$

(XIV)
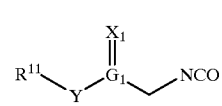

in which
the radicals $R^{11}$, $G^6$, X, Xl and Y have the meaning given under point 1, if appropriate in the presence of a catalyst, if appropriate in the presence of an acid-binding agent and if appropriate in the presence of diluents, or in that
to prepare the novel 1, 2, 3, 4, 4a, 5a, 8a, 8b-octahydro-6H-pyrrolo[3',4': 4,5]furo[3,2-b]pyridine-6,8(7H)-dione and/or 1, 2, 4a, 5a, 8a, 8b-hexahydro-6H-pyrrolo[3',4': 4,5]furo[3,2-b]pyridine-6,8(7H)-dione derivatives of the general formulae (Ib) and (Ic) and salts thereof,
in which the group

represents carboxyl and Y represents oxygen,
h) in a third reaction step are reacted with carbon dioxide and an alkali metal carbonate of the general formula (XV)

$$M_2CO_3 \quad (XV)$$

in which
M represents a monovalent alkali metal cation, preferably lithium, sodium, potassium or caesium, in particular potassium or caesium,
and then, in a fourth reaction step, the resulting alkali metal salts of compounds of the general formulae (XVI) and (XVII)

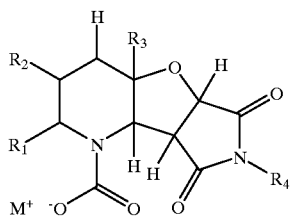

(XVI)

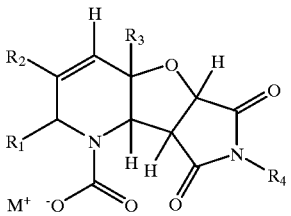

(XVII)

in which
the radicals $R^1$, $R^2$, $R^3$ and $R^4$ have the meaning given under point 4,
M represents one metal cation equivalent bonded in salt form,
are reacted with an alkylating agent of the formula (VIIa)

$$R^{11}-Hal \quad (VIIa)$$

in which
$R^{11}$ has the meaning given under point 4, and
Hal represents halogen, such as fluorine, chlorine, bromine or iodine,
if appropriate in the presence of a basic reaction auxiliary and if appropriate in the presence of diluents, or in that i) 1, 2, 3, 4, 4a, 5a, 8a, 8b-octahydro-6H-pyrrolo[3',4': 4,5]furo[3,2-b]-pyridine-6,8(7H)-dione and/or 1, 2, 4a, 5a, 8a, 8b-hexahydro-6H-pyrrolo [3',4,': 4,5] furo [3,2-b]pyridine-6,8(7H)-dione derivatives of the general formulae (Id) and (Ie)

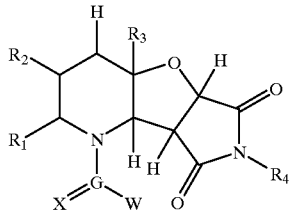

(If)

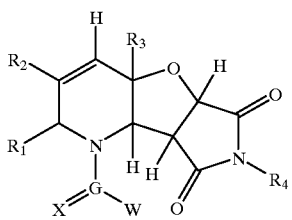

(Ig)

in which
the radicals $R^1$, $R^2$, $R^3$, $R^4$, G, W and X have the meaning given under point 4,
if appropriate in the presence of a catalyst, if appropriate in the presence of an acid-binding agent and if appropriate in the presence of diluents, are reacted with compounds of the general formula (XVIII)

$$R^{11}-Y-H \quad (XVIII)$$

in which
the radicals $R^{11}$ and Y have the meaning given above under point 4.
The general formula (I) provides a general definition of the 4a, 5a, 8a, 8b-tetrahydro-6H-pyrrolo[3',4': 4,5]furo[3,2-b]py-ridine-6,8(7H)-dione derivatives and salts thereof according to the invention.
The 4a, 5a, 8a, 8b-tetrahydro-6H-pyrrolo[3'4': 4,5]furo[3,2-b]py-ridine-6,8(7H)-dione derivatives and acid addition salts and metal salt complexes thereof according to the invention have a very good endoparasiticidal, in particular anthelmintic, action and can preferably be employed in the field of veterinary medicine.
Optionally substituted alkyl, by itself or as a constituent of a radical, in the general formulae denotes straight-chain or branched alkyl having preferably 1 to 6, in particular 1 to 4, carbon atoms. Examples which may be mentioned are optionally substituted methyl, ethyl, n-propyl, isopropyl, n-butyl, isobutyl, sec-butyl, tert-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylpropyl and 2-ethylbutyl. Methyl, ethyl, n-propyl, isopropyl, n-butyl, isobutyl, sec-butyl and tert-butyl may be mentioned as preferred.
Optionally substituted alkenyl, by itself or as a constituent of a radical, in the general formulae denotes straight-chain or branched alkenyl having preferably 1 to 6, in particular 1 to 4, carbon atoms. Examples which may be mentioned are optionally substituted vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-bute-nyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-diemethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-bute-nyl, 1-ethyl-3-butenyl, 2-ethyl-2-butenyl, 2-ethyl-3-butenyl, 1,1,2-trimethyl-2-prope-nyl, 1-ethyl-1-methyl-2-propenyl and 1-ethyl-2-methyl-2-propenyl. Optionally substituted ethenyl, 2-propenyl, 2-butenyl or 1-methyl-2-propenyl may be mentioned as preferred.

Optionally substituted alkinyl, by itself or as a constituent of a radical, in the general formulae denotes straight-chain or branched alkinyl having preferably 1 to 6, in particular 1 to 4, carbon atoms. Examples which may be mentioned are optionally substituted ethinyl, 2-propinyl, 2-butinyl, 3-butinyl, 1-methyl-2-propinyl, 2-pentinyl, 3-pentinyl, 4-pentinyl, 1-methyl-3-butinyl, 2-methyl-3-butinyl, 1-methyl-2-butinyl, 1,1-dimethyl-2-propinyl, 1-ethyl-2-propinyl, 2-hexinyl, 3-hexinyl, 4-hexinyl, 5-hexinyl, 1-methyl-2-pentinyl, 1-methyl-3-pentinyl, 1-methyl-4-pentinyl, 2-methyl-3-pentinyl, 2-methyl-4-pentinyl, 3-methyl-4-pentinyl, 4-methyl- 2-pentinyl, 1,1-dimethyl-2-b-butinyl, 1,1-dimethyl-3-butinyl, 1,2-dimethyl-3-butinyl, 2,2-dimethyl-3-butinyl, 1-ethyl-3-butinyl, 2-ethyl-3-butinyl and 1-ethyl-1-methyl-2-propinyl.

Optionally substituted ethinyl, 2-propinyl or 2-butinyl may be mentioned as preferred.

Optionally substituted cycloalkyl, by itself or as a constituent of a radical, in the general formulae denotes mono-, bi- and tricyclic cycloalkyl, prefer-ably having 3 to 10, in particular having 3, 5 or 7, carbon atoms. Examples which may be mentioned are optionally substituted cyclopropyl, cyclobutyl, cyclopentyl, cyclohexyl, cycloheptyl, cyclooctyl, bicyclo[2.2.1]heptyl, bicyclo[2.2.2]octyl and adamantyl.

Halogenoalkyl, by itself or as a constituent of a radical, in the general formulae contains 1 to 4, in particular 1 or 2, carbon atoms, and preferably 1 to 9, in particular 1 to 5, identical or different halogen atoms, preferably fluorine, chlorine and bromine, in particular fluorine and chlorine. Examples which may be mentioned are trifluoromethyl, trichloromethyl, chlorodifluoromethyl, dichlorofluoromethyl, chloromethyl, bromomethyl, 1-fluoroethyl, 2-fluoroethyl, 2,2-difluoroethyl, 2,2,2-trifluoroethyl, 2,2,2-trichloroethyl, 2-chloro-2,2-difluoroethyl, pentafluoroethyl and pentafluoro-tert-butyl.

Optionally substituted alkoxy, by itself or as a constituent of a radical, in the general formulae denotes straight-chain or branched alkoxy having preferably 1 to 6, in particular 1 to 4, carbon atoms. Examples which may be mentioned are optionally substituted methoxy, ethoxy, n-propoxy, isopropoxy, n-butoxy, iso-butoxy, sec-butoxy and tert-butoxy.

Optionally substituted halogenoalkoxy, by itself or as a constituent of a radical, in the general formulae denotes straight-chain or branched halogenoalkoxy having preferably 1 to 6, in particular 1 to 4, carbon atoms. Examples which may be mentioned are optionally substituted difluoromethoxy, trifluoromethoxy, trichloromethoxy, chlorodifluoromethoxy, 1-fluoroethoxy, 2-fluoroethoxy, 2,2-difluoroethoxy, 1,1,2,2-tetrafluoroethoxy, 2,2,2-trifluoroethoxy and 2-chloro-1,1,2-trifluoroethoxy.

Optionally substituted alkylthio, by itself or as a constituent of a radical, in the general formulae denotes straight-chain or branched alkylthio having pre-ferably 1 to 6, in particular 1 to 4, carbon atoms. Examples which may be mentioned are optionally substituted methylthio, ethylthio, n-propylthio, isopropylthio, n-butylthio, isobutylthio, sec-butylthio and tert-butylthio.

Optionally substituted halogenoalkylthio, by itself or as a constituent of a radical, in the general formulae denotes straight-chain or branched halogenoalkylthio having preferably 1 to 6, in particular 1 to 4, carbon atoms. Examples which may be mentioned are optionally substituted difluoromethylthio, trifluoromethylthio, trichloromethylthio, chlorodifluoromethylthio, 1-fluoroethylthio, 2-fluoroethylthio, 2,2-di-fluoroethylthio, 1,1,2,2-tetrafluoroethylthio, 2,2,2-trifluoroethylthio and 2-chloro-1,1,2-trifluoroethylthio.

Optionally substituted alkylcarbonyl, by itself or as a constituent of a radical, in the general formulae denotes straight-chain or branched alkylcarbonyl having preferably 1 to 6, in particular 1 to 4, carbon atoms. Examples which may be mentioned are optionally substituted methylcarbonyl, ethylcarbonyl, n-propylcarbonyl, isopropylcarbonyl, n-butylcarbonyl, isobutylcarbonyl, sec-bu-tyl-carbonyl and tert-butylcarbonyl.

Optionally substituted cycloalkylcarbonyl, by itself or as a constituent of a radical, in the general formulae denotes mono-, bi- and tricyclic cycloalkylcarbonyl, preferably having 3 to 10, in particular having 3, 5 or 7, carbon atoms. Examples which may be mentioned are optionally substi-tuted cyclopropylcarbonyl, cyclobutylcarbonyl, cyclopentylcarbonyl, cyclohexyl-carbonyl, cycloheptylcarbonyl, cyclooctylcarbonyl, bicyclo[2.2.1]-heptylcarbonyl, bicyclo[2.2.2]octylcarbonyl and adamantylcarbonyl.

Optionally substituted alkoxycarbonyl, by itself or as a constituent of a radical, in the general formulae denotes straight-chain or branched alkoxycarbonyl having prefer-ably 1 to 6, in particular 1 to 4, carbon atoms. Examples which may be mentioned are optionally substituted methoxycarbonyl, ethoxycarbonyl, n-propoxycarbonyl, isopropoxycarbonyl, n-butoxycarbonyl, Isobutoxycarbonyl, sec-butoxycarbonyl and tert-butoxycarbonyl.

Aryl is, for example, a mono-, di- or polynuclear aromatic radical, such as phenyl, naphthyl, tetrahydronaphthyl, indanyl, fluorenyl and the like, preferably phenyl or naphthyl.

Optionally substituted aryl in the general formulae preferably denotes optionally substituted phenyl or naphthyl, in particular phenyl.

Optionally substituted arylalkyl in the general formulae preferably denotes arylalkyl which is optionally substituted in the aryl part and/or alkyl and has preferably 6 or 10, in particular 8 carbon atoms in the aryl part (preferably phenyl or naphthyl, in particular phenyl) and preferably 1 to 4, in particular 1 or 2, carbon atoms in the alkyl part, it being possible for the alkyl part to be straight-chain or branched. Optionally substituted benzyl and phenylethyl may be mentioned as examples and as preferred.

Optionally substituted hetaryl, by itself or as a constituent of a radical, in the general formulae denotes 5- to 7-membered rings having preferably 1 to 3, in Iparticular 1 or 2, identical or different heteroaromatics. Heteroatoms in the heteroaromatics are oxygen, sulfur or nitrogen. Optionally substituted furyl, thienyl, pyrazolyl, imidazolyl, 1,2,3- and 1,2,4-triazolyl, isoxazolyl, thiazolyl, isothiazolyl, 1,2,3-, 1,3,4-, 1,2,4- and 1,2,5-oxadiazolyl, azepinyl, pyrrolyl, pyridyl, piperazinyl, pyridazinyl, pyrimidinyl, pyrazinyl, 1,3,5-, 1,2,4- and 1,2,3-triazinyl, 1,2,4-, 1,3,2-, 1,3,6- and 1,2,6-oxazinyl, oxepinyl, thiepinyl and 1,2,4-diazepinyl, may be mentioned as examples and as preferred.

The optionally substituted radicals of the general formulae can carry one or more, preferably 1 to 3, in particular 1 to 2, identical or different substituents. Substituents which may be mentioned as examples and as preferred are:

alkyl having preferably 1 to 4, in particular 1 to 2, carbon atoms, such as methyl, ethyl, n-propyl, isopropyl, n-butyl, isobutyl, sec-butyl and tert-butyl; alkoxy having preferably 1 to 4, in particular 1 to 2, carbon atoms, such as methoxy, ethoxy, n-propoxy, isopropoxy, n-butoxy, isobutoxy, sec-butoxy and tert-butoxy; alkylthio, such as methylthio, ethylthio, n-propylthio, isopropylthio, n-butylthio, isobutylthio, sec-butylthio and tert-butylthio; halogenoalkyl having preferably 1 to 4, in particular 1 to 2, carbon atoms and preferably 1 to 5, in particular 1 to 3, halogen atoms, the halogen atoms being identical or different and the halogen atoms being preferably fluorine, chlorine or bromine, in particular fluorine or chlorine, such as difluoromethyl, trifluoromethyl, trichloromethyl; hydroxyl; halogen, prefer-ably fluorine, chlorine, bromine and iodine, in particular fluorine and chlorine; cyano; nitro; amino; monoalkyl- and dialkylamino having preferably 1 to 4, in particular I or 2, carbon atoms per alkyl group, such as methylamino, methylethylamino, dimethyl-amino, n-propylamino, isopropylamino, methyl-n-butylami no; alkylcarbonyl radicals such as methylcarbonyl; alkoxycarbonyl having preferably 2 to 4, in particular 2 to 3, carbon atoms, such as methoxycarbonyl and ethoxycarbonyl; alkylsulfinyl having 1 to 4, in particular 1 to 2, carbon atoms; halogenosilfinyl having 1 to 4, in particular 1 to 2, carbon atoms and 1 to 5 halogen atoms, such as trifluoromethylsulfinyl; sulfonyl (—SO—OH); alkylsulfonyl having preferably 1 to 4, in particular 1 or 2, carbon atoms, such as methylsulfonyl and ethylsulfonyl; halogenoalkylsulfonyl having 1 to 4, in particular 1 to 2, carbon atoms and 1 to 5 halogen atoms, such as trifluoromethylsulfonyl, perfluoro-n-butylsulfonyl, perfluoro-isobutylsulfonyl; arylsulfonyl having preferably 6 or 10 aryl carbon atoms, such as phenylsulfonyl; acyl, aryl, aryloxy, hetaryl, hetaryloxy, which in their turn can carry one of the abovementioned substituents, and the formimino radical (—HC=N—O-alkyl).

Possible suitable cyclic amino groups are heteroaromatic or aliphatic ring systems having one or more nitrogen atoms as the heteroatom, in which the heterocyclic rings can be saturated or unsaturated, can be one ring system or several fused ring systems, and optionally contain further heteroatoms, such as nitrogen, oxygen and sulfur and the like. Cyclic amino groups can furthermore also denote a spiro ring or a bridged ring system. The number of atoms which form cyclic amino groups is not limited, for example in the case of a single-ring system, they comprise 3 to 8 atoms, and in the case of a three-ring system, they comprise 7 to 11 atoms.

Examples which may be mentioned of cyclic amino groups with saturated and unsaturated monocyclic groups with a nitrogen atom as the heteroatom are 1-azetidinyl, pyrrolidino, 2-pyrrolin-1-yl, 1-pyrrolyl, piperidino, 1,4-dihydropyridin-1-yl, 1,2,5,6-tetrahydropyridin-1-yl, homopiperidino; examples which may be mentioned of cyclic amino groups with saturated and unsaturated monocyclic groups with two or more nitrogen atoms as heteroatoms are 1-imidazolidinyl, 1-imidazolyl, 1-pyrazolyl, 1-triazolyl, 1-tetrazolyl, 1-piperazinyl, 1-homopiperazinyl, 1,2-dihydro-pyridazin-1-yl, 1,2-dihydro-pyrimidin-1-yl, perhydropyrimidin-1-yl and 1,4-diazacycloheptan-1-yl; examples which may be mentioned of cyclic amino groups with saturated and unsaturated monocyclic groups with one to three nitrogen atoms and one to two sulfur atoms as heteroatoms are thiazolidin-3-yl, isothiazolin-2-yl, thiomorpholino or dioxothiomorpholino; examples which may be mentioned of cyclic amino groups with saturated and unsaturated fused cyclic groups are indol-1-yl, 1,2-dihydrobenzimidazol-1-yl, perhydropyrrolo[1,2-a]pyrazin-2-yl; an example which may be mentioned of cyclic amino groups with spirocyclic groups is 2-azaspiro[4,5]decan-2-yl; an example which may be mentioned of cyclic amino groups bridged heterocyclic groups is 2-azabicyclo[2,2,1]heptan-7-yl.

Preferred compounds are those of the formula (I) and salts thereof

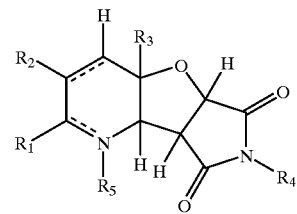

(I)

in which $R^1$ represent hydrogen, straight-chain or branched $C_{1-4}$-alkyl, in particular methyl, ethyl, propyl, isopropyl, isobutyl, sec-butyl, tert-butyl, $C_{3-6}$-cycloalkyl, in particular cyclopropyl, cyclobutyl, cyclopentyl, cyclohexyl, aryl, heteroaryl, which are optionally substituted, $R^1$ and $R^2$, together with the atoms to which they are bonded, represent a 5- or 6-membered ring, which is optionally substituted, $R^2$ and $R^3$ independently of one another represent hydrogen, straight-chain or branched branched $C_{1-4}$-alkyl, in particular methyl, ethyl, propyl, isopropyl, isobutyl, sec-butyl, tert-butyl, halogeno-$C_{1-4}$-alkyl, in particular chloromethyl, bromomethyl, difluoromethyl, trifluoromethyl or trichloromethyl, hydroxy-$C_{1-4}$-alkyl, in particular hydroxymethyl, $C_{1-4}$-alkanoyloxy-$C_{1-4}$-alkyl, in particular acetoxymethyl, $C_{1-2}$-alkoxyalkyl, in particular methoxymethyl, $C_{1-2}$-alkylthioalkyl, in particular methylthiomethyl, $C_{1-2}$-alkylsulfinyl-$C_{1-4}$-alkyl, in particular methylsulfinylmethyl, $C_{1-2}$-alkylsulfonyl-$C_{1-4}$-alkyl, in particular methylsulfonylmethyl, amino-$C_{1-4}$-alkyl, in particular aminomethyl, $C_{1-6}$-alkylamino-$C_{1-4}$-alkyl, in particular methylaminomethyl, $C_{1-6}$-dialkylamino-$C_{1-4}$-alkyl, in particular, dimethylaminomethyl, $C_{3-6}$-cycloalkylamino-$C_{1-2}$-alkyl, in particular morpholinomethyl, thiomorpholinomethyl, $C_{3-6}$-cycloalkyl, in particular cyclopropyl, cyclobutyl, $C_{1-4}$-alkoxycarbonyl, in particular methoxycarbonyl, ethoxycarbonyl, $R^4$ represents hydrogen, straight-chain or branched $C_{1-6}$-alkyl, in particular methyl, ethyl, propyl, isopropyl, isobutyl, sec-butyl, tert-butyl, pentyl, 1-methylbutyl, 2-methylbutyl, 3-methylbutyl, 1,2-di-methylpropyl, 1,1-dimethylpropyl, 2,2-dimethylpropyl, 1-ethyl-propyl, hexyl, 1-methylpentyl, halogeno-$C_{1-6}$-alkyl, in particular fluoromethyl, difluoromethyl, difluorochloromethyl, trifluoromethyl, trichloromethyl, 1-fluoroethyl, trifluoroethyl, 2-chloro-1,1,2-trifluoroethyl, hydroxy-$C_{1-6}$-alkyl, in particular hydroxymethyl, hydroxyethyl, 2-hydroxypropyl, $C_{1-4}$-alkanoyloxy-$C_{1-4}$-alkyl, in particular acetoxymethyl, acetoxyethyl, 2-acetoxypropyl, $C_{1-2}$-alkoxy-$C_{1-4}$alkyl, in particular methoxymethyl, methoxyethyl, 2-methoxypropyl, $C_{1-4}$-alkoxycarbonyl-$C_{1-4}$-alkyl, in particular methoxycarbonylmethyl, ethoxycarbonylmethyl, tert-butoxy-carbonylmethyl, methoxycarbonylethyl, ethoxycarbonylethyl, amino-$C_{1-6}$-alkyl, in particular aminomethyl, aminoethyl, 2-aminopropyl, $C_{1-6}$-alkylamino-$C_{1-6}$alkyl, in particular methylaminomethyl, methylaminoethyl, $C_{1-6}$-dialkylamino-$C_{1-6}$-alkyl, in particular di-methylaminomethyl, dimethylaminoethyl, $C_{1-6}$-trialkylammonium-$C_{1-6}$-alkyl halide, in particular trimethylaminomethylene iodide, tri-methylaminoethylene iodide, $C_{3-7}$-cycloalkylamino-$C_{1-4}$-alkyl, in particular N-pyrrolidinoethyl, N-morpholinoethyl, N-piperidinoethyl, N-thiomorpholinoethyl, $N^1$-($N^4$-methylpiperazino)-ethyl, $C_{2-6}$-alkenyl, in particular vinyl, 2-propenyl, 2-butenyl, 3-butenyl, 1-methyl-2-propenyl, 2-methyl-2-propenyl, 2-pentenyl, 1-methyl-2-butenyl, 2-methyl-2-butenyl, 3-methyl-2-butenyl, 1-methyl-3-butenyl, 1,1-dimethyl-2-propenyl, 1,2-dimethyl-2-propenyl, 1-ethyl-2-propenyl, 2-hexenyl 1,1-dimethyl-2-butenyl, 1,2-dimethyl-2 -butenyl, 1-ethyl-2-butenyl, $C_{2-6}$-alkinyl, in particular ethinyl, 2-propinyl, 2-butinyl, 3-butinyl, 1-methyl-2-propinyl, 2-pentinyl, 1-methyl-3-butinyl, 2-methyl-3-butinyl, 1,1-dimethyl-2-propinyl, 1-ethyl-2-propinyl, $C_{3-6}$-cycloalkyl in particular cyclopropyl, cyclobutyl, cyclopentyl, cyclohexyl, $C_{3-6}$-cycloalkyl-$C_{1-2}$-alkyl, in particular cyclopropylmethyl, cyclobutylmethyl, cyclopentylmethyl, cyclohexylmethyl, aryl, in particular phenyl, aryl-$C_{1-2}$-alkyl, in particular phenylmethyl, 1-phenylethyl, 2-phenylethyl, heteroaryl, in particular pyridyl or thiazolyl, N-morpholinyl, heteroaryl-$C_{1-2}$-alkyl, in particular pyridylmethyl and thiazolylmethyl, which radicals can optionally be substituted by radicals from the series consisting of halogen, in particular fluorine, chlorine, bromine or iodine, $C_{1-4}$-alkyl, in particular methyl, $C_{1-4}$-halogenoalkyl, in particular trifluoromethyl, trichloromethyl, amino, hydroxyl, $C_{1-4}$-alkoxy, in particular methoxy, $C_{1-2}$-alkylenedioxy, in particular methylenedioxy or ethylenedioxy, $C_{1-4}$-halogenoalkoxy, in particular trifluoromethoxy, difluoromethoxy, $C_{1-4}$-alkylthio, in particular methylthio, $C_{1-4}$-halogenoalkylthio, in particular trifluoromethylthio, $C_{1-4}$-alkylsulfonyl in particular methylsulfonyl, $C_{1-4}$-alkylamino, in particular methylamino, di-$C_{1-4}$-alkylamino, in particular dimethyl-amino, $C_{1-4}$-alkylcarbonyl, in particular methylcarbonyl, $C_{1-4}$-alkoxycarbonyl, in particular methoxycarbonyl, $R^5$ for hydrogen, straight-chain or branched $C_{1-6}$-alkyl, in particular methyl, ethyl, propyl, isopropyl, isobutyl, sec-butyl, tert-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, halogeno-$C_{1-6}$-alkyl, in particular fluoromethyl, difluoromethyl, difluorochloromethyl, trifluoromethyl, trichloromethyl, 1-fluoroethyl, trifluoroethyl, 2-chloro-1,1,2-trifluoroethyl, hydroxy-$C_{1-6}$-alkyl, in particular hydroxymethyl, hydroxyethyl, 2-hydroxypropyl, $C_{1-4}$-alkanoyloxy-$C_{1-4}$-alkyl, in particular acetoxymethyl, acetoxyethyl, 2-acetoxypropyl, $C_{1-2}$-alkoxy-$C_{1-4}$-alkyl, in particular methoxymethyl, methoxyethyl, 2-methoxypropyl, amino-$C_{1-6}$-alkyl, in particular aminomethyl, aminoethyl, 2-aminopropyl, $C_{1-6}$-alkylamino-$C_{1-6}$-alkyl, in particular methylaminomethyl, methylaminoethyl, $C_{1-16}$-dialkylamino-$C_{1-6}$-alkyl, in particular dimethylaminomethyl, dimethylaminoethyl, $C_{1-6}$-trialkylammonium-$C_{1-6}$-alkyl halide, in particular trimethyl-ammoniummethylene or trimethylammonium-ethylene iodide, $C_{3-7}$-cycloalkylamino-$C_{1-4}$-alkyl, in particular N-pyrrolidinoethyl, N-morpholinoethyl, N-piperidinoethyl, N-thiomorpholinoethyl, $N^1$-($N^4$-methylpiperazino)-ethyl, nitro-$C_{1-4}$-alkyl, in particular nitromethyl, 2-nitroethyl, 2-nitropropyl, cyano-$C_{1-4}$-alkyl, in particular cyanomethyl, 2-cyanoethyl, 2-cyanopropyl, $C_{1-4}$-alkoxycarbonyl-$C_{1-4}$-alkyl, in particular methoxycarbonylmethyl, 2-methoxycarbonylethyl, 2-ethoxycarbonylethyl, carbamoyl-$C_{1-4}$-alkyl, in particular carbamoylethyl, carboxyl-$C_{1-4}$-alkyl, in particular 2-carboxylethyl, $C_{2-6}$-alkenyl, in particular vinyl, 2-propenyl, 2-butenyl, 3-butenyl, 1-methyl-2-propenyl, 2-methyl-2-propenyl, 2-pentenyl, 1-methyl-2-butenyl, 2-methyl-2-butenyl, 3-methyl-2-butenyl, 1-methyl-3-butenyl, 1,1-dimethyl-2-propenyl, 1,2-dimethyl-2-propenyl, 1-ethyl-2-propenyl, 2-hexenyl, 1,1-dimethyl-2-butenyl, 1,2-dimethyl-2-butenyl, 1-ethyl-2-butenyl, $C_{2-6}$-alkinyl, in particular ethinyl, 2-propinyl, 2-butinyl, 3-butinyl, 1-methyl-2-propinyl, 2-pentinyl, 1-methyl-3-butinyl, 2-methyl-3-butinyl, 1,1-dimethyl-2-propinyl, 1-ethyl-2-propinyl, $C_{3-6}$-cycloalkyl, in particular cyclopropyl, cyclobutyl, cyclopentyl, cyclohexyl, $C_{3-6}$-cycloalkyl-$C_{1-4}$-alkyl, in particular cyclopropylmethyl, cyclobutylmethyl, cyclopentylmethyl, cyclohexylmethyl, $C_{1-4}$-alkoxydicarbonyl, in particular methoxydicarbonyl or ethoxydicarbonyl, aryl-$C_{1-2}$-alkyl, in particular phenylmethyl, heteroaryl, in particular pyridyl, pyrimidyl, pyrazinyl or thiazolyl, heteroaryl-$C_{1-2}$-alkyl, in particular pyridylmethyl and thiazolylmethyl, which radicals can optionally be substituted by radicals from the series consisting of halogen, in particular fluorine, chlorine, bromine or iodine, $C_{1-4}$-alkyl, in particular methyl, $C_{1-4}$-halogenoalkyl, in particular trifluoromethyl, trichloromethyl, amino, hydroxyl, $C_{1-4}$-alkoxy, in particular methoxy, $C_{1-2}$-alkylenedioxy, in particular methylenedioxy or ethylenedioxy, $C_{1-4}$-halogenoalkoxy, in particular trifluoromethoxy, difluoromethoxy, $C_{1-4}$-alkylthio, in particular methylthio, $C_{1-4}$-halogenoalkylthio, in particular trifluoromethylthio, $C_{1-4}$-alkylsulfonyl in particular methylsulfonyl $C_{1-4}$-alkylamino, in particular methylamino, di-$C_{1-4}$-alkylamino, in particular dimethylamino, $C_{1-4}$-alkylcarbonyl, in particular methylcarbonyl, $C_{1-4}$-alkoxycarbonyl, in particular methoxycarbonyl, methoxycarbonyl, can be substituted, or for a radical from the group consisting of $G^1$, $G^2$, $G^3$ and $G^4$

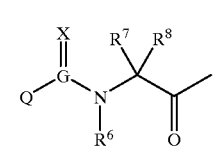

(G¹)

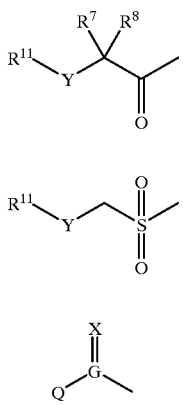

(G²)

(G³)

(G⁴)

in which

R represent hydrogen, straight-chain or branched $C_{1-6}$-alkyl, in particular methyl, ethyl, propyl, isopropyl, isobutyl, sec-butyl, tert-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, $C_{3-6}$-cycloalkyl, in particular cyclopropyl, cyclobutyl, cyclopentyl, cyclohexyl, aryl-$C_{1-2}$-alkyl, in particular phenylmethyl, heteroaryl-$C_{1-2}$-alkyl, in particular pyridylmethyl and thiazolylmethyl, which are optionally substituted, $R^6$ and $R^7$, together with the atoms to which they are bonded, represent a 5- or 6-membered ring, which optionally sulfur, can be interrupted and is optionally substituted by hydroxyl, stand, $R^7$ represents hydrogen, straight-chain or branched alkyl having up to 6 carbon atoms, in particular methyl, ethyl, propyl, isopropyl, sec-butyl, tert-butyl, hydroxy-$C_{1-2}$-alkyl, in particular hydroxymethyl, 1-hydroxyethyl, $C_{1-4}$-alkanoyloxy-$C_{1-4}$-alkyl, in particular acetoxy-methyl, 1-acetoxymethyl, $C_{1-4}$-alkoxy-$C_{1-4}$-alkyl, in particular methoxymethyl, 1-methoxyethyl, aryl-$C_{1-4}$-alkoxy-$C_{1-4}$-alkyl, in particular benzyloxymethyl, 1-benzyloxymethyl, mercapto-$C_{1-4}$-alkyl, in particular mercaptomethyl, $C_{1-4}$-alkylthio-$C_{1-4}$-alkyl, in particular methylsulfinylmethyl, $C_{1-4}$-alkylsulfonyl-$C_{1-4}$-alkyl, in particular methylsulfonylethyl, carboxy-$C_{1-4}$-alkyl, in particular carboxymethyl, carboxyethyl, $C_{1-4}$alkoxycarbonyl-$C_{1-4}$-alkyl, in particular methoxycarbonylmethyl, ethoxycarbonylmethyl, aryl-$C_{1-4}$-alkoxycarbonyl-$C_{1-4}$-alkyl, in particular benzyloxycarbonylmethyl, carbamoyl-$C_{1-4}$-alkyl, in particular carbamoylmethyl, carbamoyletlhyl, amino-$C_{1-4}$-alkyl, in particular aminopropyl, aminobutyl, $C_{1-4}$-alkylamino-$C_{1-4}$-alkyl, in particular methylaminopropyl, methylaminobutyl, $C_{1-4}$-dialkylamino-$C_{1-4}$-alkyl, in particular dimethylaminopropyl, dimethylaminobutyl, guanido-$C_{1-4}$-alkyl, in particular guanidopropyl, $C_{1-4}$-alkoxy-carbonylamino-$C_{1-4}$-alkyl, in particular tertbutylcarbonylamino-propyl, tert-butylcarbonylaminobutyl, alkenyl having up to 6 carbon atoms, in particular vinyl, 2-propenyl, 2-butenyl, 1-methyl-2-propenyl, $C_{3-6}$-cycloalkyl-$C_{1-2}$-alkyl, in particular cyclopropylmethyl, cyclobutylmethyl, cyclohexylmethyl, hetaryl-$C_{1-2}$-alkyl, in particular benzo[b]thien-1-yl-methyl, benzo[b]thien-3-yl, pyrid-2-yl-methyl, pyrid-3-yl-methyl, pyrid-4-yl-methyl, fur-2-yl-methyl, fur-3-yl-methyl, thien-2-yl-methyl, thien-3-yl-methyl, indol-3-yl-methyl, N-methyl-indol-3-yl-methyl, imidazol-4-yl-methyl, N-methylimidazol-4-yl-methyl, aryl-$C_{1-2}$-alkyl, in particular benzyl, which radicals can optionally be substituted by radicals from the series consisting of halogen, in particular fluorine, chlorine, bromine or iodine, hydroxyl, $C_{1-4}$-alkyl, in particular methyl or tert-butyl, $C_{1-4}$-halo-genoalkyl, in particular trifluoromethylethyl, difluoromethyl or trichloromethyl, $C_{1-4}$-alkoxy, in particular methoxy, ethoxy or tert-butyloxy, $C_{1-4}$-halogenoalkoxy, in particular trifluoromethoxy, difluoromethoxy, $C_{1-4}$-alkylthio, in particular methylthio, $C_{1-4}$-halogenoalkylthio, in particular trifluoromethylthio, $C_{1-2}$-alkylenedioxy, in particular methylenedioxy or ethylenedioxy, nitro, amino, $C_{1-4}$-alkylamino, in particular methylamino, $C_{1-4}$-dialkylamino, in particular dimethylamino, $C_{3-6}$-cycloalkylamino, in particular pyrrolidino, piperidino, $C_{3-6}$-cycloalkylthioamino, in particular thiomorpholino and dioxothiomorpholino, $C_{3-6}$-cycloalkyldiamino, in particular N-methylpiperazino, and $R^8$ represents hydrogen or methyl,

represents carboxyl, thiocarboxyl, —C=CH—NO₂, —C=CH—CN, —C=N—R⁹, sulfoxyl, sulfonyl, —P(O)—OR¹⁰ or P(S)—OR¹⁰.

$R^9$ represents hydrogen, hydroxyl, $C_{1-4}$-alkoxy, in particular methoxy, ethoxy, sec-butyloxy, $C_{1-4}$-alkylcarbonyl, in particular methylcarbonyl, ethylcarbonyl, $C_{1-4}$-halogenoalkylcarbonyl, in particular trifluoromethylcarbonyl, trichloromethylcarbonyl, $C_{1-4}$-alkylsulfonyl, in particular methylsulfonyl, ethylsulfonyl, propylsulfonyl, nitro or cyano, and $R^{10}$ represents hydrogen or $C_{1-4}$-alkyl, in particular methyl or ethyl, and Q represents straight-chain or branched $C_{1-4}$-alkyl, in particular methyl, ethyl, propyl, isopropyl, sec-butyl, tert-butyl, $C_{1-4}$-halogenoalkyl, in particular trifluoromethyl, trichloromethyl, chlorodifluoromethyl, dichlorofluoromethyl, 1-fluoroethyl, chloromethyl, bromomethyl, 1-fluoroethyl, 2,2,2-trifluoroethyl, 2,2,2-trichloroethyl, $C_{2-6}$-alkenyl, in particular vinyl, 2-propenyl, 1-methyl-2-propenyl and 2-butenyl, $C_{2-6}$-halogenoalkenyl, in particular difluorovinyl, dichlorovinyl, 2-chloro-2-propenyl, 2,3,3-trifluoro-2-propenyl, 2,3,3-trichloro-2-propenyl, 4,4-difluoro-3-butenyl, $C_{3-6}$-cycloalkyl, in particular cyclopropyl, cyclobutyl, cyclopentyl and cyclohexyl, hetaryl-$C_{1-2}$-alkyl, in particular pyridylmethyl and thiazolylmethyl, which radicals can optionally be substituted by radicals from the series consisting of halogen, in particular fluorine, chlorine, bromine or iodine, hydroxyl, $C_{1-4}$-alkyl, in particular methyl or tert-butyl $C_{1-4}$-halogenoalkyl, in particular trifluoromethyl, difluoromethyl or trichloromethyl, $C_{1-4}$-alkoxy, in particular methoxy, $C_{1-4}$-halogenoalkoxy, in particular trifluoromethoxy, difluoromethoxy, $C_{1-4}$-alkylthio, in particular methylthio, $C_{1-4}$-halogenoalkylthio, in particular trifluoromethylthio, nitro, amino, $C_{1-4}$-alkylamino, in particular methylamino, $C_{1-4}$-dialkylamino, in particular dimethylamino, or optionally represents a radical from the group consisting of $G^5$ and $G^6$

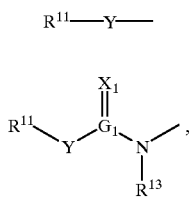           (G⁵)

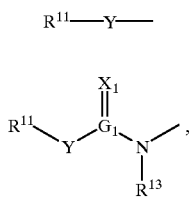           (G⁶)

in which

can denote carboxyl, thiocarboxyl or sulfonyl,

Y represents oxygen, sulfur or —NR$^{12}$,

R$^{11}$, in the case where Y represents nitrogen, a cyclic amino group linked via a nitrogen atom, in particular 1-azetidinyl, pyrrolidino, 2-pyrrolin-1-yl, 1-pyrrolyl, piperidino, 1,4-dihydropyridin-1-yl, 1-imidazolidinyl, 1-imidazolyl, 1-pyrazolyl, 1-triazolyl, 1-tetrazolyl, 1-piperazinyl, 1-homopiperazinyl, 1,2-dihydro-pyridazin-1-yl, 1,2-dihydropyrimidin-1-yl, perhydropyrimidin-1-yl, 1,4-diazacyclo-heptan-1-yl, thiazolidin-3-yl, isothiazolin-2-yl, morpholino, thiomorpholino, dioxothiomorpholino, which radicals can optionally be substituted by radicals from the series consisting of halogen, in particular fluorine, chlorine, bromine or iodine, $C_{1-4}$-alkyl, in particular methyl, hydroxy-$C_{1-4}$-alkyl, in particular hydroxymethyl, amino-$C_{1-4}$-alkyl, in particular aminomethyl, aminoethyl, $C_{1-4}$-monoalkylamino-$C_{1-4}$-alkyl, in particular methylaminomethyl, methylaminoethyl, $C_{1-4}$-dialkylamino-$C_{1-4}$-alkyl, in particular dimethylaminomethyl, dimethylaminoethyl, amino, hydroxyl, $C_{1-4}$-alkoxy, in particular methoxy, $C_{1-4}$-alkylcarbonyl, in particular methylcarbonyl, $C_{1-4}$-alkoxycarbonyl, in particular methoxycarbonyl, R$^{11}$ and R$^{12}$ independently of one another represent hydrogen, straight-chain or branched $C_{1-4}$-alkyl, in particular methyl, ethyl, propyl, isopropyl, sec-butyl, tert-butyl, carboxyl-$C_{1-4}$-alkyl, in particular carboxylmethyl, $C_{2-4}$-alkenyl, in particular vinyl, 2-propenyl, 1-methyl-2-propenyl and 2-butenyl, $C_{2-4}$-alkinyl, in particular ethinyl, 2-propinyl and 2-butinyl, $C_{3-6}$-cycloalkyl, in particular cyclopropyl, cyclobutyl, cyclopentyl and cyclohexyl, $C_{3-6}$-cycloalkyl-$C_{1-2}$-alkyl, in particular cyclopropylmethyl, cyclobutylmethyl, cyclopentylmethyl and cyclohexylmethyl, hetaryl, in particular pyridyl and thiazolyl, hetaryl-$C_{1-2}$-alkyl, in particular pyridylmethyl and thiazolylmethyl, which radicals can be optionally substituted by radicals from the series consisting of halogen, in particular fluorine, chlorine, bromine or iodine, $C_{1-4}$-alkyl, in particular methyl, hydroxy-$C_{1-4}$-alkyl, in particular hydroxymethyl, amino-$C_{1-4}$-alkyl, in particular aminomethyl, aminoethyl, $C_{1-4}$-monoalkylamino-$C_{1-4}$-alkyl, in particular methylaminomethyl, methylaminoethyl, $C_{1-4}$-dialkylamino$C_{1-4}$-alkyl, in particular dimethylaminomethyl, dime-thylaminoethyl, amino, hydroxyl, $C_{1-4}$-alkoxy, in particular methoxy, $C_{1-4}$-alkylcarbonyl, in particular methylcarbonyl, $C_{1-4}$-alkoxycarbonyl, in particular methoxycarbonyl, or R$^{11}$ and R$^2$, together with the adjacent N atom, represent a carbocyclic 5-, 6- or 7-membered ring system, or represent a 7 to 10-membered bicyclic ring system, which can optionally also be interrupted by oxygen, sulfur, sulfoxyl, sulfonyl, carbonyl, —N—O, —N═, —NR$^{14}$— or by quaternized nitrogen and is optionally substituted by $C_{1-4}$-alkyl, in particular methyl, hydroxy-$C_{1-4}$-alkyl, in particular hydroxymethyl, amino-$C_{1-4}$-alkyl, in particular aminomethyl, aminoethyl, $C_{1-4}$-monoalkylamino-$C_{1-4}$-alkyl, in particular methylaminomethyl, methylaminoethyl, $C_{1-4}$-dialkylamino-$C_{1-4}$-alkyl, in particular dimethylaminomethyl, dimethylaminoethyl, amino, hydroxyl, $C_{1-4}$-alkoxy, in particular methoxy, $C_{1-4}$-alkylcarbonyl, in particular methylcarbonyl, $C_{1-4}$-alkoxycarbonyl, in particular methoxycarbonyl, halogen, in particular fluorine, chlorine, bromine or iodine, or a radical from the groups G$^7$, G$^8$, G$^9$, G$^{10}$ and G$^{11}$

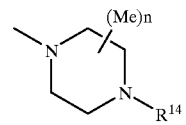           (G$^7$)

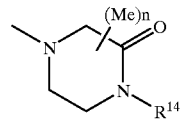           (G$^8$)

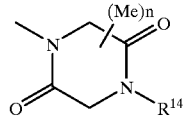           (G$^9$)

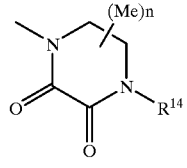           (G$^{10}$)

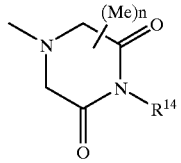           (G$^{11}$)

in which n can denote the numbers 0, 1, 2, 3 or 4,

R$^{13}$ represents hydrogen or $C_{1-4}$-alkyl, in particular methyl, ethyl, propyl, isopropyl, sec-butyl, tert-butyl, and R$^{14}$ represents hydrogen, straight-chain or branched $C_{1-6}$-alkyl, in particular methyl, ethyl, propyl, isopropyl, sec-butyl, tert-butyl, $C_{2-6}$-alkenyl, in particular vinyl, 2-propenyl, 1-methyl-2-propenyl and 2-butenyl, $C_{1-6}$-alkinyl, in particular ethinyl, 2-propinyl and 2-butinyl, $C_{3-6}$-cycloalkyl, in particular cyclopropyl, cyclobutyl, cyclopentyl and cyclohexyl, $C_{3-6}$-cycloalkyl-$C_{1-2}$-alkyl, in particular cyclopropylmethyl, cyclobutylmethyl, cyclopentylmethyl and cyclohexylmethyl, $C_{1-4}$-alkylcarbonyl, in particular methylcarbonyl, ethylcarbonyl, n-propylcarbonyl, isopropylcarbonyl, n-butylcarbonyl, isobutylcarbonyl, sec-butylcarbonyl, tert-butylcarbonyl, $C_{3-6}$-cycloalkylcarbonyl, in particular cyclopropylcarbonyl, cyclobutylcarbonyl, cyclopentylcarbonyl and cyclohexylcarbonyl, $C_{1-4}$-alkoxycarbonyl, in particular methoxycarbonyl, ethoxycarbonyl, n-propoxycarbonyl, iso-propoxycarbonyl, n-butoxycarbonyl, isobutoxycarbonyl, sec-butoxycarbonyl, tert-butoxycarbonyl, hydroxy-$C_{1-4}$-alkyl, in particular hydroxymethyl, hydroxyethyl, hydroxyethylsulfonylethyl, $C_{1-4}$-alkylamino, in particular methylamino, ethylamino, $C_{1-4}$-monoalkylamino-$C_{1-4}$-alkyl, in particular methylaminomethyl, methylaminoethyl, $C_{1-4}$-dialkylamino-$C_{1-4}$-alkyl, in particular dimethylaminomethyl, dimethylaminoethyl, dimethyl aminopropyl, $C_{3-7}$-cycloalkylamino-$C_{1-4}$-alkyl, in particular N-pyrrolidinoethyl, N-morpholinoethyl, N-piperidinoethyl, N-thio-morpholinoethyl, $N^1$-($N^4$-meth-yl-piperazino)-ethyl, $C_{3-6}$-cycloalkylaminocarbonyl-$C_{1-2}$-alkyl, in particular N-morpholinocarbonyl-methyl, cyano, aryl, in particular phenyl, aryl-$C_{1-2}$-alkyl, in particular phenylmethyl, hetaryl, in particular pyridyl or thiazolyl, heteroaryl-$C_{1-2}$-alkyl, in particular pyridylmethyl and thiazolyl-methyl, which radicals can optionally be substituted by radicals from the series consisting of halogen, in particular fluorine, chlorine, bromine or iodine, $C_{1-4}$-alkyl, in particular methyl, $C_{1-4}$-halogenoalkyl, in particular trifluoromethyl, trichloromethyl, amino, hydroxyl, $C_{1-4}$-alkoxy, in particular methoxy, $C_{1-2}$-alkylenedioxy, in particular methylenedioxy or ethylenedioxy, $C_{1-4}$-halogenoalkoxy, in particular trifluoromethoxy, difluoromethoxy, $C_{1-4}$-alkylthio, in particular methylthio, $C_{1-4}$-halogenoalkylthio, in particular trifluoromethylthio, $C_{1-4}$-alkylsulfonyl in particular methylsulfonyl, $C_{1-4}$-alkylamino, in particular methylamino, di-$C_{1-4}$-alkylamino, in particular dimethylamino, $C_{1-4}$-alkylcarbonyl, in particular methylcarbonyl, $C_{1-4}$-alkoxycarbonyl, in particular methoxycarbonyl, with the proviso for the compounds of the general formula (Ia), in the case where $R^1$ represents hydrogen, $R^2$ and $R^3$ represent methyl, $R^4$ represents radicals other than methyl, n-butyl, phenyl, 2-, 3- or 4-methylphenyl, 2-, 3- or 4-chlorophenyl, 2-, 3- or 4-fluorophenyl, 2-chloro, 4-fluorophenyl, 2-fluoro, 4-chlorophenyl, 3-chloro, 4-fluorophenyl, 2-, 3- or 4-nitrophenyl, 4-methoxyphenyl, and optical isomers and racemates thereof.

Particularly preferred compounds are those of the formula (I) and salts thereof

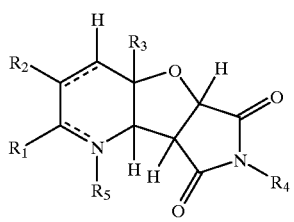

(I)

in which $R^1$ represent hydrogen, straight-chain or branched $C_{1-4}$-alkyl, in particular methyl, ethyl, propyl, isopropyl, isobutyl, sec-butyl, $C_{3-6}$-cycloalkyl, in particular cyclopropyl, $R^2$ represents hydrogen, straight-chain or branched branched $C_{1-4}$-alkyl, in particular methyl, ethyl, propyl, isopropyl, isobutyl, sec-butyl, tert-butyl, halogeno-$C_{1-4}$-alkyl, in particular chloromethyl, bromomethyl, hydroxy-$C_{1-4}$-alkyl, in particular hydroxymethyl, $C_{1-4}$-alkanoyloxy-$C_{1-4}$-alkyl, in particular acetoxymethyl, $C_{1-2}$-alkoxyalkyl, in particular methoxymethyl, $C_{1-2}$-alkylthioalkyl, in particular methyl-thiomethyl, $C_{1-2}$-alkylsulfinyl-$C_{1-4}$-alkyl, in particular methyl-sulfinylmethyl, $C_{1-2}$-alkylsulfonyl-$C_{1-4}$-alkyl, in particular methyl-sulfonylmethyl, $C_{1-6}$-alkylamino-$C_{1-4}$-alkyl, in particular methyl-aminomethyl, $C_{1-6}$-dialkylamino-$C_{1-4}$-alkyl, in particular dimethylaminomethyl, $C_{3-6}$-cycloalkylamino-$C_{1-2}$-alkyl, in particular morpholinomethyl, thiomorpholinomethyl, $C_{1-4}$-alkoxycarbonyl, in particular methoxycarbonyl, ethoxycarbonyl, $R^3$ represents hydrogen, straight-chain or branched $C_{1-4}$-alkyl, in particular methyl, ethyl, propyl, isopropyl, isobutyl, sec-butyl, tert-butyl, $R^4$ represents straight-chain or branched $C_{1-6}$-alkyl, in particular methyl, ethyl, propyl, isopropyl, isobutyl, sec-butyl, tert-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, halogeno-$C_{1-6}$-alkyl, in particular fluoromethyl, difluoromethyl, fluoroethyl, $C_{1-4}$-alkoxycarbonyl-$C_{1-4}$-alkyl, in particular methoxycarbonylmethyl, ethoxycarbonylmethyl, tert-butoxycarbonylmethyl, $C_{3-7}$-cycloalkylamino-$C_{1-4}$-alkyl, in particular N-pyrrolidinoethyl, N-morpholinoethyl, N-piperidinoethyl, N-thiomorpholinoethyl, $C_{2-6}$-alkenyl, in particular 2-propenyl, 2-butenyl, $C_{3-6}$-cycloalkyl in particular cyclopropyl, cyclobutyl, cyclopentyl, cyclohexyl, $C_{3-6}$-cycloalkyl-$C_{1-2}$-alkyl, in particular cyclopropylmethyl, cyclobutylmethyl, aryl-$C_{1-2}$-alkyl, in particular phenylmethyl, 1-phenylethyl, 2-phenylethyl, heteroaryl, in particular pyridyl or thiazolyl, N-morpholinyl, hetaryl-$C_{1-2}$-alkyl, in particular pyridylmethyl and thiazolylmethyl, which radicals can optionally be substituted by radicals from the series consisting of halogen, in particular fluorine, chlorine, bromine or iodine, $C_{1-4}$-alkyl, in particular methyl, $C_{1-4}$-halogenoalkyl, in particular trifluoromethyl, trichloromethyl, amino, hydroxyl, $C_{1-4}$-alkoxy, in particular methoxy, $C_{1-2}$-alkylenedioxy, in particular methylenedioxy or ethylenedioxy, $C_{1-4}$-halogenoalkoxy, in particular trifluoromethoxy, difluoromethoxy, $C_{1-4}$-alkylthio, in particular methylthio, $C_{1-4}$-halogenoalkylthio, in particular trifluoromethylthio, $C_{1-4}$-alkylsulfonyl in particular methylsulfonyl, $C_{1-4}$-alkylamino, in particular methylamino, di-$C_{1-4}$-alkylamino, in particular dimethylamino, $C_{1-4}$-alkylcarbonyl, in particular methylcarbonyl, $C_{1-4}$-alkoxycarbonyl, in particular methoxycarbonyl, $R^5$ for hydrogen, straight-chain or branched $C_{1-6}$-alkyl, in particular methyl, ethyl, propyl, isopropyl, isobutyl, sec-butyl, $C_{1-4}$-alkanoyloxy-$C_{1-4}$-alkyl, in particular methoxycarbonylmethyl, ethoxycarbonylmethyl, methoxycarbonylethyl, ethoxycarbonylethyl, tert-butoxycarbonylmethyl, amino-$C_{1-6}$-alkyl, in particular amino-methyl, aminoethyl, $C_{1-6}$-alkylamino-$C_{1-6}$-alkyl, in particular methylaminomethyl, methylaminoethyl, $C_{1-6}$-dialkylamino-$C_{1-6}$-alkyl, in particular dimethylaminomethyl, dimethylaminoethyl, $C_{1-6}$-trialkylammonium-$C_{1-6}$-alkyl halide, in particular trimethylammoniummethylene or trimethylammoniumethylene iodide, $C_{3-7}$-cycloalkylamino-$C_{1-4}$-alkyl, in particular N-pyrrolidinoethyl, N-morpholinoethyl, N-piperidinoethyl, N-thiomorpholinoethyl, N'-($N^4$- methyl-piperazino)-ethyl, nitro-$C_{1-4}$-alkyl, 2-nitroethyl, cyano-$C_{1-4}$-alkyl, in particular 2-cyanoethyl, $C_{1-4}$-alkoxycarbonyl-$C_{1-4}$-alkyl, in particular 2-methoxycarbonylethyl, $C_{2-6}$-alkenyl, in particular 2-propenyl, $C_{2-6}$-alkinyl, in particular 2-propinyl, $C_{1-4}$-alkoxydicarbonyl, in particular methoxydicarbonyl or ethoxydicarbonyl, heteroaryl, in particular pyridyl, pyrimidyl, pyrazinyl or thiazolyl, heteroaryl-$C_{1-2}$-alkyl, in particular pyridyl, pyrimidyl, pyrazinyl or thiazolyl, heteroaryl-$C_{1-2}$-alkyl, in particular pyridylmethyl and thiazolylmethyl, which radicals can optionally be substituted by radicals from the series consisting of halogen, in particular fluorine, chlorine, bromine or iodine, $C_{1-4}$-alkyl, in particular methyl, $C_{1-4}$-halogenoalkyl, in particular trifluoromethyl, trichloromethyl, amino, hydroxyl, $C_{1-4}$-alkoxy, in particular methoxy, $C_{1-2}$-alkylenedioxy, in particular methylenedioxy or ethylenedioxy, $C_{1-4}$-halogenoalkoxy, in particular trifluoromethoxy, difluoromethoxy, $C_{1-4}$-alkylthio, in particular methylthio, $C_{1-4}$-halogenoalkylthio, in particular trifluoromethylthio, $C_{1-4}$-alkylsulfonyl, in particular methylsulfonyl, $C_{1-4}$-alkylamino, in particular methylamino, di-$C_{1-4}$-alkylamino, in particular dimethylamino, $C_{1-4}$-alkylcarbonyl, in particular methylcarbonyl, $C_{1-4}$-alkoxycarbonyl, in particular methoxycarbonyl, methoxycarbonyl, can be substituted or for a radical from the group consisting of $G^1$, $G^2$, $G^3$ and $G^4$

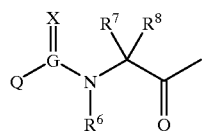
(G¹)

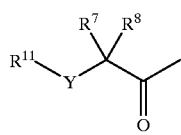
(G²)

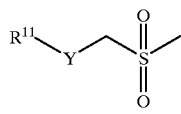
(G³)

(G⁴)

in which $R^6$ represents hydrogen, straight-chain or branched $C_{1-6}$-alkyl, in particular methyl, ethyl, $C_{3-6}$-cycloalkyl, in particular cyclopropyl, $R^6$ and $R^7$, together with the atoms to which they are bonded, represent a 5- or 6-membered ring, which optionally sulfur, can be interrupted and is optionally substituted by hydroxyl, stand, $R^7$ for hydrogen, straight-chain or branched alkyl having up to 6 carbon atoms, in particular methyl, ethyl, propyl, isopropyl, sec-butyl, $R^8$ represents hydrogen or methyl,

represents carboxyl, —C=CH—$NO_2$, —C=CH—CN, —C=N—$R^9$, sulfonyl, $R^9$ represents $C_{1-4}$-halogenoalkylcarbonyl, in particular trifluoromethylcarbonyl, trichloromethylcarbonyl, $C_{1-4}$-alkylsulfonyl, in particular methylsulfonyl, ethylsulfonyl, nitro or cyano, and Q represents a radical from the group consisting of $G^5$ and $G^6$

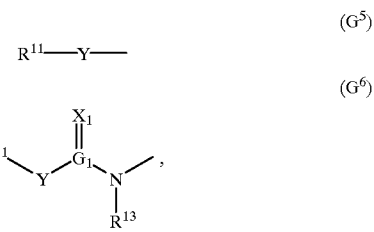
(G⁵)
(G⁶)

in which

can denote carboxyl or sulfonyl,

Y represents oxygen or NR $R^{11}$, in the case where Y represents nitrogen, a cyclic amino group which is linked via a nitrogen atom, in particular pyrrolidino, 2-pyrrolin-1-yl, 1-pyrrolyl, piperidino, 1,4-dihydropyridin-1-yl, 1-piperazinyl, 1-homopiperazinyl, morpholino, thiomorpholino, dioxothio-morpholino, which radicals can optionally be substituted by radicals from the series consisting of halogen, in particular fluorine, chlorine, bromine or iodine, $C_{1-4}$-alkyl, in particular methyl, hydroxy-$C_{1-4}$-alkyl, in particular hydroxymethyl, amino-$C_{1-4}$-alkyl, in particular aminomethyl, aminoethyl, $C_{1-4}$-monoalkylamino $C_{1-4}$-alkyl, in particular methylaminomethyl, methylaminoethyl, $C_{1-4}$-di-alkyl-amino-$C_{1-4}$-alkyl, in particular dimethylaminomethyl, dimethylaminoethyl, amino, hydroxyl, $C_{1-4}$-alkoxy, in particular methoxy, $C_{1-4}$-alkylcarbonyl, in particular methylcarbonyl, $C_{1-4}$-alkoxycarbonyl, in particular methoxycarbonyl, $R^{11}$ and $R^{12}$ independently of one another represent hydrogen, straight-chain or branched $C_{1-4}$-alkyl, in particular methyl, ethyl, propyl, isopropyl, sec-butyl, carboxyl-$C_{1-4}$-alkyl, in particular carboxylmethyl, $C_{1-4}$-alkenyl, in particular vinyl, 2-propenyl, 1-methyl-2-propenyl, $C_{1-4}$-alkinyl, in particular ethinyl, 2-propinyl, $C_{3-6}$-cycloalkyl, in particular cyclopropyl, heteroaryl-$C_{1-2}$-alkyl, in particular pyridylmethyl and thiazolylmethyl, which radicals can optionally be substituted by radicals from the series consisting of halogen, in particular fluorine, chlorine, bromine or iodine, $C_{1-4}$-alkyl, in particular methyl, hydroxy-$C_{1-4}$-alkyl, in particular hydroxymethyl, amino-$C_{1-4}$-alkyl, in particular aminomethyl, aminoethyl, $C_{1-4}$-monoalkylamino-$C_{1-4}$-alkyl, in particular methylaminomethyl, methylaminoethyl, $C_{1-4}$-dialkylamino-$C_{1-4}$-alkyl, in particular dimethylaminomethyl, dimethylaminoethyl, amino, hydroxyl, $C_{1-4}$-alkoxy, in particular methoxy, $C_{1-4}$-alkylcarbonyl, in particular methylcarbonyl, $C_{1-4}$-alkoxycarbonyl, in particular methoxycarbonyl, or $R^{11}$ and $R^2$, together with the adjacent N atom, represent a carbocyclic 5-, 6- or 7-membered ring system, or represent a 7 to 10-membered bicyclic ring system, which can optionally also be interrupted by oxygen, sulfur, sulfoxyl, sulfonyl, carbonyl, —N—O, —N=, —$NR^{14}$— or by quaternized nitrogen and is optionally substituted by $C_{1-4}$-alkyl, in particular methyl, hydroxy-$C_{1-4}$-alkyl, in particular hydroxymethyl, amino-$C_{1-4}$-alkyl, in particular aminomethyl, aminoethyl, $C_{1-4}$-monoalkylamino-$C_{1-4}$-alkyl, in particular methylaminomethyl, methylaminoethyl, $C_{1-4}$-dialkylamino-$C_{1-4}$-alkyl, in particular dimethylaminomethyl, dimethylaminoethyl, amino, hydroxyl, $C_{1-4}$-alkoxy, in particular methoxy, $C_{1-4}$-alkylcarbonyl, in particular methylcarbonyl, $C_{1-4}$-alkoxycarbonyl, in particular methoxycarbonyl, halogen, in particular fluorine, chlorine, bromine or iodine, or a radical from the groups $G^7$, $G^8$, $G^9$, $G^{10}$ and $G^{11}$

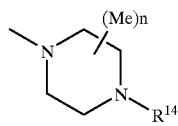

(G$^7$)

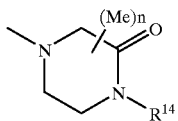

(G$^8$)

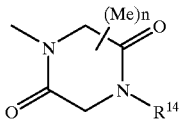

(G$^9$)

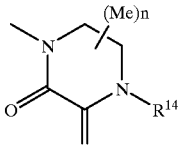

(G$^{10}$)

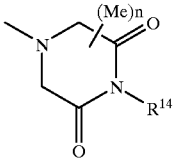

(G$^{11}$)

in which n can denote the numbers 0, 1, 2 or 3, $R^{13}$ represents $C_{1-4}$-alkyl, in particular methyl or ethyl, and $R^{14}$ represents hydrogen, straight-chain or branched $C_{1-6}$-alkyl, in particular, methyl, ethyl, $C_{2-6}$-alkenyl, in particular vinyl, 2-propenyl, $C_{2-6}$-alkinyl, in particular 2-propinyl, $C_{3-6}$-cycloalkyl, in particular cyclopropyl, $C_{1-4}$-alkoxycarbonyl, in particular methoxycarbonyl, ethoxycarbonyl, tert-butoxycarbonyl, hydroxy-$C_{1-4}$-alkyl, in particular hydroxymethyl, hydroxyethyl, hydroxyethylsulfonylethyl, $C_{1-4}$-alkylamino, in particular methylamino, ethylamino, $C_{1-4}$-dialkylamino-$C_{1-4}$-alkyl, in particular dimethylaminomethyl, dimethylaminoethyl, $C_{3-7}$-cycloalkyl amino-$C_{1-4}$-alkyl, in particular N-pyrrolidinoethyl, N-morpholinoethyl, N-piperidinoethyl, N-thiomorpholinoethyl, $N^1$-($N^4$-methylpiperazino)-ethyl, $C_{3-6}$-cycloalkylaminocarbonyl-$C_{1-2}$-alkyl, in particular N-morpholinocarbonylmethyl, cyano, aryl, in particular phenyl, aryl-$C_{1-2}$-alkyl, in particular phenylmethyl, hetaryl, in particular pyridyl or thiazolyl, heteroaryl-$C_{1-2}$-alkyl, in particular pyridylmethyl and thiazolylmethyl, which radicals can optionally be substituted by radicals from the series consisting of halogen, in particular fluorine, chlorine, bromine or iodine, $C_{1-4}$-alkyl, in particular methyl, $C_{1-4}$-halogenoalkyl, in particular trifluoromethyl, trichloromethyl, amino, hydroxyl, $C_{1-4}$-alkoxy, in particular methoxy, $C_{1-2}$-alkylenedioxy, in particular methylenedioxy or ethylenedioxy, $C_{1-4}$-halogenoalkoxy, in particular trifluoromethoxy, difluoromethoxy, $C_{1-4}$-alkylthio, in particular methylthio, $C_{1-4}$-halogenoalkylthio, in particular trifluoro-methylthio, $C_{1-4}$-alkylsulfonyl, in particular methylsulfonyl, $C_{1-4}$-alkylamino, in particular methylamino, di-$C_{1-4}$-alkylamino, in particular dimethylamino, $C_{1-4}$-alkylcarbonyl, in particular methylcarbonyl, $C_{1-4}$-alkoxycarbonyl, in particular methoxycarbonyl, with the proviso for the compounds of the general formula (Ia), in the case where $R^1$ represents hydrogen, $R^1$ and $R^3$ represent methyl, $R^4$ represents radicals other than methyl or n-butyl, and optical isomers or racemates thereof.

Especially preferred compounds are those of the formula (I) and salts thereof

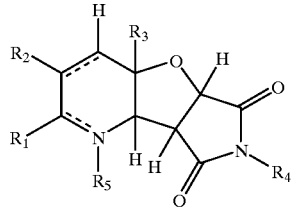

(I)

in which $R^1$ represents hydrogen, $R^2$ represents straight-chain or branched branched $C_{1-4}$-alkyl, in particular methyl, ethyl, $R^3$ represents methyl, $R^4$ represent straight-chain or branched $C_{1-6}$-alkyl, in particular methyl, ethyl, propyl, isopropyl, isobutyl, sec-butyl, n-butyl, $C_{3-6}$-cycloalkyl, in particular cyclopropyl, cyclobutyl, cyclopentyl, $C_{3-6}$-cycloalkyl-$C_{1-2}$-alkyl, in particular cyclopropylmethyl, phenyl-$C_{1-2}$-alkyl, in particular phenylmethyl, 2-phenylethyl, phenyl, N-morpholinyl, hetero-$C_{1-2}$-alkyl, in particular 2-chloro-pyrid-5-yl-methyl, morpholinylethyl and chlorothiazol-5-yl-methyl, where the phenyl or hetaryl radicals can be substituted by halogen, methyl, halogenomethyl, phenyl, phenoxy, $C_{1-4}$-alkylphenyl, $C_{1-4}$-halogeno-alkylphenoxy, $C_{1-4}$-alkylphenoxy, $R^5$ represent hydrogen, straight-chain or branched $C_{1-6}$-alkyl, in particular methyl, ethyl, cyano-$C_{1-4}$-alkyl, in particular 2-cyanoethyl, $C_{1-4}$-alkanoyloxy-$C_{1-4}$-alkyl, in particular methoxycarbonylmethyl, $C_{1-6}$-alkenyl, in particular 2-propenyl, $C_{2-6}$-alkinyl, in particular 2-propinyl, $C_{1-4}$-alkoxydicarbonyl, in particular methoxydicarbonyl or ethoxydicarbonyl, heteroaryl-$C_{1-2}$-alkyl, in particular 5-chloropyrid-2-yl-methyl and chloro-thiazol-5-yl-methyl, or a radical from the group consisting of $G^1$, $G^2$, $G^3$ and $G^4$

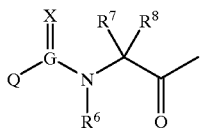
(G¹)

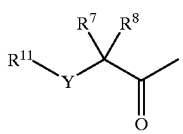
(G²)

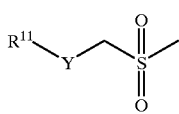
(G³)

(G⁴)

in which
$R^6$ represent hydrogen or methyl,
$R^7$ represent hydrogen, straight-chain or branched alkyl having up to 6 carbon atoms, in particular methyl or ethyl,
$R^8$ for hydrogen,

represents carboxyl or sulfonyl,
Q represents a radical from the group consisting of $G^5$ and $G^6$ (G⁵)
R¹¹—Y—

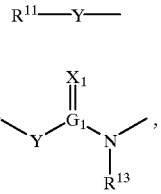
(G⁶)

in which

can denote carboxyl or sulfonyl,
Y represents oxygen or —NR¹²,
$R^{11}$, in the case where Y represents nitrogen, denotes a cyclic amino group which is linked via a nitrogen atom, in particular pyrrolidino, 1-pyrrolyl, piperidino, morpholino, thiomorpholino, dioxothiomorpholino,
$R^{11}$ and $R^{12}$ independently represent straight-chain or branched $C_{1-4}$-alkyl, in particular methyl, ethyl, propyl, isopropyl, sec-butyl, $C_{1-4}$-alkenyl, in particular vinyl, 2-propenyl, 1-methyl-2-propenyl, $C_{2-4}$-alkinyl, in particular ethinyl, 2-propinyl, $C_{3-6}$-cycloalkyl, in particular cyclopropyl, heteroaryl-$C_{1-2}$-alkyl, in particular 5-chloro-pyrid-2-yl-methyl and chlorothiazol-5-yl-methyl, or
$R^{11}$ and $R^{12}$, together with the adjacent N atom, represent a carbocyclic 5-, 6- or 7-membered ring system, which can optionally also be interrupted by oxygen, sulfur, sulfonyl, carbonyl, —N=, —NR⁴— or by quaternized nitrogen and optionally by $C_{1-4}$-alkyl, in particular methyl, thyl, hydoxy-$C_{1-4}$-alkyl, in particular hydroxymethyl, amino-$C_{1-4}$-dialkylamino-$C_{1-4}$-alkyl, in particular dimethylaminomethyl, hydroxyl, $C_{1-4}$-alkoxycarbonyl, in particular methoxycarbonyl, or a radical from the groups consisting of $G^7$, $G^8$, $G^9$, $G^{10}$ and $G^{11}$

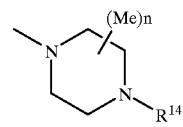
(G⁷)

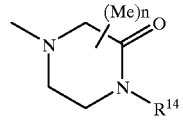
(G⁸)

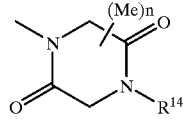
(G⁹)

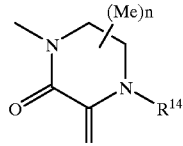
(G¹⁰)

(G¹¹)

in which
n can denote the numbers 0, 1 or 2,
$R^{13}$ represents $C_{1-4}$-alkyl, in particular methyl, and
$R^{14}$ represents straight-chain or branched $C_{1-6}$-alkyl, in particular methyl, $C_{2-6}$-alkenyl, in particular vinyl, 2-propenyl, $C_{2-6}$-alkinyl, in particular 2-propinyl, $C_{3-6}$-cycloalkyl, in particular cyclopropyl, $C_{1-4}$-alkoxycarbonyl, in particular methoxycarbonyl, hydroxy-$C_{1-4}$-alkyl, in particular hydroxyethyl, hydroxyethylsulfonylethyl, $C_{1-4}$-alkyl-amino, in particular methylamino, ethylamino, $C_{1-4}$-dialkylamino-$C_{1-4}$-alkyl, in particular dimethylaminoethyl, $C_{3-7}$- cycloalkylamino-$C_{1-4}$-alkyl, in particular N-morpholinoethyl, N-piperidinoethyl, $C_{3-6}$-cycloalkylaminocarbonyl-$C_{1-2}$-alkyl, in particular N-morpholino-carbonylmethyl,
with the proviso for the compounds of the general formula (Ia), in the case where
$R^1$ represents hydrogen,
$R^2$ and $R^3$ represent methyl,
$R^4$ represents radicals other than methyl or n-butyl,
and optical isomers and racemates thereof.

The compound of the general formula (I) and salts thereof to be used according to the invention furthermore contain one or more chirality centres and can thus be present as pure stereoisomers or in the form of various enantiomer and diastereo-isomer mixtures, which can be separated in a manner known per se if necessary. The invention therefore relates both to the pure enan-tiomers and diastereomers and to mixtures thereof for controlling endoparasites, in particular in the field of medicine and veterinary medicine.

Preferably, however, the optically active, stereoisomeric forms of the compounds of the general formula (I) and salts thereof are used according to the invention.

Suitable salts of the compounds of the general formula (I) which may be mentioned are the customary non-toxic salts, i.e. salts with various bases and salts with added acids. Salts which may be mentioned as preferred are those with inorganic, bases, such as alkali metal salts, for example sodium, potassium or caesium salts, alkaline earth metal salts, for example calcium or magnesium salts, ammonium salts, salts with organic bases and with organic amines, for example tri ethyl ammonium, pyridinium, picolinium, ethanolammonium, tri ethanol ammonium, dicyclohexylammonium or N,N'-dibenzylethylenedi-ammonium salts, salts with inorganic acids, for example hydrochlorides, hydrobromides, dihydrosulfates or trihydrophosphates, salts with organic carboxylic acids or organic sulfonic acids, for example formates, acetates, trifluoroacetates, maleates, tartrates, methanesulfonates, benzenesulfonates or para-toluenesulfonates, salts with basic amino acids or acid amino acids, for example arginates, aspartates or glutamates.

Examples of the novel compounds according to the invention are listed in Tables 1 to 52.

TABLE 1

(Ib-1)

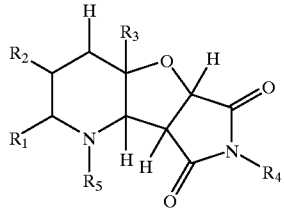

Compounds of Table 1 correspond to the general formula (Ib-1), in which $R^1$ = —H, $R^2$, $R^3$, $R^4$ = -methyl, $R^5$ is as listed below:

| Compound No. | $R^5$ |
|---|---|
| 1 | —SO$_2$—Me |
| 2 | —SO$_2$—Et |
| 3 | —SO$_2$-iPr |
| 4 | —SO$_2$—CH$_2$—Cl |
| 5 | —CO—Me |
| 6 | —CO—CH$_2$—Cl |
| 7 | —CO—CF$_3$ |
| 8 | —CO—CCl$_3$ |

TABLE 1-continued (Ib-1)

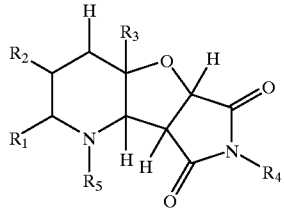

Compounds of Table 1 correspond to the general formula (Ib-1), in which $R^1$ = —H, $R^2$, $R^3$, $R^4$ = -methyl, $R^5$ is as listed below:

| Compound No. | $R^5$ |
|---|---|
| 9 | —CO-cyclopropyl |
| 10 | —CO—O—Me |
| 11 | —CH$_2$—C≡CH |
| 12 | —CO—NMe—CO—NMe$_2$ |
| 13 | —CO—NMe—CO—NEt$_2$ |
| 14 | -cyclopropyl |
| 15 | —CO—O—(CH$_2$)$_2$—CF=CF$_2$ |
| 16 | pyrazin-2-yl- |
| 17 | —CS—NMe$_2$ |
| 18 | —CO—NMe$_2$ |
| 19 | 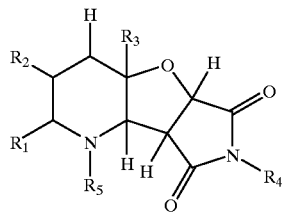 |
| 20 | 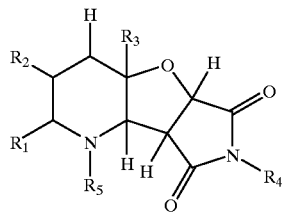 |
| 21 | 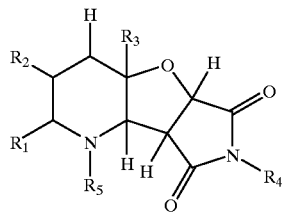 |
| 22 | 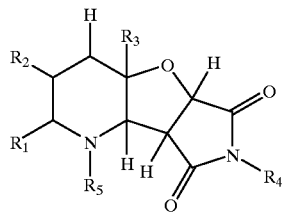 |
| 23 | —CH$_2$—C≡N |
| 24 | —PO(O—Et)$_2$ |
| 25 | —CO—CH$_2$—NH$_2$ |
| 26 | —CO—CH$_2$—NH—Me |
| 27 | —CO—CH$_2$—NMe$_2$ |
| 28 | —CO—CH$_2$—NMe$_3$$^+$I$^-$ |
| 29 | —CO—CH$_2$—NMe—Z |
| 30 | —CO—CHMe—NH$_2$ |
| 31 | —CO—CHMe—NH—Me |
| 32 | —CO—CHMe—NMe$_2$ |
| 33 | —CO—CHMe—NMe$_3$$^+$I$^-$ |
| 34 | —CO—CHMe—NMe—Z |
| 35 | —CO—CHEt—NH—Me |
| 36 | —CO—CHiPr—NH—Me |

TABLE 1-continued

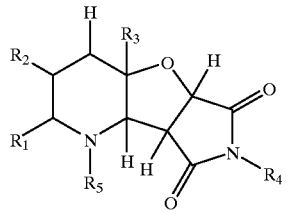

(Ib-1)

Compounds of Table 1 correspond to the general formula (Ib-1), in which $R^1 = -H$, $R^2$, $R^3$, $R^4 = $ -methyl, $R^5$ is as listed below:

| Compound No. | $R^5$ |
|---|---|
| 37 | —CO—NH—Me |
| 38 | —CH$_2$—CH$_2$—NMe$_2$ |
| 39 | —CH$_2$—CO—OEt |
| 40 | —CHMe—CO—OMe |
| 41 | (methylsulfonylmethyl-piperazinyl-pyridin-4-yl) |
| 42 | (methylsulfonylmethyl-piperazinyl-pyrimidin-2-yl) |
| 43 | (methylsulfonylmethyl-piperazinyl-pyridin-2-yl) |
| 44 | (methylsulfonylmethyl-piperazinyl-CO-OEt) |
| 45 | (acetyl-piperidinyl-CO-OMe) |
| 46 | (acetyl-piperidinyl-CO-OMe) |

TABLE 1-continued

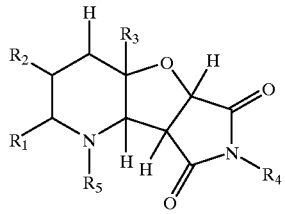

(Ib-1)

Compounds of Table 1 correspond to the general formula (Ib-1), in which $R^1 = -H$, $R^2$, $R^3$, $R^4 = $ -methyl, $R^5$ is as listed below:

| Compound No. | $R^5$ |
|---|---|
| 47 | (acetyl-piperazinyl-ethyl-morpholinyl) |
| 48 | (acetyl-dioxopiperazinyl-N-Et) |
| 49 | (acetyl-piperazinyl-ethyl-OMe) |
| 50 | (acetyl-piperazinyl-CH$_2$-CO-pyrrolidinyl) |
| 51 | (acetyl-piperazinyl-propargyl) |
| 52 | (acetyl-piperazinyl-N-Me) |
| 53 | (CHMe-CO-morpholinyl) |
| 54 | (acetyl-thiomorpholinyl-S-dioxide) |

TABLE 1-continued (Ib-1)

Compounds of Table 1 correspond to the general formula (Ib-1), in which $R^1$ = —H, $R^2$, $R^3$, $R^4$ = -methyl, $R^5$ is as listed below:

| Compound No. | $R^5$ |
|---|---|
| 55 | *3-azaspiro[5.5]undecyl acetyl group* |
| 56 | *tert-butyl prolinate acetyl group* |
| 57 | *4-methyl-2,6-dioxopiperazinyl acetyl group* |
| 58 | *N-methyl-N-((6-chloropyridin-3-yl)methyl)aminoacetyl group* |
| 59 | *methylsulfonylmethyl-piperazinyl-ethyl-morpholine* |
| 60 | *methylsulfonylmethyl-piperazinyl-ethyl-morpholine* |
| 61 | *methyl-piperazinyl-ethyl-morpholine ketone* |
| 62 | *piperazinyl (1-methylethyl) acetyl group* |
| 63 | *piperazinyl-ethyl-N,N-dimethylamino acetyl group* |
| 64 | *piperazinyl-benzodioxole acetyl group* |
| 65 | *piperazinyl-allyl acetyl group* |
| 66 | *morpholinyl acetyl group* |
| 67 | *thiomorpholinyl acetyl group* |
| 68 | *tetrahydropyridinyl acetyl group* |
| 69 | *3-methoxyquinuclidinyl group* |

TABLE 1-continued
(Ib-1)
Compounds of Table 1 correspond to the general formula (Ib-1), in which R¹ = —H, R², R³, R⁴ = -methyl, R⁵ is as listed below:
| Compound No. | R⁵ |
|---|---|
| 77 | 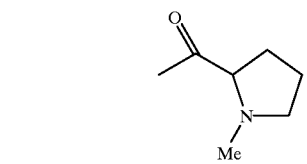 |
| 78 | |
| 79 | 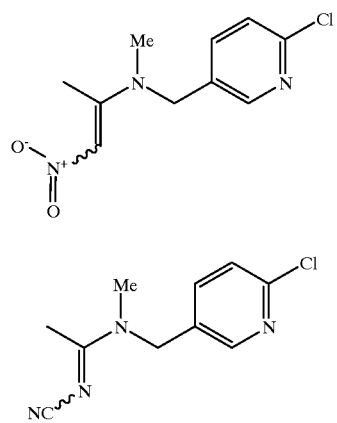 |
| 80 | |
| 81 | —CO—CH₂—NMe—O—Me |
| 82 | —CO—O—CHMe—CH=CH₂ |
| 83 | —SO₂—NMe—CO—O—Me |
| 84 | —CO—CH₂—CF=CF₂ |
| 85 | —CO—N(CH₂—CH₂—OH)₂ |
| 86 | 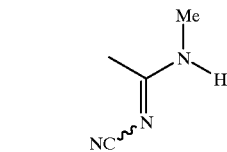 |
| 87 | 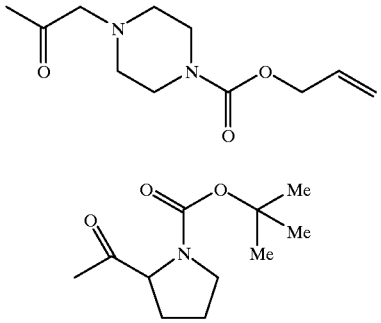 |

TABLE 1-continued (Ib-1)

Compounds of Table 1 correspond to the general formula (Ib-1), in which R¹ = —H, R², R³, R⁴ = -methyl, R⁵ is as listed below:

| Compound No. | R⁵ |
|---|---|
| 88 | [morpholine-NH-CH2-C(O)-] |
| 89 | [1-acetyl-4-hydroxypyrrolidin-2-yl-C(O)-] |
| 90 | [Ac-N(Me)-C(O)-morpholine] |
| 91 | [pyrrolidine-SO2-] |
| 92 | [6-chloropyridin-3-yl-CH2-N(Me)-C(Me)=CH-CN] |
| 93 | [MeS-C(Me)=CH-NO2] |
| 94 | —SO$_2$—CH$_2$—NMe—CH$_2$—C≡CH |
| 95 | —CO—CH$_2$—NMe—CH$_2$≡CH |
| 96 | —CO—CH$_2$—NMe—CH$_2$—C≡CH |
| 97 | —PS(O—Et)$_2$ |
| 98 | —CO—CH$_2$—NMe—CHMe—Ph |
| 99 | [4-(NMe2)-C6H4-CH2-O-C(O)-] |
| 100 | [4-MeO-C6H4-CH2-O-C(O)-] |
| 101 | [4-morpholino-C6H4-CH2-O-C(O)-] |
| 102 | [4-(NMe2)-C6H4-O-CH2-C(O)-] |
| 103 | [4-MeO-C6H4-O-CH2-C(O)-] |
| 104 | [4-morpholino-C6H4-O-CH2-C(O)-] |

Table 2

Table 2 contains the compounds of the general formula (Ib-1), in which $R^1$=—H; $R^2$, $R^3$=-methyl; $R^4$=-ethyl; $R^5$ has the meanings listed in Table 1.

Table 3

Table 3 contains the compounds of the general formula (Ib-1), in which $R^1$=—H; $R^2$, $R^3$=-methyl; $R^4$=-n-propyl; $R^5$ has the meanings listed in Table 1.

Table 4

Table 4 contains the compounds of the general formula (Ib-1), in which $R^1$=—H; $R^2$, $R^3$=-methyl; $R^4$=-isopropyl; $R^5$ has the meanings listed in Table 1.

Table S

Table 5 contains the compounds of the general formula (Ib-1), in which $R^1$=—H; $R^2$, $R^3$=-methyl; $R^4$=-cyclopropyl; $R^5$ has the meanings listed in Table 1.

Table 6

Table 6 contains the compounds of the general formula (Ib-1), in which $R^1$=—H; $R^2$,. $R^3$=-methyl; $R^4$=-n-butyl; $R^5$ has the meanings listed in Table 1.

Table 7

Table 7 contains the compounds of the general formula (Ib-1), in which $R^1$=—H; $R^2$, $R^3$=-methyl; 14=-sec-butyl; $R^5$ has the meanings listed in Table 1.

Table 8

Table 8 contains the compounds of the general formula (Ib-1), in which $R^1$=—H; $R^2$, $R^3$=-methyl; $R^4$=-isobutyl; $R^5$ has the meanings listed in Table 1.

Table 9

Table 9 contains the compounds of the general formula (Ib-1), in which $R^1$=—H; $R^2$, R=-methyl; $R^4$-cyclobutyl; $R^5$ has the meanings listed in Table 1.

Table 10

Table 10 contains the compounds of the general formula (Ib-1), in which $R^1$=—H; $R^2$, $R^3$=-methyl; $R^4$=-cyclopropylmethyl; $R^5$ has the meanings listed in Table 1.

Table 11

Table 11 contains the compounds of the general formula (Ib-1), in which $R^1$=—H; $R^2$, $R^3$=-methyl; $R^4$=-cyclopentyl; $R^5$ has the meanings listed in Table 1.

Table 12

Table 12 contains the compounds of the general formula (Ib-1), in which $R^1$=—H; $R^2$, $R^3$=-methyl; $R^4$=2-phenylethyl; $R^5$ has the meanings listed in Table 1.

Table 13

Table 13 contains the compounds of the general formula (Ib-1), in which $R^1$=—H; $R^2$, $R^3$=-methyl; $R^4$=-allyl; $R^5$ has the meanings listed in Table 1.

Table 14

Table 14 contains the compounds of the general formula (Ib-1), in which $R^1$=—H; $R^2$, $R^3$=-methyl;

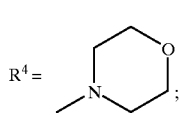

$R^5$ has the meanings listed in Table I.

Table 15

Table 15 contains the compounds of the general formula (Ib-1), in which $R^1$=—H; $R^2$, $R^3$-methy;

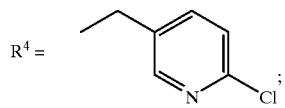

$R^5$ has the meanings listed in Table 1.

Table 16

Table 16 contains the compounds of the general formula (Ib-1), in which $R^1$—H; $R^2$=—CH$_2$—Br, $R^3$, $R^4$=-methyl; $R^5$ has the meanings listed in Table 1.

Table 17

Table 17 contains the compounds of the general formula (Ib-1), in which $R^1$=—H; $R^2$=—CH$_2$—Br, $R^3$=-methyl; $R^4$=-ethyl; $R^5$ has the meanings listed in Table 1.

Table 18

Table 18 contains the compounds of the general formula (Ib-1), in which $R^1$=—H; $R^2$=—CH$_2$—Br, $R^3$=-methyl; $R^4$=-cyclopropyl; $R^5$ has the meanings listed in Table 1.

Table 19

Table 19 contains the compounds of the general formula (Ib-1), in which $R^1$=—H; $R^2$=—CH$_2$—Br, $R^3$=-methyl; $R^4$=-n-butyl; $R^5$ has the meanings listed in Table 1.

Table 20

Table 20 contains the compounds of the general formula (Ib-1), in which $R^1$=—H; $R^2$=—CH$_2$—Br, $R^3$=-methyl; $R^4$=-cyclobutyl; $R^5$ has the meanings listed in Table 1.

Table 21

Table 21 contains the compounds of the general formula (Ib-1), in which $R^1$=—H;

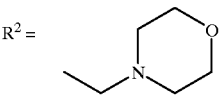

$R^4$=-methyl; $R^5$ has the meanings listed in Table 1.

Table 22

Table 22 contains the compounds of the general formula (Ib-1), in which $R^1$=—H;

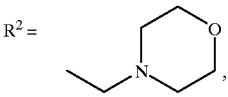

$R^3$=-methyl; $R^4$=-ethyl; $R^5$ has the meanings listed in Table 1.

Table 23

Table 23 contains the compounds of the general formula (Ib-1), in which $R^1$=—H;

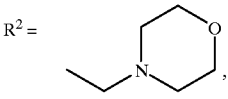

$R^3$=-methyl; $R^4$=-cyclopropyl; $R^5$ has the meanings listed in Table 1.

Table 24

Table 24 contains the compounds of the general formula (Ib-1), in which $R^1$=—H;

R² = 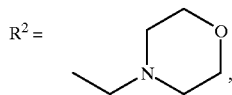

R³=-methyl; R⁴=-n-butyl; R⁵ has the meanings listed in Table 1.

Table 25

Table 25 contains the compounds of the general formula (Ib-1), in which R¹=—H;

R² = 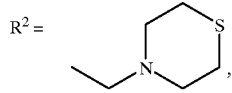

R³, R⁴=-methyl; R⁵ has the meanings listed in Table 1.

Table 26

Table 26 contains the compounds of the general formula (Ib-1), in which R¹=—H;

R² = 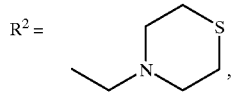

R³=-methyl; R⁴=-ethyl; R⁵ has the meanings listed in Table 1.

Table 27

Table 27 contains the compounds of the general formula (Ib-1), in which R¹=—H;

R² = 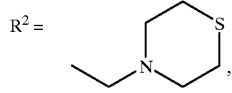

R³=-methyl; R⁴=-cyclopropyl; R⁵ has the meanings listed in Table 1.

Table 28

Table 28 contains the compounds of the general formula (Ib-1), in which R¹=—H;

R² = 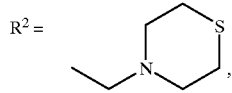

R³=-methyl; R⁴=-n-butyl; R⁵ has the meanings listed in Table 1.

Table 29

Table 29 contains the compounds of the general formula (Ib-1), in which R¹=—H;

R² = 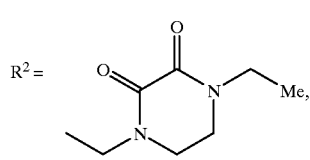

R³, R⁴=-methyl; R⁵ has the meanings listed in Table 1.

Table 30

Table 30 contains the compounds of the general formula (Ib-1), in which R¹=—H;

R² = 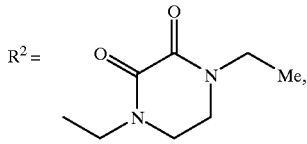

R³=-methyl; R⁴=-ethyl; R⁵ has the meanings listed in Table 1.

Table 31

Table 31 contains the compounds of the general formula (Ib-1), in which R¹=—H;

R² = 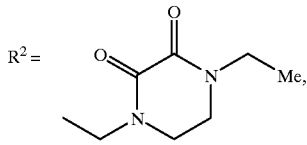

R³=-methyl; R⁴=-cyclopropyl; R⁵ has the meanings listed in Table 1.

Table 32

Table 32 contains the compounds of the general formula (Ib-1), in which R¹=—H;

R² = 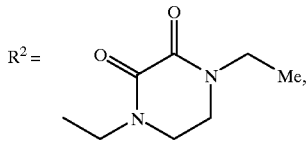

R³-methyl; R⁴-n-butyl; R⁵ has the meaning listed in Table 1.

Table 33

Table 33 contains the compounds of the general formula (Ib-1), in which R¹—H; R²=—CO—O—Me, R³, R⁴=-methyl; R⁵ has the meanings listed in Table I.

Table 34

Table 34 contains the compounds of the general formula (Ib-1), in which R¹—H; R²=—CO—O—Me, R³=-methyl; R 4=-ethyl; R⁵ has the meanngs listed in Table 1.

Table 35

Table 35 contains the compounds of the general formula (Ib-1), in which R¹=—H; R²=—CO—O—Me, R³=-methyl; R⁴=-cyclopropyl; R⁵ has the meanings listed in Table 1.

Table 36

Table 36 contains the compounds of the general formula (Ib-1), in which R¹=—H; R²=—CO—O—Me, R³=-methyl; R⁴=-n-butyl; R⁵ has the meanings listed in Table 1.

Table 37

Table 37 contains the compounds of the general formula (Ib-1), in which R¹=—H;

R² = 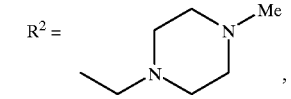

R⁴=-methyl; R⁵ has the meanings listed in Table 1.

Table 38

Table 38 contains the compounds of the general formula (Ib-1), in which R¹=—H;

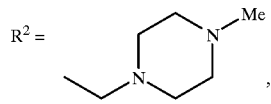

$R^3$=-methyl; $R^4$=-ethyl; $R^1$ has the meanings listed in Table 1.

Table 39

Table 39 contains the compounds of the general formula (Ib-1), in which $R^1$=—H;

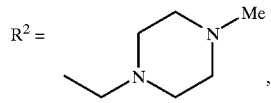

$R^3$=-methyl; $R^4$=-cyclopropyl; $R^5$ has the meanings listed in Table 1.

Table 40

Table 40 contains the compounds of the general formula (Ib-1), in which $R^1$=—H;

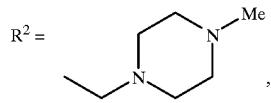

$R^3$=-methyl; $R^4$=-n-butyl; $R^5$ has the meanings listed in Table 1.

Table 41

Table 41 contains the compounds of the general formula (Ib-1), in which R=—H;

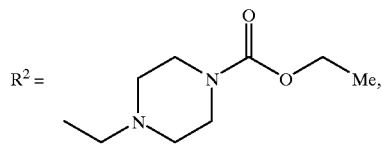

$R^3$, $R^4$=-methyl; $R^5$ has the meanings listed in Table 1.

Table 42

Table 42 contains the compounds of the general formula (Ib-1), in which $R^1$=—H;

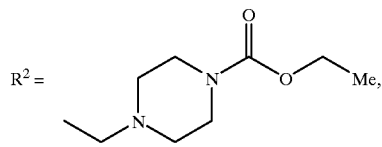

$R^3$=-methyl; $R^4$=-ethyl; $R^5$ has the meanings listed in Table 1.

Table 43

Table 43 contains the compounds of the general formula (Ib-1), in which $R^1$=—H;

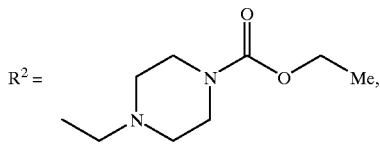

$R^3$=-methyl; $R^4$=-cyclopropyl; $R^5$ has the meanings listed in Table 1.

Table 44

Table 44 contains the compounds of the general formula (Ib-1), in which $R^1$=—H;

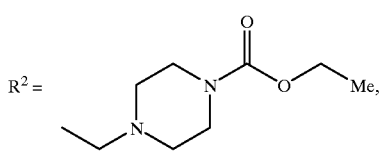

$R^3$=-methyl; $R^4$=-n-butyl; $R^5$ has the meanings listed in Table 1.

Table 45

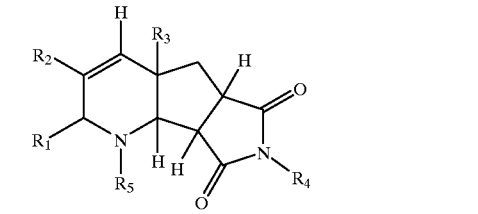

(Ic-1)

Table 45 contains the compounds of the general formula (Ic-1), in which $R^1$=—H; $R^2$, $R^3$, $R^4$=-methyl; $R^5$ has the meanings listed in Table 1.

Table 46

Table 46 contains the compounds of the general formula (Ic-1), in which $R^1$=—H; $R^2$, $R^3$=-methyl; $R^4$=-ethyl; $R^5$ has the meanings listed in Table 1

Table 47

Table 47 contains the compounds of the general formula (Ic-1), in which $R^1$=—H; $R^2$, $R^3$=-methyl; $R^4$=-n-propyl; $R^5$ has the meanings listed in Table 1.

Table 48

Table 48 contains the compounds of the general formula (Ic-1), in which $R^1$=—H; $R^2$, $R^3$=-methyl; $R^4$=-isopropyl; $R^5$ has the meanings listed in Table 1.

Table 49

Table 49 contains the compounds of the general formula (Ic-1), in which $R^1$=—H; $R^2$, $R^3$=-methyl; $R^4$=-cyclopropyl; $R^5$ has the meanings listed in Table 1.

Table 50

Table 50 contains the compounds of the general formula (Ic-1), in which $R^1$=—H; $R^2$, $R^3$=-methyl; $R^4$=-n-butyl; $R^5$ has the meanings listed in Table 1.

Table 51

Table 51 contains the compounds of the general formula (Ic-1), in which $R^1$=—H; $R^2$, $R^3$=-methyl; $R^4$=-cyclopropylmethyl; $R^5$ has the meanings listed in Table 1.

Table 52

Table 52 contains the compounds of the general formula (Ic-1), in which $R^1$=—H; $R^2$, $R^3$=-methyl; $R^4$=-2-phenylethyl; $R^5$ has the meanings listed in Table 1.

The compounds of the formula (Ia) are known in some cases, and they can be prepared by process a) described above under point 3 (cf., for example: T. Hisano et al. Chem. Pharm. Bull. 35 (3), (1987) pages 1049–1057;Heterocycles 29 (6), (1989) pages 1029–1032; Chem. Pharm. Bull. 38 (3), (1990) pages 605–611; Chem. Pharm. Bull. 39 (1), (1991) pages 10–17).

If 3,5-dimethyl-pyridine N-oxide is employed as compounds of the general formula (II) and N-benzyl-maleimide is employed as compounds of the formula (III) in process 3a for the preparation of the novel 4a, 5a, 8a, 8b-tetrahydro-6H-pyrrolo[3',4': 4,5]furo[3,2-b]pyridine-6,8(7H)-dione derivatives of the general formula (Ia), the process can be represented by the following equation:

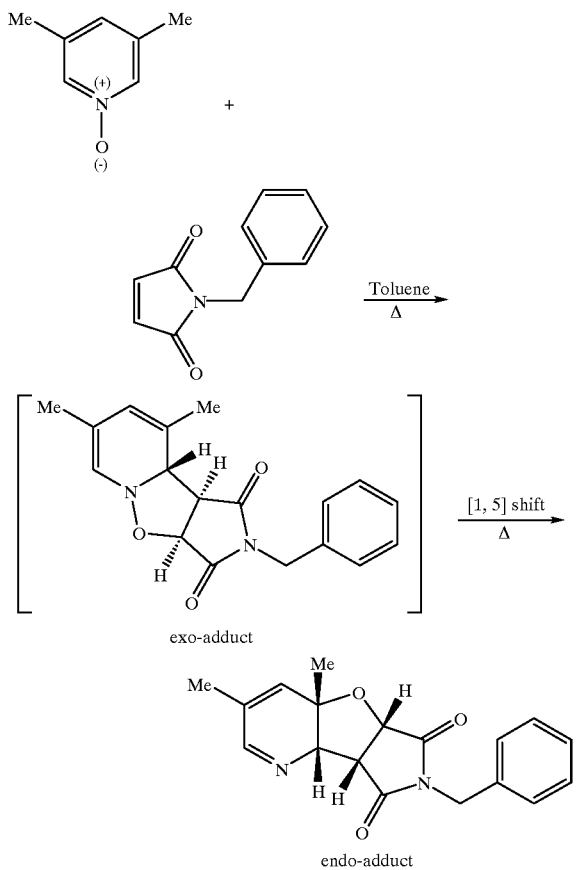

Formula (II) provides a general definition of the substituted pyridine N-oxides required as starting substances for carrying out process 3a according to the invention. In this formula, $R^1$, $R^2$, $R^3$ preferably represent those radicals which have already been mentioned as preferred for these substituents in connection with the description of the substances of the formula (I) according to the invention.

The substituted pyridine N-oxides used as starting materials are known in some cases, and can be ob-tained in some cases commercially or by methods known from the literature (for example J. M. Essery and K. Schofield J. Chem. Soc. (1960) page 49539).

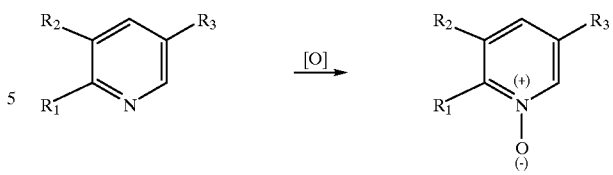

The most diverse peroxides, such as hydrogen peroxide, tert-butylperoxide, organic or inorganic peroxides or salts thereof, such as 3-chloro-perbenzo-ic acid, peracetic acid, performic acid, dibenzoylperoxide and the like, are possible for the oxidation of the pyridine derivatives to give the N-oxides of the general formula (II).

The peroxide can also be prepared in situ from another peroxide, for example peracetic acid from acetic acid and hydrogen peroxide.

The peroxide is preferably employed in equal equivalents to the starting pyridine. It is also possible to use an excess in order to bring the reaction to completion. All solvents which do not themselves undergo interfering side reactions with the oxidizing agents are suitable, such as, for example, water, alkyl alcohols, carboxylic acids, such as acetic acid or formic acid, or halogenated hydrocarbons, such as, inter alia, methylene chloride. The reaction temperatures are between −30° C. and +130° C., preferably between −10° C. and +80° C.

Formula (III) provides a general definition of the N-substituted maleimides furthermore required as starting substances for carrying out process 3a according to the invention. In this formula, $R^4$ preferably represents that radical which has already been mentioned as preferred for this substituent in connection with the description of the substances of the general formula (I) according to the invention.

The N-substituted maleimides of the general formula (III) used as starting materials are known in some cases, and can be obtained in some cases commercially or by methods known from the literature (cf., for example: EP 0608 445 Al, N. B. Mehta et al. J. Org. Chem. 25 (1960) pages 1012–1015; T. F. Braish et al. Synlett (1992) pages 979–980).

In general, it is advantageous to carry out process 3a according to the invention in the presence of diluents. Diluents are advantageously employed in an amount such that the reaction mixture remains readily stirrable throughout the entire process. Possible diluents for carrying out process 3a according to the invention are all inert organic solvents.

Examples which may be mentioned are: halogenohydrocarbons, in particular chlorohydrocarbons, such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-di-chloroethane, chlorobenzene, bromobenzene, dichlorobenzene, chlorotoluene, tri-chlorobenzene; alcohols, such as methanol, ethanol, isopropanol, butanol; ethers, such as ethyl propyl ether, methyl tert-butyl ether, n-butyl ether, anisole, phenetole, cyclohexyl methyl ether, dimethyl ether, diethyl ether, di-propyl ether, diisopropyl ether, di-n-butyl ether, diisobutyl ether, diisoamyl ether, ethylene glycol dimethyl ether, tetrahydrofuran, dioxane, dichlorodiethyl ether and polyethers of ethylene oxide and/ or propylene oxide; amines, such as trimethyl-, triethyl-, tripropyl-, tributylamine, N-methyl-morpholine, pyridine and tetramethylenediamine, nitrohydrocarbons, such as nitromethane, nitroethane, nitropropane, nitrobenzene, chloronitrobenzene, o-nitrotoluene; nitrites, such as acetonitrile, propionitrile, butyronitrile, isobutyronitrile, benzonitrile, m-chloro-benzonitrile, and compounds such as tetrahydro-thiophene dioxide and dimethyl sulfoxide, tetramethylene sulfoxide, dipropyl sulfoxide, benzylmethyl sulfoxide, diisobutyl sulfoxide, dibutyl sulfoxide, diisoamyl sulfoxide; sulfones, such as dimethyl, diethyl, dipropyl, dibutyl, diphenyl, dihexyl, methyl ethyl, ethyl propyl, ethyl isobutyl and pentamethylene sulfone; aliphatic, cycloaliphatic or aromatic hydrocarbons, such as pentane, hexane, heptane, octane, nonane and technical grade hydrocarbons, for example so-called white spirits with components having boiling points in the range of, for example, 40 to 250° C., cymene, benzine fractions within a boiling point range of 70° C. to 190° C., cyclohexane, methylcyclohexane, petroleum ether, ligroin, octane, benzene, toluene, chlorobenzene, bromobenzene, nitrobenzene, xylene; esters, such as methyl, ethyl, butyl, isobutyl acetate, and dimethyl, dibutyl, ethylene carbonate; amides, such as hexamethylenephosphor triamide, formamide, N-methylformamide, N,N-dimethylformamide, N,N-dipropylformamide, N,N-dibutylformamide, N-methyl-pyrrolidone, N-methyl-caprolactam, 1,3-dimethyl-3,4,5,6-tetrahydro-2(1H)-pyrimidine, octylpyrrolidone, octylca-prolactam, 1,3-dimethyl-2-imidazolinedione, N-formylpiperidine, N,N'-1,4-diformyl-piperazine; ketones, such as acetone, acetophenone, methyl ethyl ketone, methyl butyl ketone.

Mixtures of the solvents and diluents mentioned can of course also be employed in the process according to the invention.

Preferred diluents are aromatic halogenohydrocarbons, in particular chlorobenzene and bromobenzene, aromatic nitrohydrocarbons, such as nitrobenzene, aromatic hydrocarbons, in particular benzene and toluene, ketones, such as acetophenone, amides, such as N,N-dimethylformamide, sulfoxides, such as tetramethylene and sulfoxide and or mixtures of these with other diluents mentioned.

Process 3a is carried out by reacting substituted pyridine N-oxides of the general formula (II) with N-substituted maleimides of the general formula (III) in one of the diluents mentioned.

The duration of the reaction is 4 to 72 hours. The reaction is carried out at temperatures between −10° C. and +250° C., preferably between 0° C. and +200° C., particularly preferably at room temperature to +150° C. It is preferably carried out under the pressure which is established on heating to the required reaction temperature under the reaction conditions.

For carrying out process 3a according to the invention, in general 1.0 to 3.0 mol, preferably 1.0 to 2.0 mol, of N-substituted maleimide are employed per mol of compound of the formula (II).

When the reaction is complete, the reaction solution is concentrated in vacuo. The products obtained can be purified in the customary manner by recrystallization, vacuum distillation or column chromatography (cf. also the preparation examples).

The following compounds of the general formula (Ia) in which the radicals $R^1$ to $R^4$ have the following meaning may be mentioned specifically:

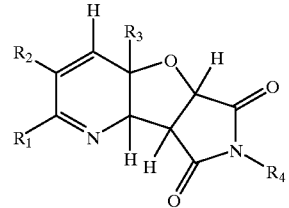
(Ia)

| $R_1$ | $R_2$ | $R_3$ | $R_4$ |
|---|---|---|---|
| —H | —CH₃ | —CH₃ | —CH₂—CF₃ |
| —H | —CH₃ | —CH₃ | —CH₂—CH₂—F |
| —H | —CH₃ | —CH₃ | —CH₂—CH₁—CF₃ |
| —H | —CH₃ | —CH₃ | —CHMe₂ |
| —H | —CH₃ | —CH₃ | —CHMe—CF₃ |
| —H | —CH₃ | —CH₃ | —CH₂—C≡CH |
| —H | —CH₃ | —CH₃ | —(R)—CHMe-phenyl |
| —H | —CH₃ | —CH₃ | —CH₂—CO—O—Me |
| —H | —CH₃ | —CH₃ | —CH₂—CO—O-tBu |
| —H | —CH₃ | —CH₃ | —(R)—CHMe—CO—O-tBu |
| —H | —CH₃ | —CH₃ | —(R)—CHMe—CO—O—Me |
| —H | —CH₃ | —CH₃ | —(S)—CHMe—CO—O-tBu |
| —H | —CH₃ | —CH₃ | —(S)—CHMe—CO—O—Me |
| —H | —CH₂—Br | —CH₃ | —Me |
| —H | —CH₂—Br | —CH₃ | —Et |
| —H | —CH₂—Br | —CH₃ | -cyclopropyl |
| —H | —CH₂—Br | —CH₃ | -cyclobutyl |
| —H | —CH₂—Br | —CH₃ | -n-butyl |
| —H | —CH₂—Br | —CH₃ | -sec-butyl |
| —H | —CH₂—Br | —CH₃ | —(S)—CHMe-phenyl |
| —H | —CH₂—Br | —CH₃ | -benzyl |
| —H | —CH₂—NMe₂ | —CH₃ | —Me |
| —H | —CH₂—NMe₂ | —CH₃ | —Et |
| —H | —CH₂—NMe₂ | —CH₃ | -cyclopropyl |
| —H | —CH₂—NMe₂ | —CH₃ | -cyclobutyl |
| —H | —CH₂—NMe₂ | —CH₃ | -n-butyl |
| —H | —CH₂—NMe₂ | —CH₃ | -sec-butyl |
| —H | —CH₂—NMe₂ | —CH₃ | —(S)—CHMe-phenyl |
| —H | —CH₂—NMe₂ | —CH₃ | -benzyl |
| —H | 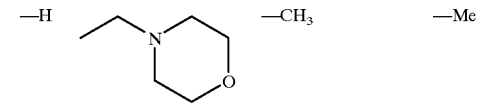 | —CH₃ | —Me |
| —H | 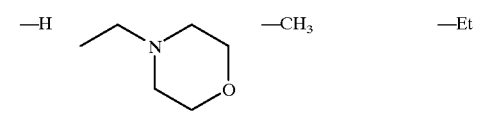 | —CH₃ | —Et |
| —H | 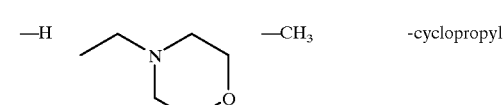 | —CH₃ | -cyclopropyl |
| —H | 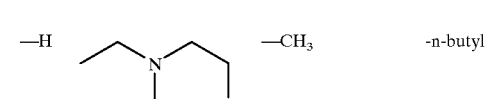 | —CH₃ | -n-butyl |
| —H | 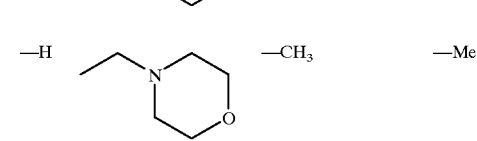 | —CH₃ | —Me |

-continued (Ia)

| R₁ | R₂ | R₃ | R₄ |
|---|---|---|---|
| —H | 4-ethylmorpholine | —CH₃ | —Et |
| —H | 4-ethylmorpholine | —CH₃ | -cyclopropyl |
| —H | 4-ethylmorpholine | —CH₃ | -n-butyl |
| —H | 4-ethylthiomorpholine | —CH₃ | —Me |
| —H | 4-ethylthiomorpholine | —CH₃ | —Et |
| —H | 4-ethylthiomorpholine | —CH₃ | -cyclopropyl |
| —H | 4-ethylthiomorpholine | —CH₃ | -n-butyl |
| —H | 1-ethyl-4-ethyl-2,3-dioxopiperazine | —CH₃ | —Me |
| —H | 1-ethyl-4-ethyl-2,3-dioxopiperazine | —CH₃ | —Et |
| —H | 1-ethyl-4-ethyl-2,3-dioxopiperazine | —CH₃ | -cyclopropyl |

-continued (Ia)

| R₁ | R₂ | R₃ | R₄ |
|---|---|---|---|
| —H | 1-ethyl-4-ethyl-2,3-dioxopiperazine | —CH₃ | -n-butyl |
| —H | —CO—O—Me | —CH₃ | —Me |
| —H | —CO—O—Me | —CH₃ | —Et |
| —H | —CO—O—Me | —CH₃ | —CHMe₂ |
| —H | —CO—O—Me | —CH₃ | -cyclopropyl |
| —H | —CO—O—Me | —CH₃ | -n-butyl |
| —H | 4-methyl-1-ethylpiperazine | —CH₃ | —Me |
| —H | 4-methyl-1-ethylpiperazine | —CH₃ | —Et |
| —H | 4-methyl-1-ethylpiperazine | —CH₃ | -cyclopropyl |
| —H | 4-methyl-1-ethylpiperazine | —CH₃ | -n-butyl |
| —H | 1-ethyl-1,2,3,6-tetrahydropyridine | —CH₃ | —Me |
| —H | 1-ethyl-1,2,3,6-tetrahydropyridine | —CH₃ | —Et |
| —H | 4-ethoxycarbonyl-1-ethylpiperazine | —CH₃ | —Me |

-continued (Ia)

| R₁ | R₂ | R₃ | R₄ |
|---|---|---|---|
| —H | piperazine-N-CO-O-Et (N-ethyl) | —CH₃ | —Et |
| —H | 4-(pyridin-2-yl)piperazin-1-yl (N-ethyl linker) | —CH₃ | —Me |
| —H | 4-(pyridin-2-yl)piperazin-1-yl (N-ethyl linker) | —CH₃ | —Et |
| —H | 4-(pyridin-2-yl)piperazin-1-yl (N-ethyl linker) | —CH₃ | —Me |
| —H | 4-(pyridin-2-yl)piperazin-1-yl (N-ethyl linker) | —CH₃ | —Et |

-continued (Ia)

| R₁ | R₂ | R₃ | R₄ |
|---|---|---|---|
| —H | 4-(pyridin-2-yl)piperazin-1-yl (N-ethyl linker) | —CH₃ | —Et |

The present invention also relates to the compounds of the general formula (I) in the form of an acid addition salt. Acids which can be used for salt formation are inorganic acids, such as hydrochloric acid, hydrobromic acid, nitric acid, sulfuric acid, phosphoric acid or organic acids, such as formic acid, acetic acid, propionic acid, malonic acid, oxalic acid, fumaric acid, adipic acid, stearic acid, tartaric acid, oleic acid, methanesulfonic acid, benzenesulfonic acid or toluenesulfonic acid.

Examples which may be mentioned of the preparation of suitable salts of compounds of the general formula (Ia) are hydrochloride formation and preparation of the corresponding $N^1$-methylammonium halides of the general formula (V), for example the $N^1$-methylammonium iodide of 7-ethyl-4a, 5a, 8a, 8b-tetrahydro-3,4a-dimethyl-6H-pyrrolo[3',4': 4,5]furo[3,2-b]pyridine-6,8(7H)-dione:

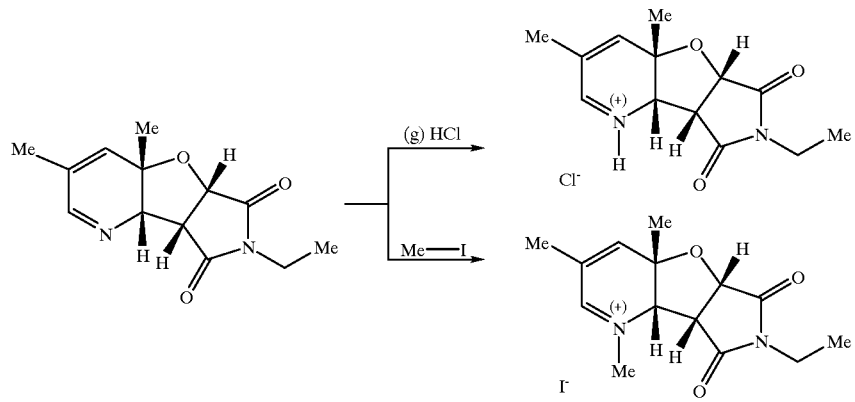

The salt formation is carried out by reacting compounds of the general formula (Ia), for example in the presence of inorganic acids, such as gaseous hydrochloric acid, or with an alkylating agent, such as methyl iodide, in one of the diluents mentioned for process 3a.

The duration of the reaction is 10 minutes to 24 hours The reaction is carried out at temperatures between −60° C. and +150° C., preferably between −10° C. and +80° C., particularly preferably at 0° C. to room temperature. It is carried out under normal pressure. For the salt formation, in general an excess of acid or alkylating agent is employed per mol of compound of the formula (Ia).

When the reaction is complete, the salt, which has usually precipitated out, is separated off, washed and dried in vacuo (cf. also the Preparation examples).

Surprisingly, the novel 4a, 5a, 8a, 8b-tetrahydro-6H-pyrrolo[3',4': 4,5]furo[3,2-b]pyridine-6,8(7H)-dione derivatives of the general formula (Ia) can be converted via hydrogenation of one or both double bonds in the dihydropyridine part into the novel 1, 2, 3, 4, 4a, 5a, 8a, 8b-octahydro-6H-pyrrolo[3',4': 4,5]furo[3,2-b]pyridine-6,8(7H)-dione and 1, 2, 4a, 5a, 8a, 8b-hexahydro-6H-pyrrolo[3'4': 4,5]furo[3,2-b]pyridine-6,8(7H)-dione derivatives of the general formulae (Id) and (Ie) and can be used for subsequent reactions according to process 5.

In general, a procedure is followed in process 5 in which the novel 4a, 5a, 8a, 8b-tetrahydro-6H-pyrrolo[3',4': 4,5]furo[3,2-b]pyridine-6,8(7H)-dione derivatives of the general formula (Ia) are first hydrogenated in the presence of a catalyst and in the presence of a diluent, the corresponding novel 1, 2, 3, 4, 4a, 5a, 8a, 8b-octahydro-6H-pyrrolo[3',4': 4,5]furo[3,2-b]pyridine-6,8 (7H)-dione-and/or 1, 2, 4a, 5a, 8a, 8b-hexahydro-6H-pyrrolo[3',4': 4,5]furo[3,2-b]pyridine-6,8(7H)dione derivatives of the general formulae (Id) and (Ie) being formed.

As expected, the compounds of the general formula (Id) are present in the form of an isomer mixture comprising a 3α isomer and 3β isomer.

If, for example, 7-benzyl-4a, 5a, 8a, 8b-tetrahydro-6H-pyrrolo[3',4': 4,5]furo[3,2-b]pyridine-6,8(7H)-dione is employed as the compound of the general formula (Ia) for the hydrogenation, an isomer mixture of 7-benzyl-1, 2, 3, 4, 4aα, 5aα, 8aα, 8bα-(±)-octahydro-3α, 4a-dimethyl-6H-pyrrolo[3',4': 4,5]furo[3,2-b]pyridine-6,8(7H)-dione (3a-isomer) and 7-benzyl-1, 2, 3, 4, 4aα, 5aα, 8aα, 8bα-(±) octahydro-3β, 4a-dimethyl-6H-pyrrolo[3',4': 4,5]furo[3,2-b]pyridine-6,8(7H)-dione (3β-isomer) is formed.

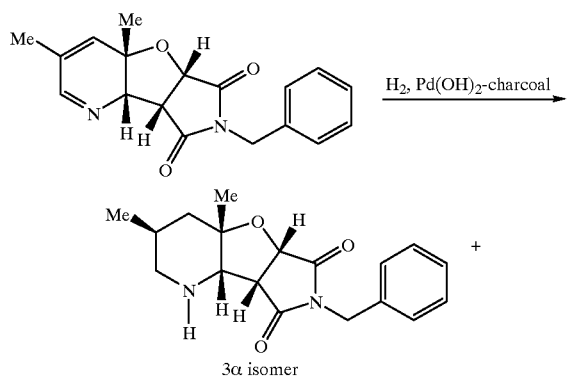

3α isomer

-continued

3β isomer

If, for example, 7-methyl-4a, 5a, 8a, 8b-tetrahydro-6H-pyrrolo[3',4': 4,5]furo[3,2-b]pyridine-6,8(7H)-dione is used as the compound of the general formula (Ia) for the hydrogenation, in addition to the isomer mixture of 7-methyl-1, 2, 3, 4, 4aα, 5aα, 8aα, 8bα-(±)-octahydro-3α, 4a-dimethyl-6H-pyrrolo[3',4': 4,5]-furo[3,2-b]pyridine-6,8-(7H)-dione (3α isomer) and 7-methyl-1, 2, 3, 4, 4aα, 5aα, 8aα, 8bα-(±)-octahydro-3α, 4a-dimethyl-6H-pyrrolo[3',4': 4,5]furo[3,2-b]pyridine-6,8(7H)-dione (3β iso-mer) of the general formula (Id), 7-methyl-1, 2, 4a, 5a, 8a, 8b-hexahydro-6H-pyr-rolo[3',4': 4,5]furo[3,2-b]pyridine-6,8(7H)-dione of the general formula (Ie) can also be obtained.

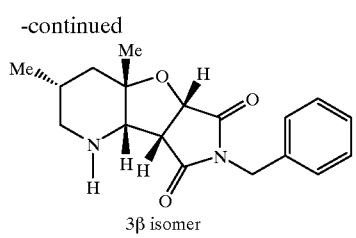

3α/3β isomer mixture

3α/3β isomer mixture

Diluents which are used for the hydrogenation are the inert organic solvents mentioned for process 3a such as, for example, alcohols, in particular ethanol.

The formation of the 1, 2, 4a, 5a, 8a, 8b-hexahydro-6H-pyrrolo[3'4': 4,5]furo[3,2-b]pyridine-6,8(7H)di-one derivatives of the general formula (Ie) according to the invention can be influenced by the hydrogenation conditions mentioned below.

Possible suitable catalysts for carrying out the catalytic hydrogenation are all the customary hydrogenation catalysts, such as, for example, platinum catalysts (platinum sheet, platinum sponge, platinum black, colloidal platinum, platinum oxide, platinum wire and the like), palladium catalysts (for example palladium sponge, palladium black, palladium oxide, palladium-on-charcoal, colloidal palladium, palladium barium sulfate, palladium barium carbonate, palladium hydroxide and the like), nickel catalysts (for example reduced nickel, nickel oxide, Raney nickel and the like), ruthenium catalysts, cobalt catalysts (for example reduced cobalt, Raney cobalt and the like), iron catalysts (for example reduced iron, Raney iron and the like), copper catalysts (for example reduced copper, Raney copper, Ullman copper and the like). Preferably, however, noble metal catalysts, such as, for example, platinum and palladium or ruthenium catalysts, are used, if appropriate on a suitable support, such as, for example, carbon or silicon dioxide.

For carrying out the hydrogenation, an alcoholic solution of the compounds of the formula (Ia) is reacted in the presence of a suitable hydrogenation catalyst, for example palladium hydroxide/charcoal. The duration of the reaction is 1 to 20 hours. The hydrogenation is carried out at temperatures of between +10° C. and +150° C., preferably between +15° C. and +100° C.

The isomer mixtures (3α isomers and 3β isomers) thus obtained are worked up in the customary manner, for example by purification by chromatography. (cf. also the Preparation examples). However, they can also be reacted directly (without further separation) in accordance with processes 5a to 5i.

By using a "chiral hydrogenation catalyst", for example with chiral diphosphine ligands, for example (2S,3S)-(−)-2,3-bis-(diphenylphosphino)-butane [(S,S)-chiraphos] (N. K. Roberts in "Catalytic Aspects of Metal Phosphine Complexes" (1982) page 337 ACS Washington) or R(±)-2,2'- or S(−)-2,2'-bis-(diphenylphosphino)-1,1'-binaphthalene [R(±)-BINAP or S(−)-BrNAP] (cf. A. Miyashita et by al. Tetrahedron 40 (1984) page 1245), the content of one isomer (3α isomer or 3β isomer) in the isomer mixture can of course also be increased significantly, or the formation of another isomer (3α isomer or 3β isomer) can even be suppressed completely.

The 1,2,4a,5a,8a,8b-hexahydro-6H-pyrrolo[3',4': 4,5]furo [3,2-b]pyridine-6,8(7H)-dione derivatives of the general formula (Ie) can be selectively prepared from the corresponding N¹-methylammonium halides of the general formula (V), such as for example the N¹-methylammonium iodide, followed by N¹-demethylation (cf B. Frolund et al., J. Med. Chem. 38, 1995, page 3287).

The selective preparation of the 1,2,4a,5a,8a,8b-hexahydro-6H-pyrrolo[3',4': 4,5]furo-[3,2-b]pyridine-6,8 (7H)-dione derivatives of the formula (Ie) according to the invention can be illustrated by the hydrogenation of the corresponding N¹-methylammonium iodide of 7-methyl-4aα,5aα,8aα,8bα-tetrahydro-3 ,4a-dimethyl-6H-pyrrolo[3',4': 4,5]furo[3,2-b]pyridine-6,8(7H)-dione:

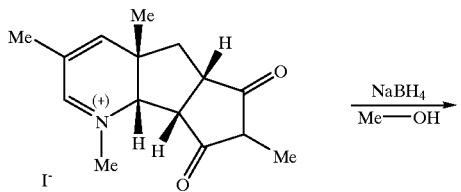

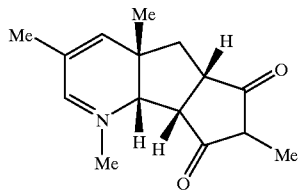
-continued

The hydrogenation of the corresponding N¹-methylammonium iodide is carried out by reacting compounds of the general formula (V), such as for example the N¹-methylammonium iodide of 7-methyl-4aα, 5aα,8aα, 8bα-tetrahydro-3,4a-dimethyl-6H-pyrrolo[3',4': 4,5]furo[3,2-b]pyridine-6,8(7,8)dione, in the presence of sodium hydridoborate in one of the diluents mentioned in connection with the subsequent process 3a.

Inert organic solvents, such as for example alcohols, and in particular methanol or ethanol, are preferably used as diluents for the hydrogenation process.

The reaction time is from 10 minutes to 48 hours. The reaction is carried out at temperatures of between −60° C. and +100° C., preferably between −30° C. and +80° C., and more preferably at from −10° C. to room temperature. The reaction is carried out under atmospheric pressure. For the hydrogenation process a slight excess of hydrogenation agent is generally used per mol N¹-methylammonium halide of the formula (V).

When the reaction is complete working up is carried out in the customary manner, such as for example by chromatographic purification (cf. also the preparation examples).

In general the subsequent N¹-demethylation is carried out by first reaction the new 1,2,4a,5a,8a,8b-hexahydro-6H-pyrrolo[3',4': 4,5]furo[3,2-b]pyridine-6,8(7H)-diones of the general formula (VI) in the presene of a suitable chloroformic acid ester in the manner described by R. F. Olofson et al.(J.Org. Chem. 49, 4984, page 2081), as a result of which the corresponding carbamates of the 1,2,4a,5a,8a,8b-hexahydro-6H-pyrrolo[3',4': 4,5]furo[3,2-b]pyridine-6,8 (7H)-diones of the general formula 1 g) are formed (cf. also process 5i).

The N¹-demethylation of the 1,2,4a,5a,8a,8b-hexahydro-6H-pyrrolo[3',4': 4,5]furo[3,2-b]pyridine-6,8(7H)-diones of the general formula (VI) according to the invention can be illustrated by the elimination of the corresponding N¹-methyl radical from 7-methyl-4aα,5aα,8aα,8bα-tetrahydro-3 ,4a-dimethyl-6H-pyrrolo[3',4': 4, 5]furo[3,2-b]-pyridine-6,8(7H)-dione using 1-chloroethoxycarbonyl chloride:

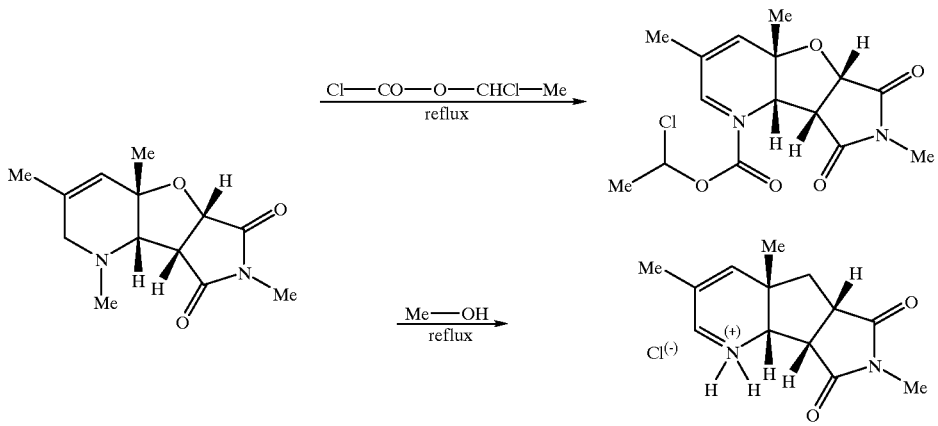

In order to carry out the $N^1$-demethylation the 1,2,4a,5a, 8a,8b-hexahydro-6H-pyrrolo[3',4': 4,5]furo[3,2-b]pyridine-6,8(7H)-diones of the general formula (VI) are heated in the presence of an excess of 1-chloroethoxycarbonyl chloride. The reaction time is from 1 to 24 hours. The $N^1$-demethylation is carried out at temperatures between 0° C. and +200° C., preferably at tempeatures between +5° C. and +150° C., and more preferably at temperatures between +50° C. and +130° C.

The 1-chloroethoxycarbonyl-1,2,4a,5a,8a,8b-hexahydro-6H-pyrrolo[3',4': 4,5 ]furo[3,2-b]pyridine-6,8(7H)-diones obtained in this way are worked up in the customary manner, for example by means of chromatographic purification (cf. also the preparation examples).

The 1-chloroethoxycarbonyl-1,2,4a,5a,8a,8b-hexahydro-6H-pyrrolo[3',4': 4,5]-furo[3,2-b]pyridine-6,8(7H)-diones are reacted in one of the diluents mentioned in relation to the subsequent process 3a.

Inert organic solvents, such as for example alcohols, and in particular methanol or ethanol, are preferably used as diluents for the $N^1$-demethylation.

The reaction time is from 10 minutes to 24 hours. The reaction is carried out at a temperature between 0° C. and +100° C., preferably at temperatures between +10° C. and +80° C. The reaction can generally be carried out under atmospheric pressure.

When the reaction is complete the resulting hydrochloride is worked up in the customary manner (cf also the preparation examples).

If 7-ethyl-1, 2, 3, 4, 4aα, 5aα, 8aα,8bα-(±)-octahydro-33α,4a-dimethyl-6H-pyrrolo[3'4': 4, 5]furo[3,2-b]pyridine-6,8(7H)dione is employed as compounds of the general formula (Id) and methyl iodide is employed as compounds of the general formula (VII) in process 5a for the preparation of the novel 1-substituted 2, 3, 4, 4a, 5a, 8a, 8b-octahydro-6H-pyrrolo[3',4': 4,5]furo[3,2-b]pyridine-6,8(7H)-dione derivatives of the general formula (Ib), the process can be represented by the following equation:

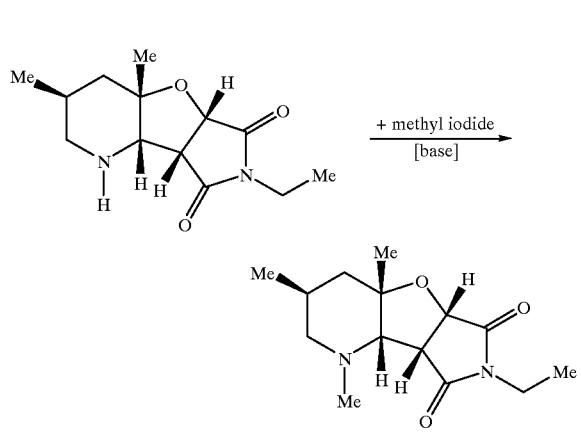

Formula (Id) provides a general definition of the 1, 2, 3, 4, 4aα, 5aα, 8aα,8bα-(±)-octahydro-33α,4a-dialkyl-6H-pyrrolo-[3',4': 4,5]furo[3,2-b]pyridine-6,8(7H)-diones required as starting substances for carrying out process 5a according to the invention. In this formula $R^1$, $R^2$, $R^3$ and $R^4$ preferably represent those radicals which have already been mentioned as preferred for these substituents in connection with the description of the substances of the general formula (Ib) according to the invention.

The 1, 2, 3, 4, 4aα, 5aα, 8aα, 8bα-(±)octahydro-3, ,4a-dialkyl-6H-pyrrolo[3',4': 4,5]furo[3,2-b]pyridine-6,8 (7H)-diones of the general formula (Id) used as starting materials are novel and can be obtained from the 4a, 5a, 8a, 8b-tetrahydro-3 ,4a-dialkyl-6H-pyrrolo[3 '4': 4,5]furo[3,2-b] pyridine-6,8(7H)-dione derivatives (Ia) by the hydrogenation process described above.

Formula (IV) provides a general definition of the alkylating or heteroarylating agents ($R^5$=heteroaryl) furthermore to be used as starting substances for carrying out process 5a according to the invention.

In the formula (VII), $R^5$ has the meaning which has already been mentioned as pre-ferred for these substituents in connection with the description of the substances of the general formula (Ib) according to the invention, and E has the meaning of an electron-withdrawing leaving group.

Suitable leaving groups are, for example, halogen, such as fluorine, chlorine, bromine and iodine, sulfonate, such as aryl- and perfluoroalkylsulfonate, monosubstituted diazo and monosubstituted nitrato, and those additionally listed in J. March, Advanced Organic Chemistry, 3rd edition, John Wiley & Sons, New York 1985, pages 310–316.

Alkylating or heteroarylating agents of the formula (VII) are generally known compounds of organic chemistry or can be obtained commercially or by methods known from the literature (for example: Houben-Weyl, Methoden der organischen Chemie [Methods of organic chemistry], Volume V/3, pages 830, 862; Volume V/4, pages 361, 610).

In general, it is advantageous to carry out process 5a according to the invention in the presence of diluents and if appropriate in the presence of a basic reaction auxiliary.

Possible diluents for carrying out process 3a according to the invention are all the inert organic solvents.

Preferred diluents are ketones, in particular acetone, methyl ethyl ketone or methyl isobutyl ketone, amides, in particular N,N-di-methylformamide, N,N-dimethylacetamide or N-methyl-pyrrolidone, benzine fractions within a boiling point range of 70° C. to 190° C., in particular benzene, toluene, chlorobenzene, bromobenzene, nitrobenzene or xylene, and mixtures of these with other diluents mentioned.

Mixtures of the solvents and diluents mentioned can of course also be employed in process 5a according to the invention.

All suitable acid-binding agents can be employed as basic reaction auxiliaries for carrying out process 5a according to the invention, such as amines, in particular tertiary amines, and alkali metal and alkaline earth metal compounds.

Examples of these which may be mentioned are the hydrides, hydroxides, oxides and carbonates of lithium, sodium, potassium, magnesium, calcium and barium, and furthermore other basic compounds, such as amidine bases or guanidine bases, such as 7-methyl-1,5,7-triazabicyclo (4.4.0)dec-5-ene (MTBD); diazabicyclo(4.3.0)-nonene (DBN), diazabicyclo(2.2.2)-octane (DABCO), 1,8-diazabicyclo-(5.4.0)undecene (DBU) cyclohexyltetrabutylguanidine (CyTBG), cyclohexyltetramethylguanidine (CyTMG), N,N,N,N-tetramethyl-1,8-naphthalenediamine, pentamethyl-piperidine, tertiary amines, such as triethylamine, trimethylamine, tribenzylamine, triisopropylamine, tributylamine, tribenzylamine, tricyclohexylamine, triamylamine, trihexylamine, N,N-dimethylaniline, N,N-dimethyltoluidine, N,N-dimethyl-p-aminopyridine, N-methyl-pyrrolidine, N-methylpiperidine, N-methyl imidazole, N-methyl-pyrrol, N-methyl-morpholine, N-methylhexa-methyleneimine, pyridine, 4-pyrrolidinopyridine, 4-dimethylamino-pyridine, quinoline, α-picoline, β-picoline, isoquinoline, pyrimidine, acridine, N,N,N',N'-tetramethylenediamine, N,N',N'-tetraethylenediamine, quinoxaline, N-propyl-diisopropylamine, N-ethyl-diisopropylamine, N,N'-dimethylcyclohexylamine, 2,6-lutidine, 2,4-lutidine or triethylenediamine.

Tertiary amines, in particular trialkylamines, such as triethylamine, N,N-diisopropylethylamine, N-propyl-diisopropylamine, N,N'-dimethylcyclohexyl-amine or N-methylmorpholine, and alkali metal carbonates, in particular sodium bicarbonate, sodium carbonate, potassium carbonate or potassium bicarbonate, are preferably used.

Process 5a is carried out by reacting compounds of the general formula (Id) with compounds of the general formula (VII) in the presence of a basic reaction auxiliary in one of the diluents mentioned.

The duration of the reaction is 4 to 72 hours. The reaction is carried out at temperatures between −10° C. and +250° C., preferably between 0° C. and +200° C., particularly preferably at 0° C. to 150° C. It is carried out under normal pressure. For carrying out process 5a according to the invention, in general 1.0 to 6.0 mol, preferably 1.0 to 4.0 mol, of basic reaction auxiliary and 1.0 to 4.0 mol, preferably 1.0 to 2.0 mol, of alkylating agent (VII) are employed per mol of compound of the formula (Id).

When the reaction is complete, the reaction solution is washed and the organic phase is separated off, dried and concentrated in vacuo. The products obtained can be purified in a customary manner by recrystallization, vacuum distillation or column chromatography (cf. also the Preparation examples).

If appropriate, the amino alkylation or reductive amino alkylation known from the literature (cf. Houben-Weyl, Methoden der Organischen Chemie [Methods of organic chemistry], Volume XI/I, page 648; W. S. Emerson, Org. Reactions 4 (1948), page 174) is also suitable for preparation of compounds of the general formula (Ib) and (Ic) for process 5a according to the invention.

If 7-ethyl-1, 2, 3, 4, 4aα, 5aα, 8aα, 8bα-(±)-octahydro-3α,4a-dimethyl-6H-pyrrolo[3',4': 4,5]furo[3,2-b] pyridine-6,8(7H)dione is employed as compounds of the general formula (Id) and acrylonitrile is employed as the compound of the general formula (VIII) in process 5b for the preparation of the novel 1, 2, 3, 4, 4a, 5a, 8a, 8b-octahydro-6H-pyrrolo[3',4': 4,5]furo[3,2-b]pyridine-6,8(7H)-dione derivatives of the general formula (Ib), the process can be represented by the following equation:

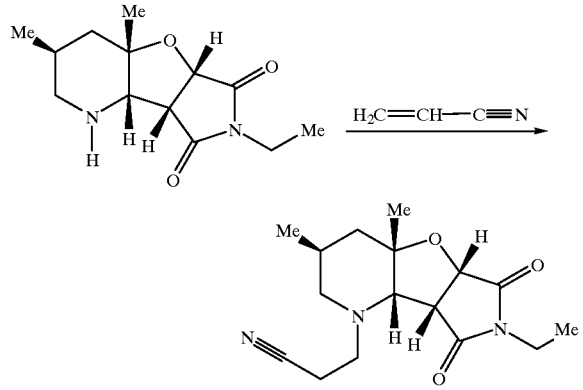

Formula (Id) provides a general definition of the 1, 2, 3, 4, 4aα, 5aα, 8aα, 8bα-(±)-octahydro-3α,4a-dialkyl-6H-pyrrolo[3',4': 4,5]furo[3,2-b]pyridine-6,8(7H)-diones required as starting substances for carrying out process 5b according to the invention. In this formula, $R^1$, $R^2$, $R^3$ and $R^4$ preferably represent those radicals which have already been mentioned as preferred for these substituents in connection with the description of the substances of the general formula (Ib) according to the invention.

The 1, 2, 3, 4, 4aα, 5aα, 8aα, 8bα-(±)-octahydro-3α,4a-dialkyl-6H-pyrrolo[3',4': 4,5]furo[3,2-b]pyridine-6,8(7H)-diones of the general formula (Id) used as starting materials are novel and can be obtained from the 4a, 5a, 8a, 8b-tetrahydro-3,4a-dialkyl-6H-pyrrolo [3',4': 4,5]furo [3,2-b]pyridine-6,8(7H)-dione derivatives (Ia) by the hydrogenation process described above.

Formula (VIII) provides a general definition of the compounds furthermore to be used as starting substances for carrying out process 5b according to the invention.

In the formula (VIII) $R^8$ has the meaning which have already been mentioned as preferred for these substituents in connection with the description of the substances of the general formula (Ib) according to the invention, and A represents a suitable ac-ceptor group, for example nitro, nitrile, carbamoyl, carboxyl or $C_{1-4}$-alkoxycarbonyl.

The compounds of the formula (VIII) are generally known compounds of organic chemistry and they can be obtained in some cases commercially or by methods known from the literature (for example: Houben-Weyl, Methoden der Organischen Chemie [Methods of organic chemistry], Volume VIII, page 265).

The reaction of the compounds (Id) with (VIII) is carried out, if appropriate, in the presence of a catalyst using diluents.

Diluents which are used for carrying out process 5b according to the invention are the inert solvents mentioned for process 3a, such as, for example, alcohols, in particular methanol or ethanol.

Process 5b is carried out by reacting compounds of the general formula (Id) with a compound general formula (VIII), if appropriate in the presence of a suitable catalyst, in one of the diluents mentioned.

The duration of the reaction is 4 to 72 hours. The reaction is carried out at temperatures between −10° C. and +200° C., preferably between −5° C. and +150° C., particularly preferably at 0° C. to 100. It can in principle be carried out under normal pressure, but can also be carried out under increased or reduced pressure. Preferably, the reaction is carried out under normal pressure or under pressures of up to 15 bar. At higher temperatures, it is advantageous to carry out the reaction under increased pressure, if appropriate also above 15 bar.

For carrying out process 5b according to the invention, in general 1.0 to 3.0 mol, preferably 1.0 to 2.0 mol, of compound of the formula (VIII) are employed per mol of compound of the formula Id.

When the reaction is complete, the reaction solution is washed and the organic phase is separated off, dried and concentrated in vacuo. The products obtained can be purified in a customary manner by recrystallization, vacuum distillation or column chromatography (cf. also the Preparation examples).

If 7-ethyl-1,2,3, 4, 4aα, 5aα, 8aα, 8bα-(±)-octahydro-3α,4a-dimethyl-6H-pyrrolo[3',4': 4,5]furo[3,2-b]pyridine-6,8(7H)-dione is employed as compounds of the general formula (Id) and (±)-2,3-epoxypropyl iso-propyl ether is employed as the epoxide of the general formula (IX) in process 5c for the preparation of the novel 1, 2, 3, 4, 4a, 5a, 8a, 8b-octahydro-6H-pyrrolo[3',4': 4,5]furo[3,2-b]pyridine-6,8(7H)-dione derivatives of the general formula (Ib), the process can be represented by the following equation:

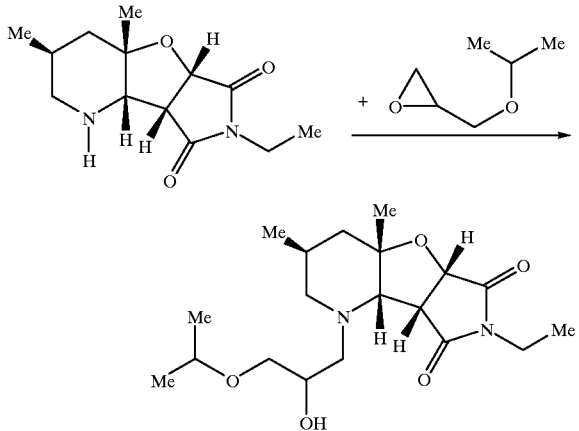

Formula (Id) provides a general definition of the 1, 2, 3, 4, 4aα, 5aα, 8aα, 8bα-(±)-octahydro-3α,4a-dialkyl-6H-pyrrolo-[3',4': 4,5]furo[3,2-b]pyridine-6,8(7H)-diones required as starting substances for carrying out process 5c according to the invention. In this formula, $R^1$, $R^2$, $R^3$ and $R^4$ preferably represent those radicals which have already been mentioned as preferred for these substituents in connection with the description of the substances of the general formula (Ib) according to the invention.

The 1, 2, 3, 4, 4aα, 5aα, 8aα, 8bα-(±)-octahydro-3α,4a-dialkyl-6H-pyrrolo[3',4': 4,5]furo[3,2-b]pyridine-6,8(7H)-diones of the general formula (Id) used as starting materials are novel and can be obtained from the 4a, 5a, 8a, 8b-tetrahydro-3,4a-dialkyl-6H-pyrrolo[3',4': 4,5]furo[3,2-b] pyridine-6,8(7H)-dione derivatives (Ia) by the hydrogenation process described above.

Formula (IX) provides a general definition of the epoxides furthermore to be used as starting substances for carrying out process 5c according to the invention.

In the formula (IX) $R^5$ has the meaning which have already been mentioned as preferred for these substituents in connection with the de-scription of the substances of the general formula (Ib) according to the invention.

The epoxides of the formula (IX) are generally known compounds of organic chemistry, and they can be obtained in some cases commercially or by methods known from the literature (for example: Houben-Weyl, Methoden der Organischen Chemie [Methods of organic chemistry], Volume VI/3, page 371; D. Swern, Org. Reactions 7 (1953), page 378).

The reaction of the compounds (Id) with (IX) is carried out, if appropriate, in the presence of a catalyst or in the presence of a basic reaction auxiliary using diluents.

Diluents which are used for carrying out process 5c according to the invention are the inert, aprotic solvents mentioned for process 3a, such as, for example, ethers, in particular methyl tert-butyl ether, tetrahydrofuran or dioxane, alcohols, in particular methanol.

All the basic reaction auxiliaries mentioned for process 5a, in particular alkali metal hydrides, can be used as reaction auxiliaries employed, if appropriate, for carrying out process 5c according to the invention.

Process 5c is carried out by reacting compounds of the general for-mula (Id) with an epoxide of the general formula (IX) in, if appropriate, the presence of a reaction auxiliary in one of the diluents mentioned.

The duration of the reaction is 4 to 72 hours. The reaction is carried out at temperatures between −10° C. and +200° C., preferably between −5° C. and +150° C., particularly preferably at 0° C. to 100° C. It can in principle be carried out under normal pressure, but also under increased or reduced pressure. The reaction is preferably carried out under normal pressure or under pressures of up to 15 bar. At higher temperatures, it is advantageous to carry out the reaction under increased pressure, if appropriate also above 15 bar.

For carrying out process 5c according to the invention, in general 0.5 to 2.0 mol, preferably 0.5 to 1.5 mol, of epoxide are employed per mol of compound of the formula (Id).

When the reaction is complete, the reaction solution is washed and the organic phase is separated off, dried and concentrated in vacuo. The products obtained can be purified in the customary manner by recrystallization, vacuum distillation or column chromatography (cf also the Preparation examples).

If 7-methyl-1, 2, 3, 4, 4aα, 5aα, 8aα, 8bα-(±)-octahydro-3α,4a-dimethyl-6H-pyrrolo[3',4': 4,5]furo[3,2-b]pyridine-6,8(7H)dione is employed as compounds of the general formula (Id) and allyl chloroformate is employed as compounds of the general formula (VII) in process 5d for the preparation of the novel 1, 2, 3, 4, 4a, 5a, 8a, 8b-octahydro-6H-pyrrolo[3',4': 4,5]furo[3,2-b]pyridine-6,8(7H)-dione derivatives of the general formula (Ib), the process can be represented by the following equation:

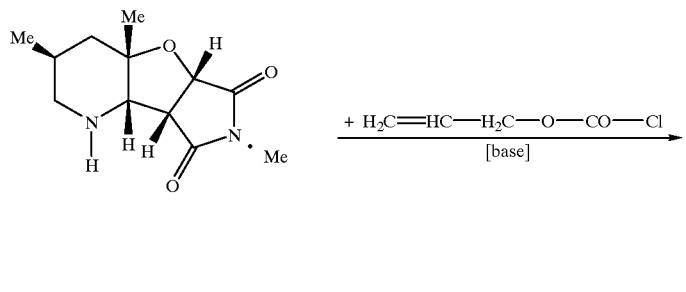 + H₂C=HC—H₂C—O—CO—Cl →[base] 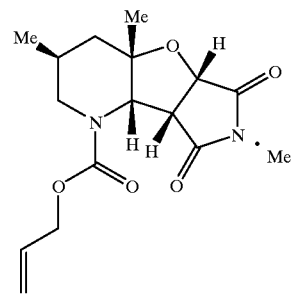

Formula (Id) provides a general definition of the 1, 2, 3, 4, 4aα, 5aα, 8aα, 8bα-(±)-octahydro-3(3α,4a-dialkyl-6H-pyrrolo[3',4': 4,5]furo[3,2-b]pyridine-6,8(7H)diones required as starting substances for carrying out process 5d according to the invention. In this formula, $R^1$, $R^2$, $R^3$ and $R^4$ preferably represent those radicals which have already been mentioned as preferred for these substituents in connection with the description of the substances of the general formula (Ib) according to the invention.

The 1, 2, 3, 4, 4aα, 5aα, 8aα, 8bα-(±)-octahydro-3α,4a-dialkyl-6H-pyrrolo[3',4': 4,5]furo[3,2-b]pyridine-6,8(7H)-diones of the general formula (Id) used as starting materials are novel and can be obtained from the 4a, 5a, 8a, 8b-tetrahydro-3,4a-dialkyl-6H-pyrrolo [3', 4': 4,5]furo [3,2-b]pyridine-6,8(7H)-dione derivatives (Ia) by the hydrogenation process described above.

Formula (X) provides a general definition of the compounds furthermore to be used as starting substances for carrying out process 5d according to the invention.

In the formula (VII), G, X, Y, and W have the meaning which have already been mentioned as preferred for these substituents in connection with the description of the substances of the general formula (Ib) according to the invention.

The compounds of the formula (X) are generally known compounds of organic chemistry, and they can be obtained in some cases commercially or by methods known from the literature (for example: persubstituted allophanic acid halides: DE-A 2 008 11 6; carbamoyl chlorides: Liebigs Ann. 299, page 85; carbamates: Houben-Weyl, Methoden der organischen Chemie [Methods of organic chemistry], Volume E 4).

The reaction of the compounds (Id) with (X) is preferably carried out in the presence of a basic reaction auxiliary using diluents.

Diluents which are used for carrying out process 5d according to the invention are the inert, aprotic solvents mentioned for process 3a, such as, for example, dioxane, acetonitrile or tetrahydrofuran, but also halogenohydrocarbons, in particular chlorohydrocarbons, such as methylene chloride.

All the acid-binding agents mentioned for process 5a can be used as basic reaction auxiliaries for carrying out process 5d according to the invention, but preferably tertiary amines, in particular trialkylamines, such as triethylamine, N,N-diisopropylethylamine, N-propyl-diisopropylamine, N,N'-dimethylcyclohexylamine or N-methylmorpholine.

Process 5d is carried out by reacting compounds of the general formula (Id) with compounds of the general formula (X) in the presence of a basic reaction auxiliary in one of the diluents mentioned.

The duration of the reaction is 4 to 72 hours. The reaction is carried out at temperatures between –10° C. and +150° C., preferably between –5° C. and +80° C., particularly preferably at 0° C. to room temperature. It is carried out under normal pressure. For carrying out process 5b according to the invention, in general 1.0 to 3.0 mol, preferably 1.0 to 1.5 mol, of acylating agent are employed per mol of compound of the formula (Id).

When the reaction is complete, the reaction solution is washed and the organic phase is separated off, dried and concentrated in vacuo. The products obtained can be purified in the customary manner by recrystallization, vacuum distillation or column chromatography (cf. also the Preparation examples).

In the compounds prepared by process 5d with a halogenoacyl (G=X for carbonyl) or halogenosulfonyl radical (G=X for sulfonyl), the halogen radical can be replaced by customary processes in a subsequent reaction with suitable nucleophiles of the general formula (XVIII) ($R^{11}$—YH), for example with amino, hydroxy or mercapto compounds.

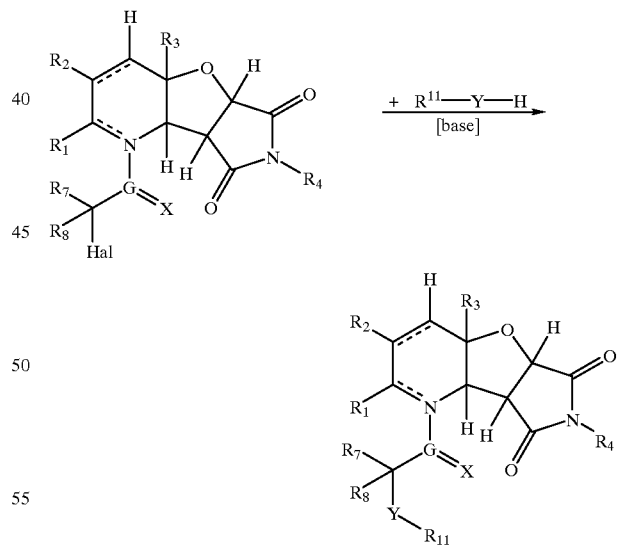

The exchange of halogen is usually carried out here in the presence of basic reaction auxiliaries under the reaction conditions customary for this reaction, and if appropriate can be accelerated by means of catalysts (cf. also the Preparation examples).

If 7-methyl-1, 2, 3, 4, 4aα, 5aα, 8aα, 8bα-(±)-octahydro-3α,4a-dimethyl-6H-pyrrolo[3',4': 4,5]furo[3,2-b]pyridine-6,8(7H)dione or 7-methyl-1, 2, 4aα, 5aα, 8aα, 8bα-(±)-hexahydro-3,4a-dimethyl-6H-pyrrolo[3',4': 4,5]furo[3,2-b]

pyridine-6,8(7H)dione is employed as compounds of the general formulae (Id) and (Ie) and diglycolic anhydride is employed as carboxylic acid anhydride of the general formula (XI) in process 5e for the preparation of the novel 1, 2, 3, 4, 4a, 5a, 8a, 8b-octahydro-6H-pyrrolo[3',4': 4,5]furo[3,2-b]pyridine-6,8(7H)-dione and/or 1, 2, 4a, 5 a, 8a, 8b-hexahydro-6H-pyrrolo[3',4': 4,5]furo[3,2-b]pyridine-6,8(7H)-dione derivatives of the general formulae (Ib) and (Ie), the process can be represented by the following equations:

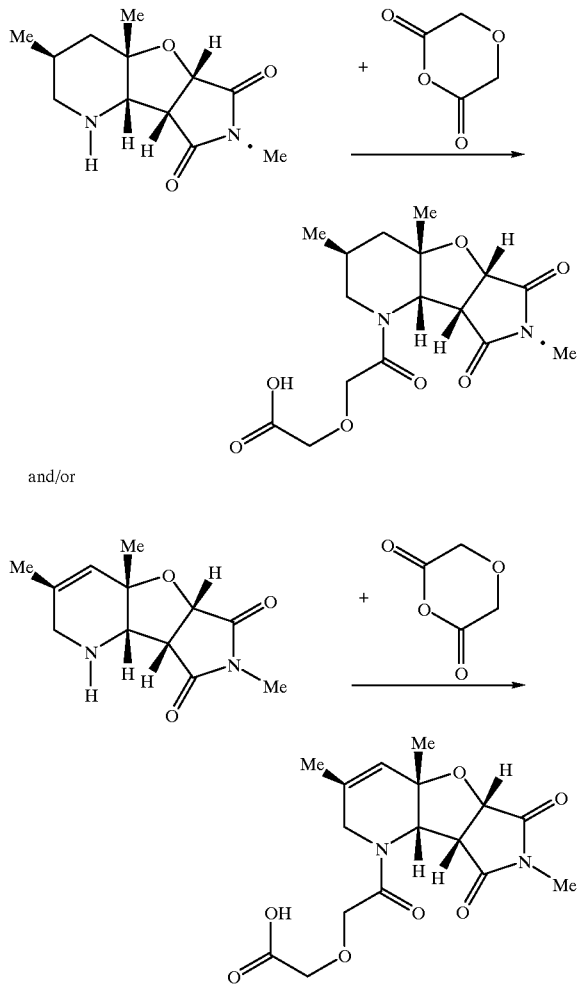

and/or

Formula (Id) and (Ie) provide a general definition of the 1, 2, 3, 4, 4aα, 5aα, 8aα, 8bα-(±)-octahydro-3α,4a-dialkyl-6H-pyrrolo[3',4': 4,5]furo[3,2-b]pyridine-6,8(7H)-dione and 1, 2, 4aα, 5aα, 8aα, 8bα-(±)-hexahydro-3,4a-dialkyl-6H-pyrrolo[3',4': 4,5]furo[3,2-b]pyridine-6,8(7H)dione required as starting substances for carrying out process 5e according to the invention. In these formulae, $R^1$, $R^2$, $R^3$ and $R^4$ pre-ferably represent those radicals which have already been mentioned as preferred for these substituents in connection with the description of the substances of the general formulae (Ib) and (Ic) according to the invention.

The 1, 2, 3, 4, 4aα, 5aα, 8aα, 8bα-(±)-octahydro-3α,4a-dialkyl-6H-pyrrolo[3',4': 4,5]furo[3,2-b]pyridine-6,8(7H)-diones and 1, 2, 4aα, 5aα, 8aα, 8bα-(±)-hexahydro-3,4a-dialkyl-6H-pyrrolo[3',4': 4,5]furo[3,2-b]pyridine-6,8(7H)dione of the general formulae (Id) and (Ie) used as starting materials are novel and can be obtained from the 4a, 5a, 8a, 8b-tetrahydro-3,4-dialkyl-6H-pyrrolo[3'4': 4,5]furo[3,2-b]pyridine-6,8(7H)-dione derivatives (Ia) by the hydrogenation processes described above.

Formula (XI) provides a general definition of the carboxylic acid anhydrides furthermore to be used as starting substances for carrying out process 5e according to the invention.

In the formula (XI), Q has the meaning which have already been mentioned as preferred for these substituents in connection with the description of the substances of the general formula (Ib) according to the invention.

The carboxylic anhydrides of the formula (XI) are generally known compounds of organic chemistry, and they can be obtained in some cases commercially or by methods known from the literature (for example: Houben-Weyl, Methoden der organischen Chemie [Methods of organic chemistry], Volume VII/4, page 120; Volume VIII, page 477).

The reaction of the compounds (Id) and/or (Ie) with (XI) is carried out, if appropriate, in the presence of a reaction auxiliary using diluents.

Diluents which are used for carrying out process 5e according to the invention are the inert, aprotic solvents mentioned for process 3a, such as, for example, ethers, in particular methyl tert-butyl ether, tetrahydrofuran or dioxane.

All the acid-binding agents mentioned for process 5a can be used as reaction auxiliaries employed, if appropriate, for carrying out process 5e according to the invention, but preferably tertiary amines, in particular trialkylamines, such as triethylamine, N,N-diisopropylethylamine, N-propyl-diisopropylamine, N,N'-dimethyl-cyclohexylamine or N-methylmorpholine.

Process 5e is carried out by reacting compounds of the general formulae (Id) and/or (Ie) with a carboxylic acid anhydride of the general formula (XI) in, if appropriate, the presence of a catalyst in one of the diluents mentioned.

Possible catalysts here are not only the basic reaction auxiliaries mentioned for process 5a but also acid catalysts. Practically all the mineral acids or Lewis acids may be mentioned as such catalysts. The mineral acids include include, preferably, hydrogen halide acids, such as hydrofluoric acid, hydrobromic acid or hydroiodic acid, and sulfuric acid, phosphoric acid, phosphorus acid, nitric acid, and the Lewis acids include, preferably, aluminum chloride, boron trifluoride or its etherate, titanium(IV) chloride, tin (IV) chloride.

The duration of the reaction is 4 to 72 hours. The reaction is carried out at temperatures between –10° C. and +250° C., preferably between –5° C. and +200° C., particularly preferably at 0° C. to 150° C. It is carried out under normal pressure. For carrying out process 5e according to the invention, in general 1.0 to 3.0 mol, preferably 1.0 to 1.5 mol, of carboxylic acid anhydride are employed per mol of compounds of the formulae (Id) and/or (Ie).

Alternatively, process 5e can also be carried out with excess carboxylic acid anhydride of the formula (XI) without a diluent, if the reaction mixture remains readily stirrable.

When the reaction is complete, the reaction solution is washed and the organic phase is separated off, dried and concentrated in vacuo. The products obtained can be purified in the customary manner by recrystallization, vacuum distillation or column chromatography (cf. also the Preparation examples).

If 7-methyl-1, 2, 3, 4, 4aα, 5aα, 8aα, 8bα-(±)-octahydro-3α,4a-dimethyl-6H-pyrrolo[3',4': 4,5]furo[3,2-b]pyridine-6, 8(7H)dione is employed as compounds of the general formula (Id) and N-benzyl-oxycarbonylsarcosine (Z-Sar-OH) is employed as amino acid derivatives of the general formula (XII) in process 5f for the preparation of the novel 1, 2, 3, 4, 4a, 5a, 8a, 8b-octahydro-6H-pyrrolo[3',4': 4,5]furo[3,2-b]-pyridine-6,8(7H)-dione derivatives of the general formula (Ib), the process can be represented by the following equation:

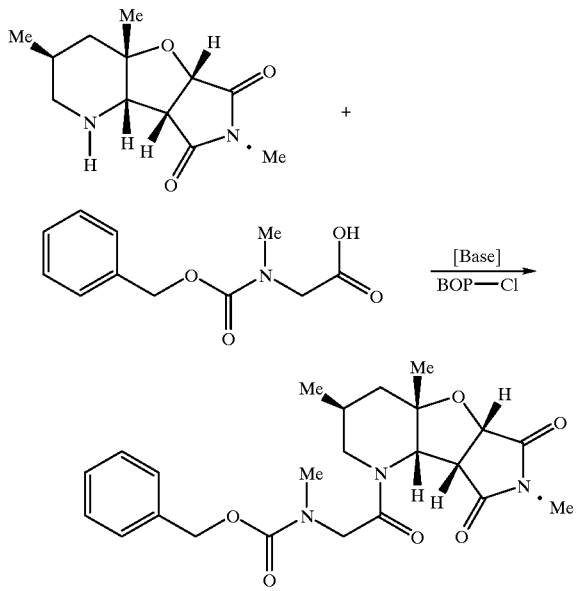

Formula (Id) provides a general definition of the 1, 2, 3, 4, 4aα, 5aα, 8aα, 8bα-(±)-octahydro-3α,4a-dialkyl-6H-pyrrolo[3',4': 4,5]furo[3,2-b]pyridine-6,8(7H)-diones required as starting substances for carrying out process 5f according to the invention. In this formula, $R^1$, $R^2$, $R^3$ and $R^4$ preferably represent those radicals which have already been mentioned as preferred for these substituents in connection with the description of the substances of the general formula (Ib) according to the invention.

The 1, 2, 3, 4, 4aα, 5aα, 8aα, 8bα-(±)-octahydro-3α,4a-dialkyl-6H-pyrrolo-[3', 4': 4,5]furo[3,2-b]pyridine-6,8(7H) diones of the general formula (Id) used as starting materials are novel and can be obtained from the 4a, 5a, 8a, 8b-tetrahydro-3,4a-dialkyl-6H-pyrrolo[3',4': 4,5]furo[3,2-b] pyridine-6,8(7H)-dione derivatives (Ia) by the hydrogenation process described above.

Formula (XII) provides a general definition of the amino acid derivatives furthermore to be used as starting substances for carrying out process 5f according to the invention.

In the formula (XII), G, Q, X, $R^6$, $R^7$ and $R^8$ have the meaning which have already been mentioned as preferred for this substituent in connection with the description of the substances of the general formula (Ib) according to the invention.

The naturally occurring or synthetic amino acids used as starting substances can be in the (S) or (R) form (or L or D form), if they are chiral.

Examples which may be mentioned are:

Aad, Abu, jAbu, ABz, 2ABz, εAca, Ach, Acp, Adpd, Ahb, Aib, βAib, Ala, βAla, ΔAla, Aig, All, Ama, Amt, Ape, Apm, Apr, Arg, Asn, Asp, Asu, Aze, Azi, Bai, Bph, Can, Cit, Cys, (Cys)₂, Cyta, Daad, Dab, Dadd, Dap, Dapm, Dasu, Djen, Dpa, Dtc, Fel, Gln, Glu, Gly, Guv, hAla, hArg, hCys, hGln, hGlu, His, hile, hLeu, hLys, hMet, hPhe, hPro, hSer, hThr, hTrp, hTyr, Hyl, Hyp, 3Hyp, Ile, Ise, Iva, Kyn, Lant, Lcn, Leu, Lsg, Lys, βLys, ΔLys, Met, Mim, Min, nArg, Nle, Nva, Oly, Orn, Pan, Pec, Pen, Phe, Phg, Pic, Pro, ΔPro, Pse, Pse, Pya, Pyr, Pza, Qin, Ros, Sar, Sec, Sem, Ser, Thi, βThi, Thr, Thy, Thx, Tia, Tle, Tly, Trp, Trta, Tyr, Val, Nal, Tbg, Npg, Chg, Thia (cf. for example, Houben-Weyl, Methoden der Organischen Chemie, [Methods of organic chemistry], Volume XV/1 and 2, Stuttgart, 1974).

The compounds of the formula (XII) can be obtained in some cases commercially or by methods known from the literature (cf., for example: N-methylamino acids: R. Bowmann et al. J. Chem. Soc. (1950) page 1346; J. R. McDermott et al Can J. Chem. 51 (1973) page 1915;H.Wurziger et al. Kontakte (Merck, Darmstadt) 3 (1987) page 8).

The reaction of the 1, 2, 3, 4, 4aα, 5aα, 8aα, 8bα-(±)-octahydro-3α,4a-dialkyl-6H-pyrrolo[3',4': 4,5]furo[3,2-b]pyridine-6,8(7H)-diones of the general formula (Ic) with amino acid derivatives of the formula (XII) is preferably carried out in the presence of coupling reagents and in the presence of a basic reaction auxiliary using diluents.

Coupling reagents which are used for carrying out process 5f are all those which are suitable for establishing an amide bond (cf., for example: Houben-Weyl, Methoden der organischen Chemie [Methods of organic chemistry], Volume 15/2; Bodanszky et al., Peptide Synthesis 2nd ed. (Wiley & Sons, New York 1976) or Gross, Meienhofer, The Peptides: Analysis Synthesis, Biology (Academic Press, New York 1979). The following methods are preferably used: active ester method with pentachloro-(Pcp) and pentafluorophenyl (Pfp), N-hydroxysuccinimide, N-hydroxy-5-norbonene-2,3-dicarbox-amide (HONB), 1-hydroxy-benzotriazole (HOBt) or 3-hydroxy-4-oxo-3,4-dihydro-1,2,3-benzotriazine as the alcohol component, coupling with carbodiimides, such as dicyclo-hexyl-carbodiimide (DCC) by the DCC additive process, or with n-propanephos-phonic anhydride (PPA) and the mixed anhydride method with pivaloylchloride, ethyl (EEDQ) and isobutyl chloroformate (IIDQ) or coupling with phosphonium reagents, such as benzotriazol-1-yl-oxy-tris (dimethylamino-phosphonium) hexafluorophosphate (BOP), bis(2-oxo-3-oxazolidinyl)phosphonium acid chloride (BOP-CI), or with phosphonic acid ester reagents, such as diethyl cyanophosphonate (DEPC) and diphenylphosphoryl azide (DPPA) or uronium reagents, such as 2-(1H-benzotriazol-1-yl)-1,1,3,3-tetra-methyluronium tetrafluoroborate (TBTU).

Coupling with phosphonium reagents such as bis(2-oxo-3-oxazolidinyl)-phosphonium acid chloride (BOP-CI), benzotriazol-1-yl-oxy-tris(dimethylamino-phosphonium) hexafluorophosphate (BOP) and phosphonic acid ester reagents, such as diethyl cyanophosphonate (DEPC) or diphenylphosphoryl azide (DPPA) is preferred.

All acid-binding agents suitable for process 5a can likewise be employed as basic reaction auxiliaries for carrying out process 5f according to the invention.

Tertiary amines, in particular trialkylamines, such as triethylamine, N,N-diisopropylethylamine, N-propyl-diisopropylamine, N,N'-dimethyl-cyclohexylamine or N-methylmorpholine are preferably suitable.

Diluents which are used for carrying out process 5f according to the invention are the solvents mentioned for process 3a, such as, for example, halogenohydrocarbons, in particular chlorohydrocarbons, such as methylene chloride or 1,2-dichloroethane, and mixtures of these with other mentioned diluents.

Process 5f is in general carried out in such a way by compounds of the formula (Id) with compounds of the general formula (XII) in the presence of one of the coupling reagents mentioned and in the presence of one of the basic reaction auxiliaries mentioned in one of the diluents mentioned. The duration of the reaction is 4 to 72 hours. The reaction is carried out at temperatures between −10° C. and +120° C., preferably between −5° C. and +50° C., particularly preferably at 0° C. to room temperature. It is carried out under normal pressure.

For carrying out process 5f according to the invention, in general 1.0 to 3.0 mol, preferably 1.0 to 1.5 mol of coupling reagent are employed per mol of 1, 2, 3, 4, 4aα, 5aα, 8aα, 8bα-(±)-octahydro-3α,4a-dialkyl-6H-pyrrolo-[3',4': 4,5] furo[3,2-b] pyridine-6,8(7H)-diones of the formula (Id).

When the reaction is complete, the reaction solution is washed and the organic phase is separated off, dried and concentrated in vacuo. The products obtained can be purified in the customary manner by recrystallization, vacuum distillation or column chromatography (cf. also the Preparation examples).

If 7-methyl-1, 2, 3, 4, 4aα, 5aα, 8aα, 8bα-(±)octahydro-3α,4a-dimethyl-6H-pyrrolo-[3',4': 4,5]furo[3,2-b]pyri-dine-6,8(7H)dione is employed as compounds of the general formula (Id) and trichloroacetyl isocyanate is employed as compounds of the general formula (XIII) in process 5g for the preparation of the of the novel 1, 2, 3, 4, 4a, 5a, 8a, 8b-octahydro-6H-pyrrolo[3',4': 4,5]furo[3,2-b]pyridine- 6,8 (7H)-dione derivatives of the general formula (Ib), the process can be represented by the following equation:

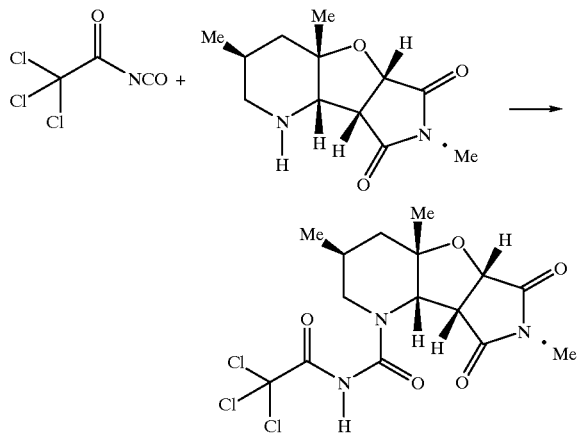

Formula (Id) provides a general definition of the 1, 2, 3, 4, 4aα, 5aα8aα, 8bα-(±)-octahydro-3α, 4a-dialkyl-6H-pyrrolo[3',4': 4,5]furo[3,2-b]pyridine-6,8(7H)-diones required as starting substances for carrying out process 5g according to the invention. In this formula, $R^1$, $R^2$, $R^3$ and $R^4$ preferably represent those radicals which have already been mentioned as preferred for these substituents in connection with the description of the substances of the general formula (Ib) according to the invention.

The 1, 2, 3, 4, 4aα, 5aα, 8aα, 8bα-(±)-octahydro-3α, 4a-dialkyl-6H-pyrrolo[3',4': 4,5]furo[3,2-b]pyridine-6,8 (7H)-diones of the general formula (Id) used as starting materials are novel and can be obtained from the 4a, 5a, 8a, 8b-tetrahydro-3,4a-dialkyl-6H-pyrrolo[3',4': 4,5]furo[3,2-b] pyridine-6,8(7H)-dione derivatives (Ia) by the hydrogenation process described above.

Formulae (XIII) and (XIV) provide general definitions of the compounds furthermore to be used as starting substances for carrying out the process 5g according to the invention.

In the formulae (XIII) and (XIV), $R^{11}$, Y, $G^1$, $X^1$ and X have the meaning which have already been mentioned as preferred for these substituents in connection with the description of the substances of the general formula (Ib) according to the invention.

The compounds of the formulae (XIII) and (XIV) are generally known compounds of organic chemistry, and can be obtained in some cases commercially or by methods known from the literature (Houben-Weyl, Methoden der organischen Chemie [Methods of organic chemistry], Volume E 4).

The reaction of the compounds (Id) with (XIII) or (XIV) by process 5f according to the invention is preferably carried out in the presence of diluents, if appropriate in the presence of a basic reaction auxiliary.

Diluents which are used for carrying out process 5g according to the invention are the solvents mentioned for process 3a, such as, for example, nitriles, such as acetonitrile, propionitrile, butyronitrile, in particular acetonitrile, and ethers, such as ethylpropyl ether, n-butyl ether, diethyl ether, dipropyl esther, diisopropyl ether, di-n-butyl ether, diisobutyl ether, diisoamyl ether, tetrahydrofuran, dioxane, in particular tetrahydrofuran and dioxane.

Process 5g can also be carried out in the presence of basic reaction auxiliaries. All the acid-binding agents mentioned for process 5a can be used as such basic reaction auxiliaries for carrying out process 5g according to the invention, but preferably tertiary amines, in particular trialkylamines, such as triethylamine, N,N-diisopropylethylamine or N-methylmorpholine, and amidine bases or guanidine bases, such as diazabicyclo-(4.3.0)nonene (DBN), diazabicyclo (2.2.2)-octane (DABCO), 1,8-diaza-bicyclo(5.4.0)-undecene (DBU) in particular 1,8-diazabicyclo(5.4.0)-undecene (DBU).

Process 5g is carried out by bringing together compounds of the general formula (Id) with equimolar amounts of a compound of the formulae (XIII) or (XIV) in one of the diluents mentioned above, if appropriate in the presence of a basic reaction auxiliary. The duration of the reaction is 1 to 72 hours. The reaction is carried out at temperatures between −50° C. to +200° C., preferably in a temperature range between −20° C. and +150° C., in particular in a temperature range between −10° C. and +120° C.

The reaction can in principle be carried out under normal pressure, but it can also be carried out under increased or reduced pressure. It is preferably carried out under normal pressure or under pressures of up to 15 bar. At higher temperatures, it is advantageous to carry out the reaction under increased pressure, if appropriate also above 15 bar.

When the reaction is complete, the reaction mixture is worked up by generally customary methods (cf also the Preparation examples).

Processes for the preparation of organic carbamates from an amine giving a basic reaction, carbon dioxide and an alkylating agent in the presence of basic alkali metal, alkaline earth metal or ammonium salts are known (cf. EP-A 511 948, EP-A 628 542 and literature cited therein).

It has now been found that the basic 1, 2, 3, 4, 4a, 5a, 8a, 8b-octahydro-6H-pyrrolo[3',4': 4,5]furo[3,2-b]pyridine-6,8 (7H)-dione and/or 1, 2, 4a, 5a, 8a, 8b-hexahydro-6H-pyrrolo [3',4': 4,5]furo[3,2-b]pyridine-6,8(7H)-dione derivatives of the general formulae (Id) and (Ie) according to the invention also react, as secondary amino compounds, with carbon dioxide and an alkylating agent in the presence of metal carbonates to give carbamates of the general formula (Ib) and (Ic).

If 7-methyl-1, 2, 3, 4, 4aα, 5aα, 8aα, 8bα-(±)-octahydro-3α, 4a-dimethyl-6H-pyrrolo-[3',4': 4,5]furo[3,2-b]pyridine-6,8(7H)-dione, is employed as compounds of the general formula (Id), carbon dioxide and potassium carbonate are employed, and propargyl bromide is employed as compounds of the general formula (VIIa) in process 5h for the preparation of the novel 1, 2, 3, 4, 4a, 5a, 8a, 8b-octahydro-6H-pyrrolo[3',4': 4,5]furo[3,2-b]pyridine-6,8(7H)dione derivatives of the general formula (Ib), the process can be represented by the following equation:

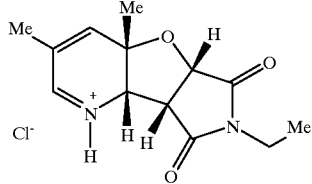

The 1, 2, 3, 4, 4a, 5a, 8a, 8b-octahydro-6H-pyrrolo[3', 4': 4,5] furo[3,2-b]pyridine-6,8(7H)-dione derivatives of the general formula (Id) in which the radicals $R^1$, $R^2$, $R^3$ and $R^4$ have the preferred and particularly preferred meanings in the case of the compounds of the general formula (Ib) are preferably employed in process 5h.

The 1, 2, 3, 4, 4aα5aα, 8aα, 8bα-(±)-octahydro-3α,4a-dialkyl-6H-pyrrolo[3',4': 4,5]furo[3,2-b]pyridine-6,8(7H)-diones of the general formula (Id) used as starting materials are novel and can be obtained from the 4a, 5a, 8a, 8b-tetrahydro-3,4-dialkyl-6H-pyrrolo[3',4': 4,5]furo [3,2-b] pyridine-6,8(7H)-dione derivatives (Ia) by the hydrogenation process described above.

The usual commercial product, if appropriate also so-called "dry ice", can be employed as carbon dioxide in the process according to the invention.

The alkylating agents of the formula (VIIa) furthermore to be used as starting substances for carrying out process 5h according to the invention are generally known compounds of organic chemistry.

In the formula (VIIa), $R^{11}$ has the meaning which has already been mentioned as preferred for this substituent in connection with the description of the substances of the general formula (Ib) according to the invention, and Hal has the meaning of an electron-withdrawing leaving group.

Suitable leaving groups are, for example, halogen, such as fluorine, chlorine, bromine and iodine, sulfonate, such as aryl- and perfluoroalkylsulfonate, monosubstituted diazo and monosubstituted nitrato, and those additionally listed in J. March, Advanced Organic Chemistry, 3rd ed., John Wiley & Sons, New York 1985, pages 310–316.

Compounds which give a basic reaction and can be used in the present invention are one or more basic compounds of the elements lithium, sodium, magnesium, potassium, calcium, rubidium, strontium, cesium, barium, and/or of ammonium. Possible basic compounds are, for example, salts, oxides, hydrides and hydroxides which give a basic reaction. Examples which may be mentioned are: lithium hydride, sodium hydride, potassium hydride, calcium hydride, lithium hydroxide, sodium hydroxide, potassium hydroxide, rubidium hydroxide, magnesium hydroxide, calcium hydroxide, strontium hydroxide, barium hydroxide, lithium oxide, sodium peroxide, potassium oxide, potassium peroxide, calcium oxide, barium oxide, magnesium oxide, strontium oxide, lithium carbonate, lithium bicarbonate, rubidium carbonate, rubidium bicarbonate, cesium bicarbonate, cesium carbonate, lithium cyanide, sodium cyanide, potassium cyanide, rubidium cyanide, ammonium bicarbonate, cesium carbonate, ammoni-um carbamate, potassium sulfide, potassium hydrogensulfide, sodium sulfide, sodium hydrogensulfide and/or naturally occurring or synthetically obtainable mixtures thereof, such as, for example, dolomite or magnesium oxide carbonate and/or compounds which contain sodium or potassium metal on the corresponding carbonates in dispersed However, alkali metal carbonates and/or bicarbonates, especially preferably cesium carbonate or potassium carbonate, are preferred.

The compounds which give a basic reaction can be employed in anhydrous form or, if they are salts which crystallize with water of hydration, in hydrated form. Preferably, however, anhydrous compounds are used.

Diluents which are used for carrying out process 5h according to the invention are the solvents mentioned for process 3a, such as, for example, amides, such as hexamethylenephosphorotriamide, N,N-dimethylformamide, N,N-dipropylformamide, N,N-dibutylformamide, N-methyl-pyrrolidone or N-methyl-caprolactam, in particular N,N-dialkylformamides, such as N,N-dimethyl-formamide, and sulfoxides, such as dimethyl sulfoxide, tetramethylene sulfoxide, dipropyl sulfoxide, benzylmethyl sulfoxide, diisobutyl. sulfoxide, dibutyl sulfoxide, diusoamyl sulfoxide, in particular dimethyl sulfoxide.

Alternatively, process 5h can also be carried out in the presence of basic reaction auxiliaries, i.e. in the presence of further bases, for example in an amount of less than 0.5 mol, based on the base employed.

All the acid-binding agents mentioned for process 5a can as such basic reaction auxiliaries for carrying out process 5h according to the invention, but preferably tertiary amines, in particular trialkylamines, such as triethylamine, N,N-diisopropylethylamine or N-methylmorpholine, and amidine bases or guanidine bases, such as 7-methyl-1,5,7-triazabicyclo-(4.4.0)dec-5-ene (MTBD); diazabicyclo-(4.3.0)nonene (DBN), diazabicyclo-(2.2.2)octane (DABCO), 1,8-diazabicyclo(5.4.0)-undecene (DBU) cyclo-hexyltetrabutylguanidine (CyTBG), cyclohexyltetrameth-ylguanidine (CyTMG), cyclohexyltetrabutylguanidine, N,N,N,N-tetramethyl-1,8-naphthalenediamine, in particular cyclohexyltetra-methylguanidine (CyTMG) and cyclohexy-ltetrabutylguanidine (CyTBG), use.

Process 5h is carried out by bringing together compounds of the general formula (Id) in the presence of carbon dioxide, a 2- to 3-fold excess of alkali metal carbonate of the formula (XV) and an alkylating agent of the formula (VIIa) in one of the diluents mentioned above for process 3a, if appropriate in the presence of a basic reaction auxiliary, at room temperature. In a second reaction step, the alkylation of the alkali metal salts of the formulae (XVI) and (XVII), formed in situ, with compounds of the formula (V11a) is carried out over a reaction time of I to 72 hours and a reaction temperature between −50° C. and +180° C., preferred temperatures being in the range between −30° C. and +150° C., in particular those in the range of −10° C. to +100° C.

The reaction can in principle be carried out under normal pressure, but it can also be carried out under increased or reduced pressure. Preferably, it is carried out under normal pressure or under pressures of up to 15 bar. At higher temperatures it is advantageous to carry out the reaction under increased pressure, if appropriate also above 15 bar.

The reaction products are worked up and isolated by generally customary methods (cf. also the Preparation examples).

If 1-(4-nitrophenoxy-carbonyl)-7-methyl-1, 2, 3, 4, 4aα, 5aα, 8aα, 8bα-(±)-octahydro-3α,4a-dimethyl-6H-pyrrolo[3',4': 4,5]furo[3,2-b] pyridine-6,8(7H)-dione is employed as compounds of the general formula (If) anr morpholine is employed as the nucleophile of the general formula (XVIII) in process 5i for the preparation of the novel 1, 2, 3, 4, 4a, 5a, 8a, 8b-octahydro-6H-pyrrolo[3',4': 4,5]furo[3,2-b]pyridine-6,8(7H)-dione derivatives of the general formula (Ib), the process can be represented by the following equation:

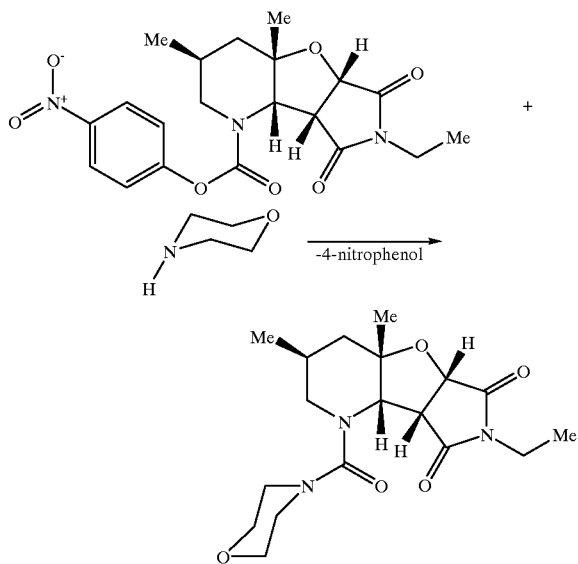

The general formula (If) provides a general definition of the 1, 2, 3, 4, 4a, 5a, 8a, 110 8b-octahydro-6H-pyrrolo[3',4': 4,5]furo[3,2-b]pyridine-6,8(7H)-dione derivatives required as starting substances for carrying out process 5i according to the invention. In this formula, $R^1$, $R^2$, $R^3$, $R^4$, $R^5$, G, W and X preferably represent those radicals which have already been mentioned as preferred for these substituents in connection with the description of the substances of the general formula (If) according to the invention.

The 1, 2, 3, 4, 4a, 5a, 8a, 8b-octahydro-6H-pyrrolo[3',4': 4,5]furo[3,2-b]pyridine 6,8(7H)-dione derivatives of the general formula (If) used as starting materials can be prepared by process 5d according to the invention already described above.

The nucleophilic agents of the formula (XVIII) furthermore to be used as starting substances for carrying out process 5i according to the invention are generally known compounds of organic chemistry, and they can be obtained in some cases commercially. In the formula (XVIII), $R^{11}$ and Y have the meaning which have already been mentioned as preferred in connection with the description of the substances of the general formula (Ib) according to the invention.

Process 5i is carried out by reacting compounds of the general formula (If) in the presence of a nucleophilic agent of the formula (XVIII) in one of the diluents mentioned above. The duration of the reaction is 4 to 72 hours. The reaction is carried out at temperatures between +10° C. and +200° C., preferably between +20° C. and +150° C., particularly preferably at the boiling point of the diluent.

The reaction can in principle be carried out under normal pressure, but it can also be carried out under increased or reduced pressure. It is preferably carried out under normal pressure or under pressures of up to 15 bar. At higher temperatures, it is advantageous to carry out the reaction under increased pressure, if appropriate also above 15 bar.

When the reaction is complete, the reaction solution is washed and the organic phase is separated off, dried and concentrated in vacuo. The products obtained can be purified in the customary manner by recrystallization, vacuum distillation or column chromatography (cf. also the Preparation examples).

Compounds according to the invention are obtainable with processes 5a to 5i according to the invention from the individual units with both the (S) and the (R) configuration (or L and D configuration), retaining the original configuration of the starting substances.

The "inert solvents" referred to in the above process variants 5a to 5i are taken in each case to mean solvents which are inert under the particular reaction conditions, but do not have to be inert under any desired reaction conditions.

The active compounds are suitable for controlling pathogenic endoparasites which occur in humans and in stock, breeding, zoo, laboratory and test animals and pets in animal husbandry and animal breeding, having favorable toxicity to warm-blooded animals. They are active here against all or individual stages of development of the pests and against resistant and normally sensitive species. By controlling the pathogenic endoparasites, disease, fatalities and reductions in productivity (for example in the production of meat, milk, wool, hides, eggs, honey and the like) are to be diminished, so that more economic and easier animal husbandry is possible by use of the active compounds. The pathogenic endoparasites include cestodes, trematodes, nematodes, acantocephalae, in particular:

From the order of the Pseudophyllidea, for example: Diphyllobothrium spp., Spirometra spp., Schistocephalus spp., Ligula spp., Bothridium spp., Diphlogonoporus spp.

From the order of the Cyclophyllidea, for example: Mesocestoides spp., Anoplocephala spp., Paranoplocephala spp., Moniezia spp., Thysanosomsa spp., Thysaniezia spp., Avitellina spp., Stilesia spp., Cittotaenia spp., Andyra spp., rF, Bertiella spp., Taenia spp., Echinococcus spp., Hydatigera spp., Davainea spp., Raillietina spp., Hymenolepis spp., Echinolepis spp., Echinocotyle spp., Diorchis spp., Dipylidium spp., Joyeuxiella spp., Diplopylidium spp.*

From the subclass of the Monogenea, for example: Gyrodactylus spp., Dactylogyrus spp., Polystoma spp. From the subclass of the Digenea, for example: Diplostomum spp., Posthodiplostomum spp., Schistosoma spp., Trichobilharzia spp., Ornithobilharzia spp., Austrobilharzia spp., Gigantobilharzia spp., Leucochloridium spp., Brachylaima spp., Echinostoma spp., Echinoparyphium spp., Echinochasmus spp., Hypoderaeum spp., Fasciola spp., Fasciolides spp., Fasciolopsis spp., Cyclocoelum spp., Typhlocoelum spp., Paramphistomum spp., Calicophoron spp., Cotylophoron spp., Gigantocotyle spp., Fischoederius spp., Gastrothylacus spp., Notocotylus spp., Catatropis spp., Plagiorchis spp., Prosthogonimus spp., Dicrocoelium spp., Eurytrema spp., Troglotrema spp., Paragonimus spp., Collyriclum spp., Nanophyetus spp., Opisthorchis spp., Clonorchis spp., Metorchis spp., Heterophyes spp., Metagonismus spp.

From the order of the Enoplida, for example: Trichuris spp., Capillaria spp., Trichomosoides spp., Trichinella spp.

From the order of the Rhabditia, for example: Micronema spp., Strongyloides spp.

From the order of the Strongylida, for example: Stronylus spp., Triodontophorus spp., Oesophagodontus spp., Trichonema spp., Gyalocephalus spp., Cylindropharynx spp., Poteriostomum spp., Cyclococercus spp., Cylicostephanus spp., Oesophagostomum spp., Chabertia spp., Stephanurus spp., Ancylostoma spp., Uncinaria spp., Bunostomum spp., Globocephalus spp., Syngamus spp., Cyathostoma spp., Metastrongylus spp., Dictyocaulus spp., Muellerius spp., Protostrongylus spp., Neostrongylus spp., Cystocaulus spp., Pneumostrongylus spp., Spicocaulus spp., Elaphostrongylus spp., Parelaphostrongylus spp., Crenosoma spp., Paracrenosoma spp., Angiostrongylus spp., Aelurostrongylus spp., Filaroides spp., Parafilaroides spp., Trichostrongylus spp., Haemonchus spp., Ostertagia spp., Marshallagia spp., Cooperia spp., Nematodirus spp., Hyostrongylus spp., Obeliscoides spp., Amidostomum spp., Ollulanus spp.

From the order of the Oxyurida, for example: Oxyuris spp., Enterobius spp., Passalurus spp., Syphacia spp., Aspiculuris spp., Heterakis spp.

From the order of the Ascaridia, for example: Ascaris spp., Toxascaris spp., Toxocara spp., Parascaris spp., Anisakis spp., Ascaridia spp.

From the order of the Spirurida, for example: Gnathostoma spp., Physaloptera spp., Thelazia spp., Gongylonema spp., Habronema spp., Parabronema spp., Draschia spp., Dracunculus spp.

From the order of the Filariida, for example: Stephanofilaria spp., Parafilaria spp., Setaria spp., Loa spp., Dirofilaria spp., Litomosoides spp., Brugia spp., Wuchereria spp., Onchocerca spp.

From the order of the Gigantorhynchida, for example: Filicollis spp., Moniliformis spp., Macracanthorhynchus spp., Prosthenorchis spp.

The stock and breeding animals include mammals, such as, for example, cattle, horses, sheep, pigs, goats, camels, water buffalo, donkeys, rabbits, fallow deer, reindeer, fur-bearing animals, such as, for example, mink, chinchillas, racoons, birds, such as, for example, chickens, geese, turkeys, ducks, fresh water and salt-water fishes, such as, for example, trout, carp, eels, reptiles, insects, such as, for example, honey bees and silk worms.

Laboratory and test animals include mice, rats, guinea-pigs, golden hamsters, dogs and cats.

Pets include dogs and cats.

The compounds can be used both prophylactically and therapeutically.

The active compounds are used, directly or in the form of suitable formulations, enterally, parenterally, dermally, nasally, by treatment of the environment or with the aid of molded articles containing the active compound, such as, for example, strips, sheets, tapes, collars, ear marks, limb tapes, marking devices.

Enteral use of the active compounds is effected, for example, orally, in the form of powders, tablets, capsules, pastes, drinks, granules, orally administerable solutions, suspensions and emulsions, boli, medicated feed or drinking water. Fr Dermal use is effected, for example, in the form of dips, sprays or pour-on and spot-on formulations. Parenteral use is effected, for example, in the form of injection (intramuscular, subcutaneous, intravenous, intraperitoneal) or by implants.

Suitable formulations are:

Solutions, such as injection solutions, oral solutions, concentrates for oral administration after dilution, solutions for use on the skin or in body cavities, pouron formulations, gels;

emulsions and suspensions for oral or dermal use and for injection; semi-solid formulations;

formulations in which the active compound is processed in an ointment base or in an oil-in-water or water-in-oil emulsion base;

Solid formulations, such as powders, premixes or concentrates, granules, pellets, tablets, boli, capsules; aerosols and inhalates, molded articles containing the active compound.

Injection solutions are administered intravenously, intramuscularly and subcutaneously.

Injection solutions are prepared by dissolving the active compound in a suitable solvent and if necessary adding additives, such as solubilizing agents, acids, bases, buffer salts, antioxidants, preservatives. The solutions are subjected to sterile filtration and bottled.

Solvents which may be mentioned are: physiologically tolerated solvents, such as water, alcohols, such as ethanol, butanol, benzyl alcohol, glycerol, propylene glycol, polyethylene glycols, N-methyl-pyrrolidone, and mixtures thereof.

If appropriate, the active compounds can also be dissolved in physiologically tolerated vegetable or synthetic oils which are suitable for injection.

Solubilizing agents which may be mentioned are: solvents which promote solution are the active compound in the main solvent or prevent its precipitation. Examples are polyvinylpyrrolidone, polyoxyethylated castor oil, polyoxyethylated sorbitan esters.

Preservatives are: benzyl alcohol, trichlorobutanol, p-hydroxybenzoic acid esters, n-butanol.

Oral solutions are used directly. Concentrates are used orally after prior dilution to the use concentration. Oral solutions and concentrates are prepared as described above for the injection solutions, but sterile working can be omitted.

Solutions for use on the skin are dripped on, brushed on, massaged in, sprinkled on or sprayed on. These solutions are prepared as described above for the injection solutions.

It may be advantageous to add thickeners during the preparation. Thickeners are: inorganic thickeners, such as bentonites, colloidal silicic acid, aluminum monostearate, organic thickeners, such as cellulose derivatives, polyvinyl alcohols and copolymers thereof, acrylates and methacrylates.

Gels are applied to or spread on the skin or introduced into body cavities. Gels are prepared by adding to solutions which have been prepared as described for the injection solutions, an amount of thickeners such that a clear composition having an ointment-like consistency is formed. The thickeners mentioned above are employed as thickeners.

Pour-on formulations are poured or sprayed on to limited areas of the skin, the active compound penetrating through the skin and acting systemically.

Pour-on formulations are prepared by dissolving, suspending or emulsifying the active compound in suitable solvents or solvent mixtures tolerated by the skin. If appropriate, further auxiliaries, such as colorants, absorption-promoting substances, antioxidants, light stabilizers, adhesives, are added.

Solvents which may be mentioned are: water, alkanols, glycols, polyethylene glycols, polypropylene glycols, glycerol, aromatic alcohols, such as benzyl alcohol, phenylethanol, phenoxyethanol, esters, such as ethyl acetate, butyl acetate, benzyl benzoate, ethers, such as alkylene glycol alkyl ethers, such as dipropylene glycol monomethyl ether, diethylene glycol mono-butyl ether, ketones, such as acetone, methyl ethyl ketone, aromatic and/or aliphatic hydrocarbons, vegetable or synthetic oils, DMF, dimethylacetamide, N-methylpyrrolidone, 2,2-dimethyl-4-oxymethylene-1,3-dioxolane.

Colorants are all the colorants which are approved for use on animals and can be dissolved or suspended.

Absorption-promoting substances are, for example, DMSO, spreading oils, such as isopropyl myristate, dipropylene glycol pelargonate, silicone oils, fatty acid esters, triglycerides, fatty alcohols.

Antioxidants are sulfites are metabisulfites, such as potassium metabisulfite, ascorbic acid, butylhydroxytoluene, butylhydroxyanisole, tocopherol.

Light stabilizers are, for example, novantisole acid.

Adhesives, are for example, cellulose derivatives, starch derivatives, polyacrylates, naturally occurring polymers, such as alginates, gelatin.

Emulsions can be used orally, dermally or as injections.

Emulsions are either of the water-in-oil type or of the oil-in-water type.

They are prepared by dissolving the active compound either in the hydrophobic or in the hydrophilic phase and homogenizing this solution with the solvent of the other phase with the aid of suitable emulsifiers and if appropriate other auxiliaries, such as colorants, absorption-promoting substances, preservatives, antioxidants, light stabilizers, viscosity-increasing substances.

Hydrophobic phases (oils) which may be mentioned are: paraffin oils, silicone oils, naturally occurring plant oils, such as sesame oil, almond oil, castor oil, synthetic triglycerides, such as caprylic/capric acid biglyceride, a triglyceride mixture with plant fatty acids of chain length $C_{8-12}$ or other specially selected naturally occurring fatty acids, partial glyceride mixtures of saturated or unsaturated fatty acids, which may also contain hydroxyl groups, mono- and diglycerides of $C_8/C_{10}$-fatty acids.

Fatty acid esters, such as ethylstearate, di-n-butyryl adipate, hexyl laurate, dipropylene glycol pelargonate, esters of a branched fatty acid of medium chain length with saturated fatty alcohols of chain length $C_{16}$–$C_{18}$, isopropylmyristate, isopropylpalmitate, caprylic/capric acid esters of saturated fatty alcohols of chain length $C_{12}$–$C_{18}$, isopropylstearate, oleyl oleate, decyl oleate, ethyl oleate, ethyl lactate, waxy fatty acid esters, such as synthetic duck uropygeal gland fat, dibutyl phthalate, diisopropyl adipate, ester mixtures related to the latter and others.

Fatty alcohols, such as isotridecyl alcohol, 2-octyldodecanol, cetylstearyl alcohol, oleyl alcohol.

Fatty acids, such as, for example, oleic acid and its mixtures.

Hydrophilic phases which may be mentioned are:
water, alcohols, such as, for example, propylene glycol, glycerol, sorbitol and their mixtures.

Emulsifiers which may be mentioned are: nonionic surfactants, for example polyoxyethylated castor oil, polyoxyethylated sorbitan monooleate, sorbitan monostearate, glycerol monostearate, polyoxyethylstearate, alkylphenol polyglycol ethers,
ampholytic surfactants, such as di-Na N-lauryl-p-iminodipropionate or lecithin;
anionic surfactants, such as Na lauryl sulfate, fatty alcohol ether-sulfates, mono/dialkyl polyglycol ether orthophosphoric acid ester monoethynolamine salt.

Further auxiliaries which may be mentioned are: viscosity-increasing and emulsion-stabilizing substances, such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silicic acid or mixtures of the substances listed.

Suspensions can be used orally, dermally or as an injection. They are prepared by suspending the active compound in a carrier liquid, if appropriate with the addition of other auxiliaries, such as wetting agents, colorants, absorption-promoting substances, preservatives, antioxidant light stabilizers.

Carrier liquids which may be mentioned are all the homogeneous solvents and solvent mixtures.

Wetting agents (dispersing agents) which may be mentioned are the surfactants mentioned above.

Other auxiliaries which may be mentioned are those mentioned above.

Semi-solid formulations can be administered orally or dermally. They differ from the suspensions and emulsions described above only in their higher viscosity.

To prepare solid formulations, the active compound is mixed with suitable carrier substances, if appropriate with the addition of auxiliaries, and the mixture is brought into the desired shape.

Carrier substances which may be mentioned are all the physiologically tolerated solid inert substances. Inorganic or organic substances serve as such inert substances. Inorganic substances are, for example, sodium chloride, carbonates, such as calcium carbonate, bicarbonates, aluminum oxides, silicic acids, aluminas, precipitated or colloidal silicon dioxide, phosphates.

Organic substances are, for example, sugars, cellulose, foodstuffs and feedstuffs, such as milk powder, animal flours, cereal flours and shredded cereals, starches.

Auxiliaries are preservatives, antioxidants, dyestuffs, which have already been listed above.

Other suitable auxiliaries are lubricants and slip agents, such as, for example, magnesium stearate, stearic acid, talc, bentonites, substances which promote disintegration, such as starch or crosslinked polyvinylpyrrolidone, binders, such as, for example, starch, gelatin or linear polyvinylpyrrolidone, and dry binders, such as microcrystalline cellulose.

The active compounds can also be present in the formulations as a mixture with synergists or with other active compounds which act against pathogenic endoparasites. Such active compounds are, for example, L-2,3,5,6-tetrahydro-6-phenylimidazothiazole, benzimidazole-carbamates, prazi-quantel, pyrantel, febantel.

Ready-to-use formulations comprise the active compound in concentrations of 10 ppm—20 percent by weight, preferably 0.1–10 percent by weight.

Formulations which are diluted before use comprise the active compound in concentrations of 0.5–90% by weight, preferably 5–50% by weight.

EXAMPLE A

In vivo nematode test

*Haemonchus contortus*/sheep

Sheep experimentally infected with *Haemonchus contortus* were treated after the end of the prepatency period of the parasites. The active compounds were administered orally and/or intravenously as pure active compound.

The degree of effectiveness is determined by quantitatively counting the worm eggs excreted with the faeces, before and after treatment.

Complete cessation of the excretion of eggs after treatment means that the worms have been expelled or are so severely damaged that they no longer produce any eggs (dosis effectiva).

The active compounds tested and effective dosages (dosis effectiva) can be seen from the following tables.

| Active compound Example No. | Dosis effectiva in [mg/kg] |
|---|---|
| 1 | 5 |
| 2 | 5 |
| 4 | 5 |
| 7 | 5 |
| 9 | 5 |
| 15 | 5 |
| 41 | 5 |
| 49 | 5 |
| 54 | 5 |
| 67 | 5 |
| 72 | 5 |
| 73 | 5 |
| 78 | 5 |
| 82 | 5 |

EXAMPLE B

In vivo nematode test

*Trichostrongylus colubriformis*/sheep

Sheep experimentally infected with *Trichostrongylus colubriformis* were treated after expiry of the prepatency time of the parasite. The active components were administered orally and/or intavenously as pure active compound.

The degree of effectiveness is determined by quantitatively counting the worm eggs excreted with the faeces before and after treatment.

Complete cessation of oviposition after treatment means the worms have been expelled or are so damaged that they no longer produce eggs (effective dose).

Active compound tested and effective doses can be seen from the following table.

| Active compound Example No. | Effective dose in [mg/kg] |
|---|---|
| 3 | 5 |
| 4 | 5 |
| 20 | 5 |
| 41 | 5 |
| 74 | 5 |
| 81 | 5 |

PREPARATION EXAMPLES

Example 1

7-Benzyl-4aα, 5aα, 8aα, 8bα-(±)-tetrahydro-3, 4a-dimethyl-6H-pyrrolo[3',4': 4,5]-furo[3,2-b]pyridine-6,8 (7H)-dione

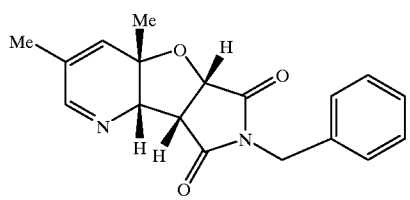

7.4 g (0.04 mol) of N-benzylmaleimide and 2.4 g (0.02 mol) of 3,5-dimethylpyridine N-oxide are stirred in 30 ml of toluene under the reflux temperature for 10 hours. The reaction mixture is then concentrated in vacuo and the crude product which remains is chromatographed over a silica gel column (silica gel 60-Merck, particle size: 0.04 to 0.063 mm) using the mobile phase cyclohexane ethyl acetate (1: 1). 3.6 g (58.0% of theory) of 7-benzyl-4aα, 5aα, 8aα, 8bα-(±)-tetrahydro-3, 4a-dimethyl-6H-pyrrolo[3',4': 4,5] furo[3,2-b] pyridine-6,8(7H)-dione are obtained.

Melting point: 123–124° C.

$^1$H-NMR (400 MHz, CDCl$_3$, δ): 1.27 (s, 3H, C—CH$_3$); 1.56 (d, 3H; =C—CH$_3$; J=1.6 Hz); 3.94 (dd, 1H, —CH—; J=9.6; 7.9); 4.24 (dd, 1H, J=9.6; 2.4 Hz); 4.57 (s, 2H, —CH$_2$-phenyl); 4.76 (d, 1H, —O—CH—; J=7.9 Hz); 5.74 (dd, 1H, =CH—, J=2.4; 1.2 Hz) 7.26–7.41 (2m, 5H, phenyl); 7.53 (t, 1H=CH—, J=2.4 Hz) ppm.

$^{13}$C-NM (100 MHz, CDCl$_3$, δ): 17.8; 24.8 (—CH$_3$); 42.0 (—CH$_2$); 50.1; 65.7 (—CH—) 74.4 (—O—CH—); 79.2 (—C—Me); 128.4 (=C—Me); 131.1; 159.1 (=CH—; hetaryl); 127.5; 128.1; 128.7; 135.0 (=CH—; phenyl); 172.7; 173.7 (—C=O) ppm.

EI-MS m/z (%): 310 (M$^+$, 100); 271 (38); 214 (62).

The compounds of the general formula (Ia) listed in the following Table 53 can be prepared analogously.

TABLE 53

Examples of compounds of the formula (I)

(I)

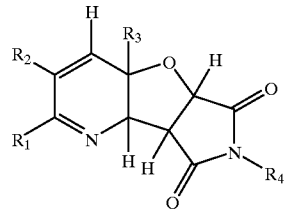

| Ex. No. | R$^1$ | R$^2$ | R$^3$ | R$^4$ | Physical data |
|---|---|---|---|---|---|
| 2 | —H | -methyl | -methyl | -methyl | mp: 177–180° C. |
| 3 | —H | -ethyl | -ethyl | -methyl | mp: 80° C. |
| 4 | —H | -methyl | -methyl | -ethyl | mp: 103–104° C. |
| 5 | —H | -ethyl | -ethyl | -ethyl | mp: 94° C. |
| 6 | —H | -methyl | -methyl | -n-propyl | mp: 76–78° C. |
| 7 | —H | -methyl | -methyl | -cyclopropyl | mp: 103° C. |
| 8 | —H | -methyl | -methyl | -allyl | mp: 115–118° C. |
| 9 | —H | -methyl | -methyl | -n-butyl | mp: 80–81° C. |
| 10 | —H | -methyl | -methyl | -isobutyl | mp: oil |
| 11 | —H | -methyl | -methyl | -cyclobutyl | mp: 82° C. |
| 12 | —H | -methyl | -methyl | -cyclopropylmethyl | mp: 89° C. |
| 13 | —H | -methyl | -methyl | -cyclopentyl | mp: oil |
| 14 | —H | -methyl | -methyl | -cyclohexyl | mp: 133–135° C. |
| 15 | —H | -methyl | -methyl | CH(CH$_3$)-phenyl* | mp: 117–118° C. |
| 16 | —H | -methyl | -methyl | 2,6-difluoro-phenyl | mp: 194° C. |
| 17 | —H | -methyl | -methyl | 4-bromo-phenyl | mp: 218° C. |
| 18 | —H | -ethyl | -ethyl | 4-bromo-phenyl | mp: 174–176° C. |
| 19 | —H | -methyl | -methyl | 2,4,6-trimethyl-phenyl | mp: 61–62° C. |
| 20 | —H | -methyl | -methyl | N-morpholinyl | mp: 153° C. |
| 21 | —H | -methyl | -methyl | 4-t-butyl-benzyl | mp: 117° C. |
| 22 | —H | -methyl | -methyl | 2,6-dichloro-benzyl | mp: 180° C. |

TABLE 53-continued

Examples of compounds of the formula (I)

(I)

| Ex. No. | R¹ | R² | R³ | R⁴ | Physical data |
|---|---|---|---|---|---|
| 23 | —H | -methyl | -methyl | 4-Cl, 3-CF₃-benzyl | mp: 128–129° C. |
| 24 | —H | -methyl | -methyl | 5-ethyl-2-chloropyridyl | mp: 144–145° C. |
| 25 | —H | -methyl | -methyl | 4-(4-CF₃-phenoxy)-methylphenyl | m.: 144–145° C. |
| 26 | —H | -methyl | -methyl | 4-CF₃S-phenyl | mp: 137° C. |
| 27 | —H | -methyl | -methyl | 4'-tBu-4-methylbiphenyl | mp: 236–237° C. |
| 28 | —H | -methyl | -methyl | 4-(4-iPr-phenoxy)-methylphenyl | mp: 140° C. |
| 29 | —H | -methyl | -methyl | 2-morpholinoethyl | 334(MH⁺, 80)ᵃ⁾ |
| 30 | —Ph | -methyl | -methyl | -ethyl | 311(MH⁺, 82); 186(100)ᵃ⁾ |
| 31 | —H | -methyl | -methyl | 2,4,5-trimethylphenyl | mp: 151° C. |
| 32 | —H | -methyl | -methyl | 2,6-dimethyl-4-bromophenyl | mp: 227–229° C. |
| 33 | —H | -methyl | -methyl | -t-butyl | mp: 96–97° C. |
| 34 | —H | -methyl | -methyl | 4-allyl-7-fluoro-6-methyl-2H-benzo[b][1,4]oxazin-3(4H)-one | mp: 159–162° C. |
| 35 | —H | -methyl | -methyl | 4-methylbenzyl | mp: 134–135° C. |
| 36 | —H | -methyl | -methyl | 4-methoxybenzyl | mp: 140–141° C. |
| 37 | —H | -methyl | -methyl | 4-chlorobenzyl | mp: 156–157° C. |
| 38 | —H | -methyl | -methyl | 3-chlorobenzyl | mp: 117–120° C. |
| 39 | —H | -methyl | -methyl | 2-chlorobenzyl | mp: 157–158° C. |

ᵃ⁾EI-MS or LC-MS(acid) m/z (%); Ph: phenyl; tBu: tert-butyl; iPr: isopropyl

Example 40

Hydrochloride of 7-ethyl-4aα, 5aα, 8aα, 8bα-(±)-tetrahydro-3, 4a-dimethyl-6H-pyrrolo[3',4': 4,5]furo[3,2-b]pyridine-6,8(7H)-dione (4)

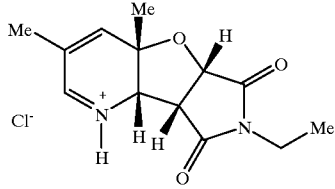

Dry hydrogen chloride gas is passed into a solution of 1.5 g (6.0 mmol) of 7-ethyl-4aα, 5aα, 8aα, 8bα-tetrahydro-3, 4a-dimethyl-6H-pyrrolo[3',4': 4,5]furo[3,2-b]pyridine-6,8 (7H)-dione (4) and 10 ml of acetone, while stirring. After a reaction time of about 20 minutes, the colorless hydrochloride which has precipitated out is separated off and washed with a large quantity of acetone.

1.6 g (93.6% of theory) of the hydrochloride of 7-ethyl-4aα, 5aα, 8aα, 8bα-(±)-tetrahydro-3, 4a-dimethyl-6H-pyrrolo[3',4': 4,5]furo[3,2-b]pyridine-6,8(7H)-dione are obtained.

Melting point: 134–135° C.

$^1$H-NMR (300 MHz, CDCl$_3$, 100 \f "symbol"): 0.94 (t, 3H, —CH$_3$; J=7.2 Hz); 1.34 (s, 3H, C—CH$_3$); 1.84 (d, 3H; =C—CH$_3$; J=1.6 Hz); 3.25–3.32 (q, 2H, —CH$_2$; 7.2 Hz); 3.98 (dd, 1H, —CH—; J=9.6; 7.9); 4.64 (dd, 1H, —CH—; J=9.6; 2.4 Hz); 4.84 (d, 1H, —O—CH—; J=7.9 Hz); 6.46 (dd, 1H, =CH—; J=2.4; 1.2 Hz); 8.55 (t, 1H, =CH—; J=2.4 Hz) ppm.

EXAMPLE 41

N$^1$-Methylammonium iodide of 7-ethyl-4aα, 5aα, 8aα, 8bα-(±)-tetrahydro-3, 4a-dimethyl-6H-pyrrolo[3',4': 4,5]furo[3,2-b]pyridine-6,8(7H)-dione (4)

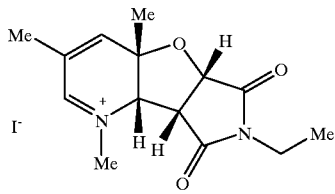

1.0 g (4.0 mmol) of 7-ethyl-4aα, 5aα, 8aα, 8bα-tetrahydro-3, 4a-dimethyl-6H-pyrrolo [3',4': 4,5]furo[3,2-b]pyridine-6,8(7H)-dione (4) is dissolved in 5 ml of acetone, and 1.4 g (9.8 mmol) of methyl iodide are added at room temperature. After 20 minutes, the solid which has precipitated out is separated off, washed with a large quantity of acetone and dried.

0.81 g (51.9% of theory) of N$^1$-methylammonium iodide is obtained.

$^1$H-NMR (300 MHz, CDCl$_3$, δ): 0.94 (t, 3H, —CH$_3$; J=7.2 Hz); 1.39 (s, 3H, C—CH$_3$); 1.84 (d, 3H; =C—CH$_3$; J=1.6 Hz); 3.28–3.31 (q, 2H, —CH$_2$; 7.2 Hz); 3.88 (s, 3H, =N$^+$—CH$_3$); 4.21 (dd, 1H, —CH—; J=9.6; 7.9 Hz); 4.68 (dd, 1H, —CH—; J=9.6; 2.4 Hz); 4.91 (d, 1H, —O—CH—; J=7.9 Hz); 6.58 (dd, 1H=CH—; J=2.4; 1.2 Hz); 8.86 (t, 1H, =CH—; J=2.4 Hz) ppm.

EI-MS m/z (%): 263 (M$^+$—I$^-$, 100); 271 (38); 122 (75).

Example 42

The N$^1$-methylammonium iodide of 7-methyl-4aα, 5aα, 8aα, 8bα-(+/−)-tetrahydro-3,4a-dimethyl-6H-pyrrolo[3',4', 5]furo[3,2-b]pyridine-6,8(7H)-dione (2) is prepared analogously from:

5,0 g (0,021 mol) 7-methyl-4aα, 5aα, 8aα, 8bα-(+/−)-tetrahydro-3,4a-dimethyl-6H-pyrrolo[3',4': 4,5]furo[3,2-b]pyridin-6,8(7H)-dione (2)

4,2 g (0,030mol) methyl iodide 125 ml acetone 5,6 g (70,4% of theory) of N$^1$-methylammonium iodide is obtained.

Melting point: 234° C.

Example 43

2.0 g (6.4 mmol) of 7-benzyl-4aα, 5aα, 8aα, 8bα-(±)-tetrahydro-3, 4a-dimethyl-6H-pyrrolo[3',4';4,5]furo[3,2-b]pyridine-6,8(7H)-dione are hydrogenated in 70 ml of ethanol in the presence of 0.3 g of Pd(OH)$_2$-charcoal [Pd content 20%] until the up-take of hydrogen has ended (about 4 hours). After the catalyst has been filtered off, the entire reaction solution is concentrated in vacuo. 1.8 g (99.1% of theory) of a (3:1) isomer mixture, which can be separated chroma-tographically over a silica gel column (silica gel 60—Merck, particle size: 0.04 to 0.063 mm) using the mobile phase ethyl acetate, are obtained.

7-Benzyl-l, 2, 3, 4, 4aα, 5aα, 8aα, 8bα-(±)-octahydro-3ct, 4a-dimethyl-6H-pyrrolo[3',4': 4,5]furo[3,2-b]pyridine-6,8 (7H)-dione

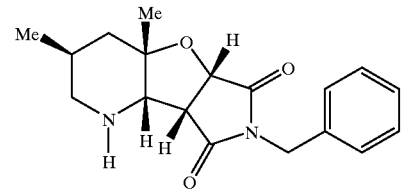

Melting point: 129–130° C.

$^{13}$C-NMR (100 MHz, CDCl$_3$, δ): 18.1; 25.3 (—CH$_3$); 39.2; 48.9; 42.0 (—CH$_2$); 26.8; 61.5; 50.3 (—CH—); 75.7 (—O—CH—); 84.8 (—C—Me); 127.5; 128.1; 128.5; 134.8 [=CH—; phenyl]; 174.5; 175.0 (—C=O) ppm.

Example 44

7-Benzyl-1, 2, 3, 4, 4aα, 5aα, 8aα, 8bα-(±)-octahydro-3cc, 4a-dimethyl-6H-pyrrolo[3',4': 4,5]furo[3,2-b] pyridine-6,8(7H)-dione

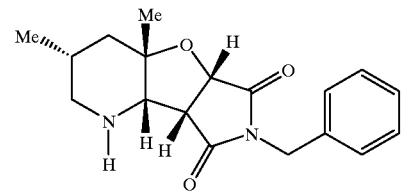

Melting point: 115–117° C.

$^{13}$C-NMR (100 MHz, CDCl$_3$, δ): 18.4; 25.0 (—CH$_3$); 41.7; 41.8; 51.2 (—CH$_2$); 26.1; 52.0; 59.7 (—CH—); 76.2 (—O—CH—); 86.6 (—C—Me); 127.3; 128.1; 135.2 (=CH—, phenyl); 174.2; 174.6 (—C=O) ppm.

The following was isolated in the hydrogenation of Example (2):

Example 45

7-Methyl-1,2, 4aα, 5aα, 8aα, 8bα-(±)-hexahydro-3,4a-dimethyl-6H-pyrrolo[3',4': 4,5]furo[3,2-b] pyridine-6,8(7H)-dione

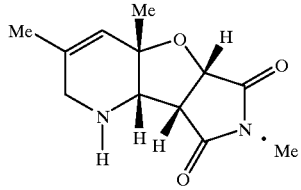

EI-MS m/z (%): 236 (M+, 61).

Example 46

7-methyl-1,2,4aα, 5aα, 8aα, 8bα-(+/−)-hexahydro-1,3,4a-trimethyl-6H-pyrrolo[3',4 :4,5]furo[3,2-b]pyridine-6,8(7H)dione

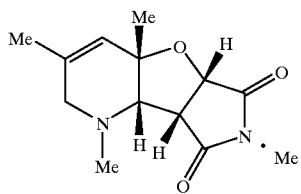

5.0 g (13.3 mmol) of the $N^1$-methylammonium iodide of 7-methyl-4aα, 5aα, 8aα, 8bα, 8bα (+/−)-tetrahydro-3,4a-dimethyl-6H-pyrrolo[3',4': 4,5]furo[3,2-pyridine-6,8(7H)-dione, are suspended in 100 ml of methanol and 0.64 g (16.9 mmol) of $NaBH_4$ are added in portions at −5° C. After stirring the mixture for two hours at 0° C. it is stirred at room temperature for about 18 hours. Then the entire reaction solution is concentrated in vacuo and the remaining residue is taken up in chloroform and shaken several times with water. The organic phase is separated off, dried over magnesium sulphate and concentrated in vacuo. 2.8 g (87.3% of theory) of 7-methyl-1,2,4aα,5aα,8aα,8b-(+/−)-hexahydro-1,3,4a-trimethyl-6H-pyrrolo[3',4': 4,5 ]furo[3,2-b]pyridine-6,8(7H)-dione are obtained.

M.p.: 124–125° C.

$^1$N-NMR (400 MHz, CDCl$_3$, δ): 1,37 (s,3H, —C—CH$_3$); 1.57 (s, 3H; =C—CH$_3$); 2.85; 2.91 (2s, 6H, 2×—N—CH$_3$); 2.97; 3.15 (2d, 2H, —C—CH$^a$H$^b$—; J=9.8HZ); 3.45 (dd, 1H, —CH—; J=9.9; 7.7 Hz); 3.55 (d, 1H, —CH-. J=9.9 Hz); 4.70 (d, 1H, —O—CH—; J=7.7 Hz); 5.29 (m, 1H, =CH—) ppm.

Example 47

1-(2-Chloroethoxycarbonyl)-1,2,4aα,5aα, 8aα, 8bα-(+/−)-hexahydro-3,4a, 7-trimethyl-6H-pyrrolo[3',4': 4,5]furo[3,2-b]pyridine-6,8(7H)dione,

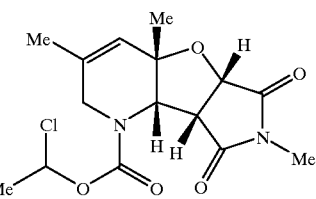

2.4 g (9.6 mmol) of 7-methyl-1,2,4aα,5aα8aα,8bα-(+/−)-hexahydro-1,3,4a-trimethyl-6H-pyrrolo[3',4': 4,5]furo[3,2-b]pyridine-6,8(7H)dione are stirred in 15 ml of 1,2-dichloroethane, 2.7 g (19.2 mmol) of 1-chloroethoxycarbonyl chloride are added and the mixture is heated for 20 minutes at the reflux temperature. Two portions of in each case of 1.3 g (9.6 mmol) of 1-chloroethoxycarbonyl chloride are then added at 20 minutes interval, and the mixture is then stirred for 5 hours at the reflux temperature. The entire reaction mixture is concentrated in vacuo and purified in a silica gel column (silica gel 60, from Merck; particle size: 0.04 to 0.063 mm) using ethyl acetate as the mobile solvent. 1.7 g (53.9% of theory) of 1-(1-chloroethoxycarbonyl)-1,2,4aα,5aα,8aα,8bα-(+/−)-hexahydro-3,4a,7-trimethyl-6H-pyrrolo[3',4': 4,5]furo[3,2-b]pyridine-6,8(7H)dione is obtained, which can be immediately reacted further.

Example 48

The hydrochloride of 1,2,4aα,5aα,8aα,8bα-(+/−)-hexahydro-3,4a, 7-trimethyl-6H-pyrrolo[3',4': 4,5]furo[3,2-b]pyridine-6,8(7H)dione (45)

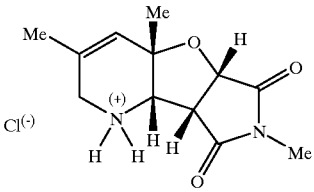

1.7 g (5.2 mmol) of 1-(1-chloroethoxycarbonyl)-1,2,4aα, 5aα, 8aα, 8bα-(+/−)-hexahydro-3,4a,7-trimethyl-6H-pyrrolo[3',4': 4,5]furo[3,2-b]pyridine-6,8(7H)-dione are stirred in 4 ml of methanol and the mixture is initially heated to 50–60° C.; then it is subsequently stirred for about 30 minutes at the reflux temperature. The hydrochloride precipitated is washed with a small amount of ether. 1.1 g (77.6% of theory) of the hydrochloride of 1,2,4aα, 5aα, 8aα, 8bα-(+/−)-hexahydro-3,4a,7-trimethyl-6H-pyrrolo[3',4': 4,5]furo[3,2-b]pyridine-6,8(7H)-dione is obtained.

$^1$H-NMR (400 MHz, D$_2$O, δ): 1.42 (s, 3H, —C—CH$_3$); 1,78 (s, 3H; =C—CH$_3$); 2.98 (2s, 6H, 2×—N—CH$_3$); 3.58; 3.67 (2d, 2H, —C—CH$^a$H$^b$; J=9.8 Hz); 4.11 (d, 1H, —CH—; J=9.9 Hz); 4.35 (dd; 1H, —CH—; J=9.9; 7.7 Hz); 5.03 (d, 1H, —O—CH—; J=7.7 Hz); 5.73 (m, 1H, =CH—) ppm.

Example 49

1-Allyloxycarbonyl-7-ethyl-1,2,4aα,5aα,8aα,8bα-(+/−)-hexahydro-3,4a-dimethyl-6H-pyrrolo[3',4': 4,5]furo[3,2-b]pyridine-6,8(7H)-dione

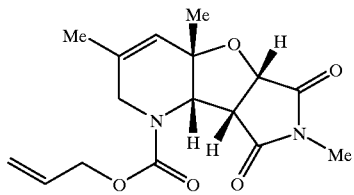

In order to obtain the free base 2.6 g (9.1 mmol) of the hydrochloride of 7-ethyl-1,2,4aα,5aα,8aα,8bα-(+/−)-hexahydro-3,4a,7-trimethyl-6H-pyrrolo[3',4': 4,5]furo[3,2-b]pyridine-6,8(7H)-dione are stirred with 1.4 g (10.9 mmol) of N,N-diisopropylethylamine ("Hünig's base") in a mixture of 50 ml of wataer and 150 ml of methylene chloride. After 10 minutes the organic phase is separated off and dried over magnesium sulphate. Then 1.8 g (13.6 mmol) of N,N-diisopropylethylamine ("Hünig's base") and 1.3 g (10.9 mmol) of allylchloroformate are added to the methylene chloride phase at 0° C. and the mixture is stirred for about 10 minutes at 0° C. and for 2 hours at room temperature. Then the organic phase is extracted twice with water, dried over magnesium sulphate and concentrated in vacuo. The remaining crude product is chromatographed in a silica gel column (silica gel 60 from Merck; particle size: 0.04 toi 0.063 mm) using cyclohexane:ethyl acetate (1:1) as the mobile phase. 1.0 g (32.9% of theory) of 1-allyloxycarbonyl-7-ethyl-1,2,4aα,5aα,8aα8bα-(+/−)-hexahydro-3,4a-dimethyl-6H-pyrrolo[3',4': 4,5]furo[3,2-b]pyridine-6,8(7H)-dione is obtained.

M.p. 87–90° C.

EI-MS m/z (%): 334 (M+; 2); 249 (M+—[H₂C=CH—H₂C—O—CO], 100].

Preparation According to Process 5a

Example 50

1-Methyl-7-ethyl-1, 2, 3, 4, 4aα, 5aα, 8aα, 8bα-(±)-octahydro-3α, 4a-dimethyl-6H-pyrrolo[3',4': 4,5]furo[3,2-b]pyridine-6,8(7H)-dione

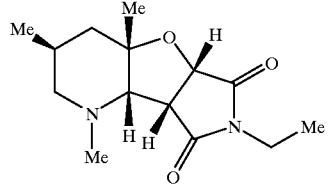

1.1 g (9.6 mmol) of methyl iodide are added to a solution of 2.0 g (8.4 mmol) of 7-ethyl-1, 2, 3, 4, 4aα, 5aα, 8aα, 8bα-(±)-octahydro-3α,4a-dimethyl-6H-pyrrolo[3',4': 4,5]furo[3,2-b]pyridine-6,8(7H)-dione and sodium bicarbonate in 100 ml of dimethylformamide under a nitrogen atmosphere and the mixture is stirred at 80° C. for about 5 hours hours. The reaction solution poured onto water and extracted several times with ethyl acetate and the organic phase separated off and, after drying over sodium sulfate, concentrated in vacuo. The crude product which remains is chromatographed over a silica gel column.

LC-MS (acid) m/z (%): 283 (MH+, 100); 265 (12); 141 (37); 101 (66)

Preparation According to Process 5b

Example 51

1-(2-Cyanoethyl)-7-ethyl-1, 2, 3, 4, 4aα, 5aα, 8aα, 8bα-(±)-octahydro-3α, 4a-dimethyl-6H-pyrrolo[3',4': 4, 5]furo[3,2-b]pyridine-6,8(7H)-dione

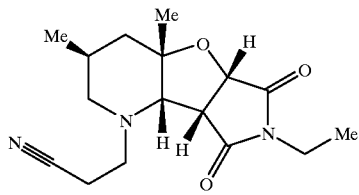

2.0 g (87.9 mmol) of 7-ethyl-1, 2, 3, 4, 4aα, 5aα, 8aα, 8bα-(±)-octahydro-3α,4a-dime-thyl-6H-pyrrolo[3',4': 4,5]furo[3,2-b]pyridine-6,8(7H)-dione and 0.5 g (10.0 mmol) acrylonitrile are stirred at the reflux temperature in 10 ml of ethanol for 28 hours. The reaction solution is shaken twice with water and the organic phase is separated off and, after drying over sodium sulfate, concentrated in vacuo. The crude product which remains chromatographed over a silica gel column (silica gel 60—Merck, particle size : 0.04 to 0.063 mm).

LC-MS (acid) m/z (%): 306 (MH+, 100); 253 (M+—[NC—CH₂—CH₂—], 29).

Preparation According to Process 5c

Example 52

1-((±)-2-Hydroxy-3-isopropoxyprop-1-yl)-7-ethyl-1, 2, 3, 4, 4aα, 5aα, 8aα, 8bα-(±)-octahydro-3α, 4a-dimethyl-6H-pyrrolo[3',4': 4,5]furo[3,2-b]pyridine-6, 8(7H)-dione

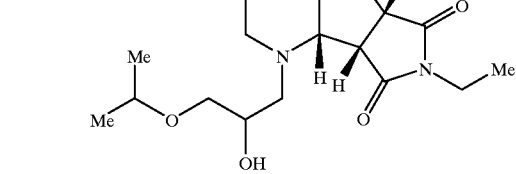

To a solution of 5.0 g (19.2 mmol) of 7-ethyl-1, 2, 3, 4, 4aα, 5aα, 8aα, 8bα-(±)-octahydro-3α,4a-dimethyl-6H-pyrrolo[3',4': 4,5]furo[3,2-b]pyridine-6,8(7H)-dione and 0.9 g (8.0 mmol) of (±)-2,3-epoxypropyl isopropyl ether in 40 ml of tetrahydrofuran are heated under the reflux temperature for 24 hours. The entire reaction solution is then concentrated in vacuo and the crude product which remains is chromatographed.

LC-MS (acid) m/z (%): 369 (MH+, 100); 253 (16)

Preparation According to Process 5d

Example 53

1-Allyloxycarbonyl-7-methyl-1, 2, 3, 4, 4aα, 5aα, 8aα, 8bα-(±)-octahydro-3α, 4a-dimethyl-6H-pyrrolo[3',4': 4,5]furo[3,2-b]pyridine-6,8(7H)-dione

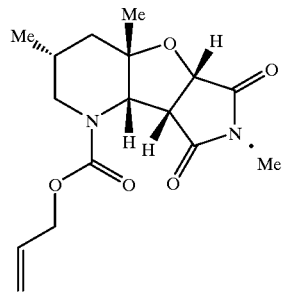

2.8 g (21.6 mmol) of N,N-diisopropylethylamine ("Hünig's base") are added to a solution of 2.0 g (8.4 mmol) of 7-methyl-1, 2, 3, 4, 4aα, 5aα, 8aα, 8bα-(±)-octahydro-3β, 4a-dimethyl-6H-pyrrolo[3',4': 4,5]furo[3,2-b]pyridine-6,8 (7H)-dione and 1.1 g (9.6 mmol) of allylchloroformate in 100 ml of methylene chloride at 0° C. and the mixture is stirred at 0° C. for 2 hours and then at room temperature for 2 hours. The reaction solution is shaken twice with water and the organic phase is separated off and, after drying over sodium sulfate, concentrated in vacuo. The crude product which remains is chroma-tographed over a silica gel column (silica gel 60—Merck, particle size : 0.04 to 0.063 mm) using the mobile phase of ethyl acetate. 1.9 g (73.9% of theory) of 1-allyloxycarbonyl-7-methyl-1, 2, 3, 4, 4aα, 5aα, 8aα, 8bα-(±)-octahydro-3β,4a-dimethyl-6H-pyrrolo[3',4': 4,5]furo[3,2-b] pyridine-6,8(7H)-dione are obtained as an oily product.

EI-MS m/z (%): 322 (M$^+$, 5); 237 (100); 108 (72).

Example 54

1-Allyloxycarbonyl-7-methyl-1, 2, 3, 4, 4aα, 5aα, 8aα, 8bα-(±)-octahydro-3α, 4a-dimethyl-6H-pyrrolo[3',4'4,5]furo[3,2-b]pyridine-6,8(7H)-dione

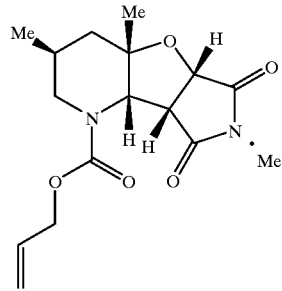

The N-acylation is carried out analogously to the reaction instructions of Example (53) in the course of 4 hours, using:
2.0 g (8.4 mmol) of 7-methyl-1, 2, 3, 4, 4aα, 5aα, 8aα, 8bα-(±)-octahydro-3α,4a-dimethyl-6H-pyrrolo[3',4': 4,5]furo[3,2-b]pyridine-6,8(7H)-dione
1.1 g (9.6 mmol) of allylchloroformate
2.8 g (21.6 mmol) of N,N-diiso-propylethylamine ("Hünig's base")
100 ml of methylene chloride
1.6 g (64.6% of theory) of 1-allyloxycarbonyl-7-methyl-1, 2, 3, 4, 4aα, 5aα, 8aα, 8bα-(±)-octahydro-3α, 4a-dimethyl-6H-pyrrolo[3',4': 4,5]furo[3,2-b]pyridine-6,8 are obtained (7H)-dione.

Melting point: 94–96° C.
EI-MS m/z (%): 322 (M$^+$, 6); 237 (100); 108 (50).

Example 55

1-Chloromethylcarbonyl-7-ethyl-1, 2, 3, 4, 4aα, 5aα, 8aα, 8bα-(±)-octahydro-3α,4a-dimethyl-6H-pyrrolo[3',4'4, 5]furo[3,2-b]pyridine-6,8(7H)-dione :

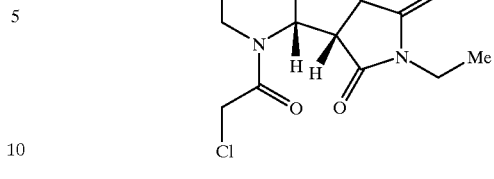

The N-acylation is carried out analogously to the reaction instructions of Example (53) in the course of 1 hour using:
6.0 g (23.7 mmol) of 7-ethyl-1, 2, 3, 4, 4aα, 5aα, 8aα, 8bα-(±)-octahydro-3a, 4a-dimethyl-6H-pyrrolo[3',4': 4,5] furo[3,2-b]pyridine-6,8(7H)-dione
3.3 g (28.5 mmol) of chloroacetyl chloride
6.6 g (65.1 mmol) of triethylamine
60 ml of methylene chloride
EI-MS m/z (%): 328 (M$^+$, 8); 251 (M$^+$—[C$_1$–CH$_2$—CO], 100); 108 (44).

Example 56

1-(N-Morpholino-methylcarbonyl)-7-ethyl-1, 2, 3, 4, 4aα, 5aα, 8aα, 8bα-(±)-octahydro-3α, 4a-dimethyl-6H-pyrrolo[3',4': 4,5]furo[3,2-b]pyridine-6,8(7H)-dione

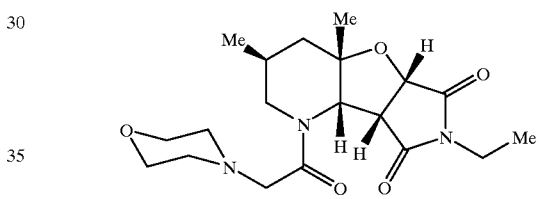

0.2 g (1.8 mmol) of triethylamine is added to a solution of 0.5 g (1.5 mmol) of 1-chloromethylcarbonyl-7-ethyl-1, 2, 3, 4, 4aα, 5aα, 8aα, 8bα-(±)-octahydro-3α, 4a-dimethyl-6H-pyrrolo[3',4': 4,5]furo[3,2-b]pyridine-6,8(7H)-dione (55) and 0.15 g (1.8 mmol) of morpholine in 5 ml of acetonitrile and the mixture is heated at the reflux temperature for 1 hour.

The reaction solution is concentrated in vacuo, the residue is taken up in chloroform and the mixture is shaken several times with water. The organic phase is then separated off and, after drying over magnesium sulfate, concentrated in vacuo. The crude product which remains chromatographed over a silica gel column (silica gel 60—Merck, particle size : 0.04 to 0.063 mm) using the mobile phase of ethyl acetate. 0.25 g (43.3% of theory) of 1-(N-morpholinomethylcarbonyl)-7-ethyl-1, 2, 3, 4, 4aα, 5aα, 8aα, 8bα-(±)-octahydro-3α, 4a-dimethyl-6H-pyrrolo-6H[3', 4': 4,5]furo[3,2-b]pyridine-6,8(7H)-dione is obtained.

$^1$H-NMR (300 MHz, CDCl$_3$, δ): 2.60 (m, br., 4H, —(CH$_2$)$_2$—N—); 3.77 (m, br., 4H, —(CH$_2$)$_2$—O) ppm.

EI-MS m/z (%): 379 (M$^+$, 1); 251 (M$^+$—[—CO—CH$_2$—Nmorpholine], 1); 100([—CH$_2$—Nmorpholine], 100).

Preparation According to Process 5e

Example 57

1-(Carboxylmethyloxymethylcarbonyl)-7-methyl-1, 2, 3, 4, 4aα, 5aα, 8aα, 8bα-(±)-octahydro-3α, 4a-dimethyl-6H-pyrrolo[3',4': 4,5]furo[3,2-b]pyridine-6,8(7H)-dione

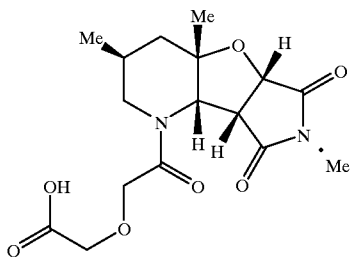

2.0 g (8.4 mmol) of 7-methyl-1, 2, 3, 4, 4aα, 5aα, 8aα, 8bα-(±)-octahydro-3α,4a-dimethyl-6H-pyrrolo-[3',4': 4,5]furo[3,2-b]pyri-dine-6,8(7H)-dione, dissolved in 10 ml of tetrahydofuran, are dropwise added dropwise to a solution of 1.4 g (12.0 mmol) of diglycolic anhydride in 20 ml of dry tetrahydrofuran at 50° C. and stirring 20 is then continued at this temperature for 12 hours. The entire reac-tion solution is then concentrated in vacuo and the substance which remains is separated off and washed several times with ether.

LC-MS (acid) m/z (%): 355 (MH+, 100), 309 (12).

Example 58

1-(Carboxylmethyloxymethylcarbonyl)-7-methyl-1, 2, 4aα, 5aα, 8aα, 8bα-(±)-hexahydro-3, 4a-dimethyl-6H-pyrrolo[3',4': 4,5]furo[3,2-b]pyridine-6,8(7H)-dione

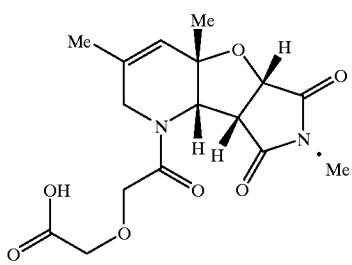

The N-acylation is carried out analogously to the reaction instructions of Example (57) in the course of 12 hours, using:

2.0 g (8.4 mmol) of 7-methyl-1, 2, 4aα, 5aα, 8aα, 8bα-(±)-hexahydro-3, 4a-dimethyl-6H-pyrrolo[3',4': 4,5]furo[3,2-b]pyridine-6,8(7H)-dione
1.4 g (12.0 mmol) of diglycolic anhydride
30 ml of tetrahydrofuran
LC-MS (acid) m/z (%): 353 (M–H+, 100); 237 (18)

Preparation According to Process 5f

Example 59

1-(N-Benzyloxycarbonyl-N-methyl-glycyl)-7-methyl-1, 2, 3, 4, 4aα, 5aα, 8aα, 8bα-(±)-octahydro-3α, 4a-dimethyl-6H-pyrrolo[3',4': 4,5]furo[3,2-b]pyridine-6,8(7H)-dione

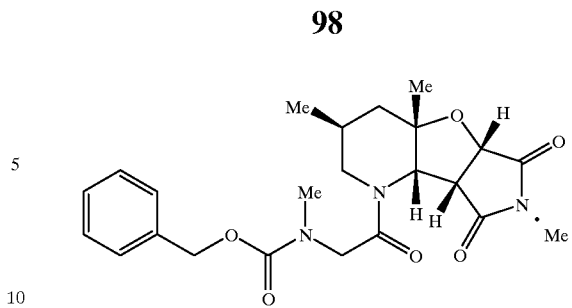

3.2 g (25.2 mmol) of N,N-diisopropylethylamine ("Hünig's base") and 2.1 g (8.4 mmol) of bis(2-oxo-3-oxazolidinyl)-phosphonium acid chloride (BOP-CI) are added to a solution of 2.0 g (8.4 mmol) of 7-methyl-1, 2, 3, 4, 4aα, 5aα, 8aα, 8bα-(±)-octahydro-3α,4a-dimethyl-6H-pyrrolo[3',4': 4,5]furo[3,2-b]pyridine-6,8(7H)dione and 1.7 g (7.6 mmol) of N-benzyloxycarbonyl-sarcosine (Z-Sar-OH) in 100 ml of methylene chloride at 0° C. and the mixture is stirred at 0° C. for 30 minutes and then at room temperature for 18 hours. The reaction solution is shaken twice with water and the organic phase is separated off and, after drying over sodium sulfate, concentrated in vacuo. The crude product which remains is chromatographed over a LiChroprep RP-18 column (LiChroprep RP-18—Merck, particle size : 0.4 to 0.063 mm) using the mobile phase of acetonitrile/water (4:6).

$^1$H-NMR (300 MHz, CDCl$_3$, δ): 2.98; 3.08 (2s, 6H, 2×N—CH$_3$) ppm.
EI-MS m/z (%): 444 (MH+; 4); 443 (M+, 15); 237 (M+—[—CO—CH$_2$—NMe—CO—O-ben-yl]; 38); 209 (20); 91(benzyl; 100).

Preparation According to Process 5g

Example 60

1-Trichloroacetylaminocarbonyl-7-methyl-1, 2, 3, 4, 4aα, 5aα, 8aα, 8bα-(±)-octahydro-3α, 4a-dimethyl-6H-pyrrolo[3',4': 4,5]furo[3,2-b]pyridine-6,8(7H)-dione

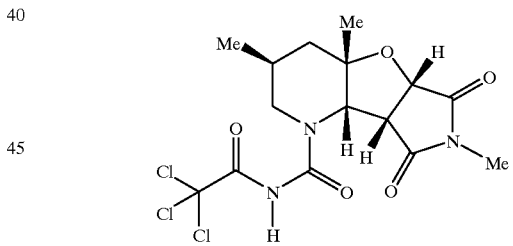

1.6 g (8.4 mmol) of trichloroacetyl isocyanate are added to a solution of 2.0 g (8.4 mmol) of 7-methyl-1, 2, 3, 4, 4aα, 5aα, 8aα, 8bα-(±)-octahydro-3α,4a-dimethyl-6H-pyrrolo[3',4': 4,5]furo[3,2-b]pyridine-6,8(7H)-dione in 30 ml of acetonitrile at 0° C. and the mixture is stirred at 0° C. for 30 minutes. The reaction solution is shaken twice with water and the organic phase is separated off and, after drying over sodium sulfate, concentrated in vacuo. The crude product which remains is chromatographed over a silica gel column (silica gel 60—Merck, particle size 0.04 to 0.063 mm) using the mobile phase of ethyl acetate. 1.2 g (34.6 g of theory) of 1-trichloroacetylaminocarbonyl-7-methyl-1, 2, 3, 4, 4aα, 5aα, 8aα, 8bα-(±)-octahydro-3ot, 4a-dimethyl-6H-pyrrolo[3',4': 4,5]furo[3,2-b]pyridine-6,8(7H)-dione are obtained.

EI-MS m/z (%): 391 (M+—Cl, 1); 355 (M+—2Cl, 8); 306 (M+—[Cl$_3$CH]; 19); 237 (100)

Preparation According to Process 5h

Example 61

1-Propargyloxycarbonyl-7-methyl-1, 2, 3, 4, 4aα, 5aα, 8aα, 8bα-(±)-octahydro-3a, 4a-dimethyl-6H-pyrrolo[3',4': 4,5]furo[3,2-b]pyridine-6,8(7H)-dione

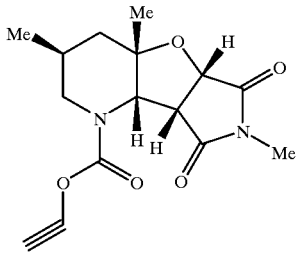

2.0 g (8.4 mmol) of 7-methyl-1, 2, 3, 4, 4aα, 5aα, 8aα, 8bα-(±)-octahydro-3α, 4a-dimethyl-6H-pyrrolo[3',4': 4,5] furo[3,2-b]pyridine-6,8(7H)-dione and 30 ml of dimethyl sulfoxide are gassed with carbon dioxide for one hour, and 1.1 g (8.4 mmol) of propargylbromide are then added. the reaction mixture was stirred at room temperature for 48 hours, the solid was then separated off, the volatile components were stripped off under reduced pressure, the residue was extracted with ethyl acetate and the organic phase was separated off. The organic phase is then dried over sodium sulfate and concentrated in vacuo and the crude product which remains is chromatographed over a LiChroprep RP-18 column (LiChroprep RP-18—Merck, particle size: 0.4 to 0.063 mm) using the mobile phase of acetonitrile/water (4:6).

EI-MS m/z (%): 320 (M$^+$, 0.5); 237 (M$^+$—[HC≡C—CH$_2$—O—CO-], 20).

The following was isolated as a by-product:

Example 62

1-Propargyl-7-methyl-1, 2, 3, 4, 4aα, 5aα, 8aα, 8bα-(±)-octahydro-3α, 4a-dimethyl-6H-pyrrolo[3',4': 4,5]furo[3,2-b] pyridine-6,8(7H)-dione

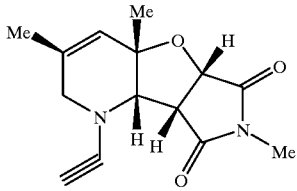

EI-MS m/z (%): 276 (M$^+$, 5); 237 (M$^+$—[HC≡C—CH$_2$—], 100), 39 ([HC≡C—CH$_2$—], 46).

Preparation According to Process 5i

Example 63

1-(4—Nitrophenoxycarbonyl)-7-ethyl-1, 2, 3, 4, 4aα, 5aα, 8aα, 8bα-(±)-octahydro-3 α, 4a-dimethyl-6H-pyrrolo[3',4': 4,5]furo[3,2-b] pyridine-6,8(7H)-dione

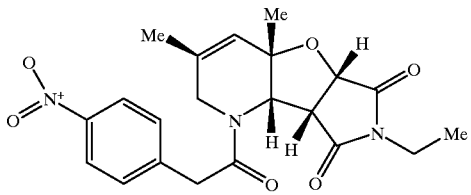

4.4 (J (34.8 mmol) of N,N-diisopropylethylamine ("Hünig's base") are added to a solution of 4.0 g (15.8 mmol) of 7-ethyl-1, 2, 3, 4, 4aα, 5aα, 8aα, 8bα-(±)-octahydro-3aα, 4a-dimethyl-6H-pyrrolo[3',4': 4,5]furo[3,2-b]pyridine-6,8 (7H)-dione and 3.2 g (15.8 mmol) of 4-nitrophenyl chloroformate in 100 ml of methylene chloride at 0° C. and the mixture is stirred at 0° C. for 2 hours and then at room temperature for 18 hours. The reaction solution is shaken twice with water and the organic phase is separated off and, after drying over magnesium sulfate, concentrated in vacuo. The crude product which remains chromatographed over a silica gel column (silica gel 60—Merck, particle size: 0.04 to 0.063 mm) using the mobile phase cyclohexane : ethyl acetate (1:1). 4.0 g (62.4% of theory) of 1-(4-nitrophenoxycarbonyl)-7-ethyl-1, 2, 3, 4, 4aα, 5aα, 8aα, 8bα-(±)-octahydro-3α, 4a-dimethyl-6H-pyrrolo[3',4': 4,5] furo[3,2-b]pyridine-6,8(7H)-dione are obtained.

Melting point: 160–167° C.

$^1$H-NMR (400 MHz, CDCl$_3$, δ): 7.42; 8.29 (2d, 4H, 4—NO$_2$-phenoxy; J$_{H,H}$=9.1 Hz) ppm.

EI-MS m/z (%): 417 (M$^+$, 0.29); 279 (33); 223 (100).

Example 64

1-(N-Morpholinocarbonyl)-7-ethyl-1, 2, 3, 4, 4aα, 5aα, 8aα, 8bα-(±)-octahydro-3a, 4a-dimethyl-6H-pyrrolo[3',4': 4,5]furo[3,2-b]pyridine-6,8(7H)-dione

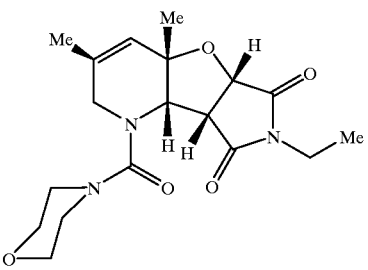

0.65 g (5.0 mmol) of N,N-diisopropylethylamine ("Hünig's base") and 0.45 g (5.2 mmol) of morpholine are added to a solution of 2.0 g (4.8 mmol) of 1-(4-nitrophenoxycarbonyl)-7-ethyl-1, 2, 3, 4, 4aα, 5aα, 8aα, 8bα-(±)-octahydro-3α, 4a-dimethyl-6H-pyrrolo[3',4': 4,5] furo[3,2-b]py-ridine-6,8(7H)-dione in 40 dioxane at room temperature and the mixture is stirred under the reflux temperature for about 48 hours. The reaction solution is shaken twice with water and the organic phase is separated off and, after drying over magnesium sulfate, concentrated in vacuo. The crude product which remains chromatographed over a silica gel column.

LC-MS (acid) m/z (%): 366 (MH$^+$, 100); 253 (3); 141 (20); 101 (33).

The compounds of the general formula (Ib), (Ic) and (Id; R$^5$: —H) listed in the following Table 54 and 55 can be prepared analogously to the processes.

TABLE 54

Examples of compounds of the formula (Ib) and (Id; $R^5$: —H)

(Ib)

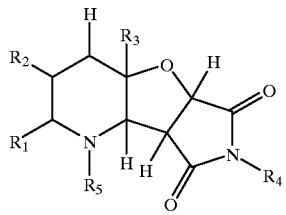

| Ex. No. | $R^1$ | $R^2$ | $R^3$ | $R^4$ | $R^5$ | Physical data |
|---|---|---|---|---|---|---|
| 65 | —H | 3β-Me | 4α-Me | -methyl | —H | mp: 147–149° C. |
| 66 | —H | 3α-Me | 4α-Me | -methyl | —H | mp: 134–135° C. |
| 67 | —H | 3β-Me | 4a-Me | -methyl | —CO—O-s-Bu | mp: 134–135° C. |
| 68 | —H | 3α-Me | 4α-Me | -methyl | —CO—O-s-Bu | mp: 84–85° C. |
| 69 | —H | 3β-Me | 4α-Me | -ethyl | —H | mp: 95–96° C. |
| 70 | —H | 3α-Me | 4α-Me | -ethyl | —H | mp: 90–93° C. |
| 71 | —H | 3α-Me | 4α-Me | -ethyl | —CO—O-allyl | mp: 96–98° C. |
| 72 | —H | 3β-Me | 4α-Me | -ethyl | —CO—O-allyl | mp: oil |
| 73 | —H | 3α-Me | 4α-Me | -ethyl | —SO$_2$—NMe$_2$ | mp: 88–89° C. |
| 74 | —H | 3α-Me | 4α-Me | -ethyl | —CO—O—Me | mp: 129–131° C. |
| 75 | —H | 3β-Me | 4α-Me | -ethyl | —CO—O—Me | mp: 87° C. |
| 76 | —H | 3α-Me | 4α-Me | -ethyl | —CO—NMe$_2$ | mp: 104–105° C. |
| [001b]77 | —H | 3α-Me | 4α-Me | -methyl | —CO—CH$_2$—Cl | 314(M$^+$, 8)$^{a)}$ |
| 78 | —H | 3α-Me | 4α-Me | -methyl | —CO—CH$_2$—Cl | 314(M$^+$, 8)$^{a)}$ |
| 79 | —H | 3α-Me | 4α-Me | -methyl | —CO—O—CH$_2$—PH | mp: 164–165° C. |
| 80 | —H | 3α-Me | 4α-Me | -butyl | —CO—O-allyl | mp: oil |
| 81 | —H | 3β-Me | 4α-Me | -methyl | —CO—O-allyl | mp: 88° C. |

$^{a)}$EI-MS/LC-MS (acid) m/z (%);
abbreviations:
Nph: 4-nitro-phenyl; Ph: phenyl; Bu: butyl; allyl: —CH$_2$—CH═CH$_2$ i-, s- and t: iso-, secondary and tertiary

TABLE 55

Examples of compounds of the formula (Ic) and (Ie; $R^5$: —H)

(Ic)

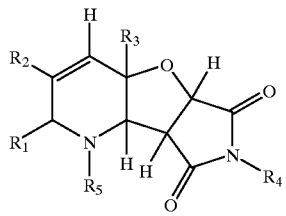

| Ex. No. | $R^1$ | $R^2$ | $R^3$ | $R^4$ | $R^5$ | Physical data |
|---|---|---|---|---|---|---|
| 82 | —H | —Me | 4α-Me | -methyl | —CO—NMe—CO—NMe$_2$ | mp: 134–135° C. |
| 83 | —H | —Me | 4α-Me | -methyl | —CO—NMe$_2$ | mp: 170–171° C. |
| 84 | —H | —Me | 4α-Me | -methyl | —CO—O-allyl | mp: 94–95° C. |
| 85 | —H | —Me | 4α-Me | -ethyl | -methyl | mp: 80–82° C. |
| 86 | —H | —Me | 4α-Me | -ethyl | —CO—O—CHCl—Me | mp: oil |
| 87 | —H | —Me | 4α-Me | -ethyl | —H.hydrochloride | mp: oil | abbreviations:
Me: -methyl; Ph: phenyl; Bu: butyl; allyl: —CH$_2$—CH═CH$_2$ i-, s- and t: iso-, secondary and tertiary Starting Substances of the Formula (II)

Example (II-1)

3,5-Dimethyl-pyridine N-oxide

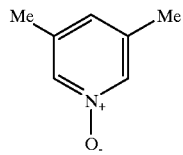

68.6 ml of hydrogen peroxide (30% strength) are added dropwise to a solution of vi 73.5 g (0.68 mol) of 3,5-dimethylpyridine in 410 ml of glacial acetic acid and the mixture is stirred at 70–80° C. for 3 hours. A further 48 ml of hydrogen peroxide (30% strength) are then added and the mixture is stirred at 70–80° C. for a further 9 hours. For working up, the entire reaction batch is rendered basic with concentrated sodium hydroxide solution and extracted by shaking with chloroform, and the organic phase which has been separated off is dried over sodium sulfate and concentrated in vacuo. The crude product which remains crystallizes on stirring with a chloroform/hexane mixture.

53.6 g (63.4% of theory) of 3,5-dimethyl-pyridine N-oxide are obtained.

$^1$H-NMR (400 MHz, CDCl$_3$, δ): 2.27 (s, 6H, C—CH$_3$); 6.94; 7.92 (2×t, 3H; hetaryl) ppm.

EI-MS m/z (%): 123 (M$^+$, 100); 107 (M$^+$–0.5).

Example (II-2)

3,5-Diethyl-pyridine N-oxide is prepared analogously from:

30.9 (0.22 mol) of 3,5-diethyl-pyridine
39 ml of hydrogen peroxide (30% strength)
137 ml of glacial acetic acid
33.8 g (97.8% of theory) of 3,5-diethyl-pyridine N-oxide are obtained.

$^1$H-NMR (400 MHz, CDCl$_3$, δ): 1.25 (t, 6H, 2×—CH$_3$; J=7.6 Hz); 2.60 (q, 4H, 2×—CH —; J=7.6 Hz); 6.98; 7.96 (2×t, 3H; hetaryl) ppm

Example (II-3)

2-Phenyl-3-methyl-pyridine N-oxide is prepared analogously from:

30.9 g (0.18 mol) of 2-phenyl-3-methyl-pyridine
32 ml of hydrogen peroxide (30% strength)
112 ml of glacial acetic acid
38.5 g (85.9% of theory) of 2-phenyl-3-methyl-pyridine N-oxide are obtained.

$^1$H-NMR (300 MHz, CDCl$_3$, δ): 2.11 (s, 3H, hetaryl-CH$_3$); 7.13–7.54 (3α, 7H, phenyl-H/hetaryl-H); 8.24 (m, 1H, hetaryl-H) ppm.

Starting Substances of the Formula (III)

Example (III-1)

N-Morpholinyl-maleimide

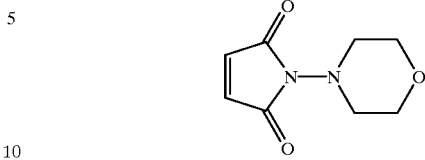

24.3 g (0.15 mol) of (E/Z)-N-morpholino-maleamic acid are stirred with 100 g of acetic anhydride and 1.0 g of anhydrous sodium acetate at 100° C. for 1 hour. The entire reaction mixture is then poured onto ice-water, stirred at room temperature for about 18 hours and extracted with methylene chloride. After the organic phase has been separated off and dried over sodium sulfate, it is concentrated in vacuo and the crude product which remains is chromatographed over a silica gel column (silica gel 60—Merck, particle size : 0.04 to 0.063 mm) using the mobile phase of cyclohexane : ethyl acetate (1:1). 7.7 g (35.2% of theory) of N-morpholinomaleimide are obtained.

Melting point: 104–105° C.

$^1$H-NMR (400 MHz, CDCl$_3$, δ): 3.30 (t, 4H, —CH$_2$—N—CH$_2$; J=4.4 Hz); 3.83 (t, 4H, —CH$_2$—O—CH$_2$—; J=4.4 Hz); 6.64 (s, 2H, 2×=CH—) ppm EI-MS m/z (%): 182 (M$^+$, 100).

Example (III-2)

N-Cyclopropyl-maleimide

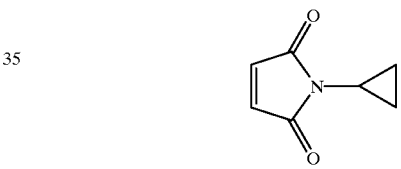

21.6 g (0.22 mol) of maleic anhydride are suspended in 300 ml of methylene chloride, and 16.0 g (0.22 mol) of cyclopropylamine are added dropwise at 0° C. in the course of 5 minutes. After the reaction mixture has been stirred at room temperature for 16 hours, it is cooled to 0° C. and a few drops of dimethylformamide are added. 20 ml (0.24 mol) of oxalyl chloride are then added in the course of 30 minutes.

The mixture is stirred at room temperature for a further 8 hours, the excess oxalyl chloride is stripped off in vacuo, the crude product which remains is dissolved again in 180 ml of methy-lene chloride, and 30.6 ml (0.22 mol) of triethylamine are added. The reaction mixture is stirred at room temperature for 1.5 hours and filtered and the fil-trate which remains is washed with 1 N HCl. After the organic phase has been separated off and dried over sodium sulfate, it is concentrated in vacuo and the crude product which remains is chromatographed over a silica gel column (silica gel 60—Merck, particle size : 0.04 to 0.063 mm) using the mobile phase of cyclohexane : ethyl acetate (1:1). 11.3 g (37.7% of theory) of N-cyclopropyl-maleimide are obtained.

$^1$H-NMR (400 MHz, CDCl$_3$, δ): 0.84–0.98 (m, 4H, —CH$_2$—CH$_2$—); 2.49–2.56 (m, 1H, —CH—); 6.64 (s, 2H, 2×=CH—) ppm EI-MS m/z (%): 137 (M$^+$, 19).

The compounds listed in the following Table 56 can be prepared analogously:

TABLE 56

Starting substances of the formula (III)

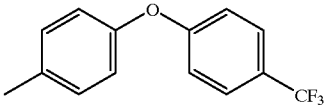
(III)

| Ex. No. | R⁴ | Physical data |
|---|---|---|
| III-3 | —CH₂—CF₃ | 6.86(s, 2H, =CH—)ᵃ⁾ |
| III-4 | -cyclopropylmethyl | 6.73(s, 2H, =CH—)ᵃ⁾, 151(M⁺; 21)ᵇ⁾ |
| III-5 | —CH₂—CH=CH₂ | 6.73(s, 2H, =CH—)ᵃ⁾; melting point: 37–38° C. |
| III-6 | (S)—CH(CH₃)-phenyl | 6.60(s, 2H, =CH—)ᵃ⁾; 201(M⁺; 100)ᵇ⁾ |
| III-7 | (S)—CH(CH₃)—CO—O-tBu | 1.43(s, 3H, —O-tBu); 6.72(s, 2H, =CH—)ᵃ⁾ |
| III-8 | (S)—CH(CH₃)—CO—O—Me | 6.74(s, 2H, =CH—)ᵃ⁾ |
| III-9 | 4-t-butyl-benzyl | 6.69(s, 2H, =CH—)ᵃ⁾; 243(M⁺; 50)ᵇ⁾ melting point: 191° C. |
| III-10 | 2,6-dichloro-benzyl | 6.77(s, 2H, =CH—)ᵃ⁾; 256(M⁺; 2)ᵇ⁾ melting point: 47–48° C. |
| III-11 | 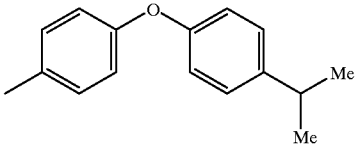 | 6.88(s, 2H, =CH—)ᵃ⁾; 333(M⁺; 100)ᵇ⁾ melting point: 128–129° C. |
| III-12 | 4-bromo-phenyl | 6.86(s, 2H, =CH—)ᵃ⁾; melting point: 109° C. |
| III-13 | 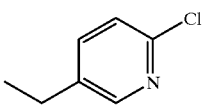 | 6.85(s, 2H, =CH—)ᵃ⁾; 307(M⁺; 60)ᵇ melting point: 112–114° C. |
| III-14 | 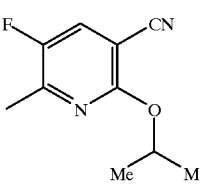 | 6.76(s, 2H, =CH—)ᵃ⁾; 222(M⁺; 100)ᵇ⁾ melting point: 84–85° C. |
| III-15 | 4-F₃C—S-pheny) | 6.89(s, 2H, =CH—)ᵃ⁾; 273(M⁺; 100)ᵇ⁾ |
| III-16 | 3-CF₃, 4-Cl-benzyl | 6.75(s, 2H, =CH—)ᵃ⁾; 290(M⁺; 100)ᵇ⁾ |
| III-17 | 2,6-dimethyl-4-Br-phenyl | 6.88(s, 2H, =CH—)ᵃ⁾; (M⁺; 97)ᵇ⁾ |
| III-17 | 2,4,5-trimethyl-phenyl | 6.83(s, 2H, =CH—)ᵃ⁾; 215(M⁺; 100)ᵇ⁾ mp: 50–51° C. |
| III-18 | 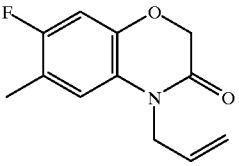 | 6.94(s, 2H, =CH—)ᵃ⁾; 274(M⁺; 100)ᵇ⁾ mp: 103–104° C. |
| III-19 |  | 6.90(s, 2H, =—CH—)ᵃ⁾; 302(M⁺; 100)ᵇ⁾ mp: 102–103° C. |
| III-20 | 4-methy-benzyl | 6.68(s, 2H, =CH—)ᵃ⁾; 201(M⁺; 100)ᵇ⁾ mp: 91–93° C. |
| III-21 | 4-methoxy-benzyl | 6.85(s, 2H, =CH—)ᵃ⁾; 217(M⁺; 100)ᵇ⁾ mp: 95° C. |
| III-22 | 3-chloro-benzyl | 6.73(s, 2H, =CH—)ᵃ⁾; 221(M⁺; 100)ᵇ⁾ mp: 48–50° C. |

TABLE 56-continued

Starting substances of the formula (III)

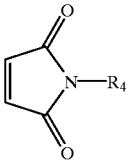

(III)

| Ex. No. | R⁴ | Physical data |
|---|---|---|
| III-23 | 4-chloro-benzyl | 6.71(s, 2H, =CH—)[a]; 221(M⁺; 18)[b] mp: 76–79° C. |
| III-24 | 2-chloro-benzyl | 6.76(s, 2H, =CH—)[a]; 221(M⁺; 3)[b] mp: 57–58° C. |

[a] $^1$H-NMR (400 MHz, CDCl$_3$,) in ppm; EI- or FAB-MS m/z (%)

Example of the preparation of the N-substituted maleamic acids employed as a precursor.

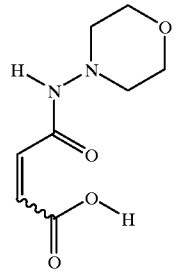

N-aminomorpholine, dissolved in 10 ml of methylene chloride, is added dropwise to a solution of 14.8 g (0.15 mol) of maleic anhydride in 290 ml of methylene chloride at 0° C. and the mixture is then stirred at room temperature for about 18 hours. The entire reac-tion solution is concentrated in vacuo. 25.3 g (83.1% of theory) of (E/Z)-N-morpholino-maleamic acid, which can be reacted further without purification, are obtained.

Melting point: >177° C. (decomposition)

$^1$H-NMR (400 MHz, DMSO-d$_6$, δ): 2.72; 2.77 (2t, 4H, —CH$_2$—N—CH$_2$—; J=4.4 Hz); 3.64; 3.66 (t, 4H, —CH$_2$—O—CH$_2$—; J=4.4 Hz); 6.06; 6.20; 6.30; 6.80 (4d, 4H, 4×=CH—); 9.12; 9.78 (2s, 2H, —NH—); 13.68 (br. s, 1H, —CO—OH) ppm FAB-MS m/z (%): 201 (M⁺+H, 100), 154 (90); 136 (66).

The compounds listed in the following Table 57 can be prepared analogously:

TABLE 56

| Ex. No. | R⁴ | Physical data |
|---|---|---|
| a | (S)—CH(CH$_3$)—CO—O-tBu | 244(M⁺, 23)[b] |
| b | (S)—CH(CH$_3$)—CO—O—Me | |
| c | —NH—CO—O-tBu | 230(M⁺, 1)[b] |
| d | —CH$_2$—CF$_3$ | 9.21(t, NH)[a] |
| e | -cyclopropyl | 9.05(br. s, NH)[a]; mp: 44–45° C. |
| f | -cyctobutyl | 9.32(br. d, NH)[a]; 170(M⁺ + H, 1)[b] |
| g | -cyclopentyl | 9.14(br. d, NH)[a]; 183(M⁺, 13)[b] |
| h | -isobutyl | 9.12(br., NH)[a]; 171(M⁺, 2)[b] |
| i | —CH$_2$—CH=CH$_2$ | 9.15(br. s, NH)[a]; 155(M⁺, 2)[b] |
| j | 2,4,6-trimethyl-phenyl | 233(M⁺, 50)[b]; mp: 148–149° C. |
| k | 4-methylphenyl-O-4-CF$_3$-phenyl | mp: 157° C. |
| l | 4-bromo-phenyl | 10.4(s, NH)[a]; mp: 203–205° C. |
| m | 4-methylphenyl-O-phenyl-CHMe$_2$ | 10.4(s, NH)[a]; 325(M⁺, 23)[b] |

TABLE 56-continued

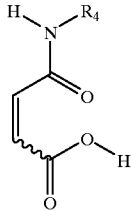

| Ex. No. | R⁴ | Physical data |
|---|---|---|
| n | 4-tBu-biphenyl-4'-ylmethyl | 323(M⁺, 88); 308(100)[b] |
| o | 4-F₃C—S-phenyl | 291(M⁺, 100)[b]; mp: 191° C. |
| p | 3-CF₃, 4-Cl-benzyl | 9.26(t, NH)[a]; mp: 128–130° C. |
| q | 2,6-dichlorobenzyl | 9.26(t, NH)[a]; mp: 165° C. |
| r | 4-t-butyl-benzyl | 9.43(t, NH)[a]; mp: 179–180° C. |

TABLE 57

| Ex. No. | R⁴ | Physical data |
|---|---|---|
| s | morpholinoethyl | 9.09(br. s, NH)[a]; 228(M⁺; 1)[b] |
| t | 2,6-dimethyl-4-Br-phenyl | 297(M⁺; 37)[b]; mp: 178–179° C. |
| u | 2,4,5-trimethyl-phenyl | 233(M⁺; 37)[b]; mp: 104–105° C. |
| v | (F, CN, OCHMe₂-substituted phenyl) | 292(M⁺; 10)[b]; mp: 166–167° C. |
| w | (F, Me-benzoxazinone N-allyl) | 320(M⁺; 76)[b]; mp: 100–102° C. |
| x | 3-chloro-benzyl | 9,29(t, NH)[a]; mp: 118–120° C. |
| y | 4-chloro-benzyl | 9,34(t, NH)[a]; mp: 145–147° C. |
| z | 2-chloro-benzyl | 9,32(t, NH)[a]; mp: 118–120° C. |

[a] ¹H-NMR (400 MHz, DMSO-d₆) in ppm; EI- or FAB-MS m/z (%)

What is claimed is:

1. A method for controlling endoparasites comprising administering to an infected animal susceptible to treatment with, a composition containing 4a, 5a, 8a, 8b-tetrahydro-6H-pyrrolo[3',4': 4,5]furo[3,2-b]pyridine-6,8(7H)-dione derivatives of the general formula (I) and salts thereof,

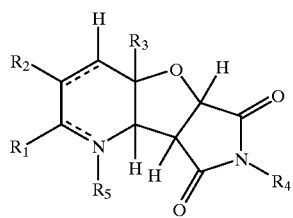

(I)

in which

R¹ represents hydrogen, straight-chain or branched alkyl, cycloalkyl, arylalkyl, aryl, heteroaryl, heteroarylalkyl, which are optionally substituted, R² represents hydrogen, straight-chain or branched alkyl, cycloalkyl, alkoxycarbonyl, which are optionally substituted, R³ represents hydrogen, straight-chain or branched alkyl, cycloalkyl, alkoxycarbonyl, which are optionally substituted, R⁴ represents hydrogen, straight-chain or branched alkyl, alkenyl, alkinyl, cycloalkyl, cycloalkylalkyl, aryl, arylalkyl, heteroaryl, heteroarylalkyl, which are 5–7 membered rings having oxygen and nitrogen, amino, alkylamino, dialkylamino, cycloalkylamino, which are optionally substituted, R⁵ represents hydrogen, straight-chain or branched alkyl, alkenyl, alkinyl, cycloalkyl, cycloalkylalkyl, aryl, arylalkyl, which are optionally substituted, formyl, alkoxydicarbonyl or optionally represents a radical from the group consisting of G¹, G², G³ and G⁴

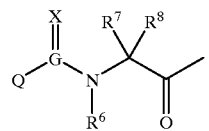

(G¹)

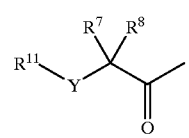

(G²)

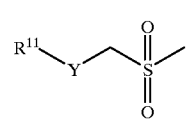

(G³)

(G⁴)

in which

R⁶ represents hydrogen, straight-chain or branched alkyl, cycloalkyl, aryl, arylalkyl, which are optionally substituted, R⁷ and R⁸ independently of one another represent hydrogen, straight-chain or branched alkyl, alkenyl, cycloalkyl, cycloalkylalkyl, aryl, arylalkyl, which are optionally substituted, or $R^7$ and $R^8$ together represent a spirocyclic ring which is optionally substituted,

can denote carboxyl, thiocarboxyl, —C=CH—NO$_2$, —C=CH—CN, —C=C—R$^9$, sulfoxyl, sulfonyl, —P(O)—OR$^{10}$ or P(S)—OR$^{10}$, R$^9$ represents hydrogen, hydroxyl, alkoxy, alkylcarbonyl, halogenoalkylcarbonyl, alkylsulfonyl, nitro or cyano, and R$^{10}$ represents hydrogen or alkyl, and Q represents straight-chain or branched alkyl, alkenyl, alkinyl, cycloalkyl, aryl, arylalkyl, which are optionally substituted, or optionally represents a radical from the group consisting of G$^5$ and G$^8$

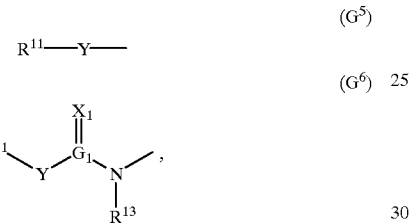

in which

can denote carboxyl, thiocarboxyl or sulfonyl,

Y represents oxygen, sulfur or —NR$^{12}$,

R$^{11}$ and R$^{12}$ independently of one another represent hydrogen, straight-chain or branched alkyl, alkenyl, alkinyl, cycloalkyl, cycloalkylalkyl, aryl, arylalkyl, which are optionally substituted, R$^{13}$ represents hydrogen or alkyl, R$^{14}$ represents hydrogen, straight-chain or branched alkyl, alkenyl, alkinyl, cycloalkyl, cycloalkylalkyl, alkoxycarbonyl, alkylcarbonyl, cycloalkylcarbonyl, cyano, aryl, arylalkyl, which are optionally substituted, wherein the formula (I), the broken line can denote a single bond or represent one or two double bonds between the carbon atom which carries the substituent R$^2$ and the adjacent carbon atom, and/or between the carbon atom and the adjacent nitrogen atom which carry the substituents R$^1$ and R$^5$; and in the case where a double bond is present between the carbon atom which carries the substituent R$^1$ and the adjacent nitrogen atom with a substituent R$^5$, the compounds of the formula (I) are in the form of their salts.

2. The method according to claim 1 in which

R$^1$ represents hydrogen, straight-chain or branched alkyl having up to 4 carbon atoms, C$_{3-6}$-cycloalkyl, aryl-C$_{1-2}$-alkyl, aryl, which are optionally substituted, R$^1$ and R$^2$, together with the atoms to which they are bonded, represent a 5- or 6-membered ring, which is optionally substituted, R$^2$ and R$^3$ independently of one another represent hydrogen, straight-chain or branched alkyl having up to 4 carbon atoms, halogenoalkyl, hydroxyalkyl, C$_{1-4}$-alkanoyloxyalkyl, C$_{1-2}$-alkoxyalkyl, C$_{1-2}$-mercaptoalkyl, C$_{1-2}$-alkylthioalkyl, C$_{1-2}$-alkylsulfinylalkyl, C$_{1-2}$alkylsulfonylalkyl, aminoalkyl, C$_{1-6}$-alkylaminoalkyl, C$_{1-6}$-dialkylaminoalkyl, C$_{3-6}$-cycloalkylaminoalkyl, C$_{3-6}$-cycloalkyl, C$_{1-4}$-alkoxycarbonyl, R$^4$ represents hydrogen, straight-chain or branched C$_{1-6}$-alkyl, halogeno-C$_{1-6}$-alkyl, hydroxy-C$_{1-6}$-alkyl, C$_{1-4}$-alkanoyloxyalkyl, C$_{1-2}$-alkoxyalkyl, C$_{1-4}$alkoxycarbonyl-C$_{1-4}$-alkyl, amino-C$_{1-6}$-alkyl, C$_{1-6}$-alkylamino-C$_{1-6}$-alkyl, C$_{1-6}$-dialkylamino-C$_{1-6}$alkyl, C$_{1-6}$-trialkylammonium-C$_{1-6}$-alkyl halide, C$_{2-6}$-alkenyl, C$_{2-6}$-alkinyl, C$_{3-6}$-cycloalkyl, C$_{3-6}$-cycloalkyl-C$_{1-2}$-alkyl, aryl, aryl-C$_{1-2}$-alkyl, which are optionally substituted, amino, C$_{1-4}$-alkylamino, C$_{1-4}$-dialkylamino, C$_{3-7}$-cycloalkylamino, R$^5$ for hydrogen, straight-chain or branched C$_{1-6}$-alkyl, halogeno-C$_{1-6}$-alkyl, hydroxy-C$_{1-6}$-alkyl, C$_{1-4}$-alkanoyloxyalkyl, C$_{1-2}$-alkoxyalkyl, amino-C$_{1-6}$-alkyl, C$_{1-6}$-alkylamino-C$_{1-6}$-alkyl, C$_{1-6}$-dialkylamino-C$_{1-6}$-alkyl, C$_{1-6}$-trialkylammonium-C$_{1-6}$-alkyl halide, nitro-C$_{1-4}$-alkyl, cyano-C$_{1-4}$-alkyl, C$_{1-4}$-alkoxycarbonyl-C$_{1-4}$-alkyl, carbamoyl-C$_{1-4}$-alkyl, carboxyl-C$_{1-4}$-alkyl, C$_{2-6}$-alkenyl, C$_{2-6}$-alkinyl, C$_{3-6}$-cycloalkyl, C$_{3-6}$-cycloalkyl-C$_{1-2}$-alkyl, aryl, aryl-C$_{1-2}$-alkyl-C$_{1-2}$-alkyl, formyl, C$_{1-4}$-alkoxydicarbonyl, or for a radical from the group consisting of G$^1$, G$^2$, G$^3$ and G$^4$

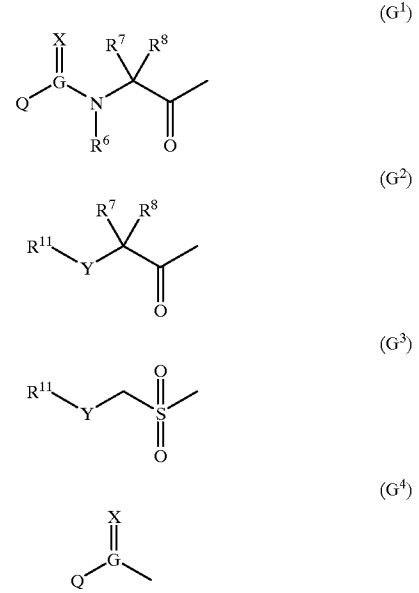

in which

R$^6$ represents hydrogen, straight-chain or branched C$_{1-6}$-alkyl, C$_{3-6}$-cycloalkyl, aryl-C$_{1-2}$-alkyl, which are optionally substituted, R$^7$ and R$^8$ independently of one another represent hydrogen, straight-chain or branched C$_{1-6}$-alkyl, halogeno-C$_{1-6}$-alkyl, hydroxy-C$_{1-6}$-alkyl, C$_{1-4}$- alkanoyloxy-$C_{1-6}$-alkyl, $C_{1-2}$-alkoxy-$C_{1-6}$-alkyl, mercapto-$C_{1-6}$-alkyl, $C_{1-2}$-alkylthio-$C_{1-6}$-alkyl, $C_{1-2}$alkylsulfinyl-$C_{1-6}$-alkyl, $C_{1-2}$-alkylsulfonyl-$C_{1-6}$alkyl, carboxyl-$C_{1-6}$-alkyl, carbamoyl-$C_{1-6}$-alkyl, amino-$C_{1-6}$-alkyl, $C_{1-6}$alkylamino-$C_{1-6}$-alkyl, $C_{1-6}$-dialkylamino-$C_{1-6}$-alkyl, guanidino-$C_{1-6}$-alkyl, which radical can optionally be substituted by one or two benzyloxycarbonyl radicals or by one, two, three or four $C_{1-2}$-alkyl radicals, $C_{1-4}$-alkoxycarbonylamino-$C_{1-6}$-alkyl, $C_{2-6}$-alkenyl, $C_{3-6}$-cyclo-$C_{1-2}$-alkyl, $C_{3-6}$-cycloalkyl-$C_{1-2}$-alkyl, and represent optionally substituted aryl, aryl-$C_{1-2}$-alkyl, or $R^7$ and $R^8$ together represent a spirocyclic ring,

denotes carboxyl, thiocarboxyl, —C=CH—$NO_2$, —C=CH—CN, —C=C—$R^9$, sulfoxyl, sulfonyl, —P(O)—$OR^{10}$ or P(S)—$OR^{10}$, $R^9$ represents hydrogen, hydroxyl, $C_{1-4}$-alkoxy, $C_{1-4}$-alkylcarbonyl, halogeno-$C_{1-4}$-alkylcarbonyl, $C_{1-4}$-alkylsulfonyl, nitro or cyano, and $R^{10}$ represents hydrogen or $C_{1-4}$-alkyl, and Q represents straight-chain or branched $C_{1-6}$-alkyl, halogeno-$C_{1-6}$-alkyl, hydroxy-$C_{1-6}$-alkyl, $C_{1-4}$-alkanoyloxyalkyl, $C_{1-2}$-alkoxyalkyl, mercaptoalkyl, $C_{1-2}$-alkylthioalkyl, $C_{1-2}$-alkylsulfinylalkyl, $C_{1-2}$-alkylsulfonylalkyl, carboxyalkyl, carbamoylalkyl, amino-$C_{1-6}$-alkyl, $C_{1-6}$-alkylamino-$C_{1-6}$-alkyl, $C_{1-6}$-dialkylamino-$C_{1-6}$-alkyl, guanidino-$C_{1-6}$-alkyl, which radical can optionally be substituted by one or two benzyloxycarbonyl radicals, tert-butyloxycarbonyl radicals or by one, two, three or four $C_{1-2}$-alkyl radicals, $C_{1-4}$-alkoxycarbonylaminoalkyl, $C_{2-6}$-alkenyl, $C_{2-6}$-alkinyl, $C_{3-6}$-cycloalkyl, aryl, aryl-$C_{1-2}$-alkyl, which are optionally substituted, or optionally represents a radical from the group consisting of $G^5$ and $G^6$ (G⁵)

$R^{11}$—Y—

-continued

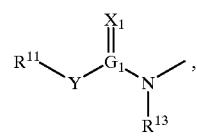

(G⁶)

in which

can denote carboxyl, thiocarboxyl or sulfonyl,

Y represents oxygen, sulfur or —$NR^{12}$, $R^{11}$ and $R^{12}$ independently of one another represent hydrogen, straight-chain or branched $C_{1-6}$-alkyl, $C_{2-6}$-alkenyl, $C_{2-6}$-alkinyl, $C_{3-6}$-cycloalkyl, $C_{3-6}$-cycloalkyl-$C_{1-2}$-alkyl, aryl, aryl-$C_{1-2}$-alkyl, which are optionally substituted, or $R^{13}$ represents hydrogen or $C_{1-4}$-alkyl, $R^{14}$ represents hydrogen, straight-chain or branched $C_{1-6}$-alkyl, $C_{1-6}$-alkenyl, $C_{2-6}$-alkinyl, $C_{3-8}$-cycloalkyl, $C_{3-8}$-cycloalkyl-$C_{1-2}$-alkyl, $C_{1-4}$-alkoxycarbonyl, $C_{1-4}$-alkylcarbonyl, $C_{3-6}$-cycloalkylcarbonyl, cyano, aryl, aryl-$C_{1-2}$-alkyl, stand, which are optionally substituted, and optical isomers and racemates thereof, for control of endoparasites in medicine and veterinary medicine.

3. An endoparasiticidal composition comprising 4a, 5a, 8a, 8b-tetrahydro-6H-pyrrolo[3', 4': 4,5]furo[3,2-b]pyridine-6,8(7H)dione derivative of the formula (I) according to claim 1, in combination with a physiologically acceptable solvent.

4. A method of preparing an endoparasiticidal composition comprising a compound 4a, 5a, 8a, 8b-tetrahydro-6H-pyrrolo[3', 4': 4,5]furo[3,2-b]pyridine-6,8(7H)-dione derivative of the formula (I) according to claim 1 comprising optionally combining the compound with a physiologically acceptable solvent, carrier or an auxiliary.

\* \* \* \* \*